(12) United States Patent
Sokol et al.

(10) Patent No.: US 8,992,893 B2
(45) Date of Patent: Mar. 31, 2015

(54) METHOD OF INHIBITING HARMFUL MICROORGANISMS AND BARRIER-FORMING COMPOSITION THEREFOR

(75) Inventors: Brian Vincent Sokol, Vermillion, OH (US); Afif Mahmoud Ghannoum, Shaker Hts., OH (US)

(73) Assignee: ARMS Pharmaceutical, LLC, Cleveland, OH (US)

(*) Notice: Subject to any disclaimer, the term of this patent is extended or adjusted under 35 U.S.C. 154(b) by 63 days.

(21) Appl. No.: 13/448,957

(22) Filed: Apr. 17, 2012

(65) Prior Publication Data

US 2012/0270909 A1    Oct. 25, 2012

Related U.S. Application Data

(60) Provisional application No. 61/477,147, filed on Apr. 19, 2011.

(51) Int. Cl.
| | | |
|---|---|---|
| *A61Q 11/00* | (2006.01) | |
| *A61K 9/00* | (2006.01) | |
| *A61K 31/155* | (2006.01) | |
| *A61K 31/4425* | (2006.01) | |

(52) U.S. Cl.
CPC .............. *A61K 9/006* (2013.01); *A61K 31/155* (2013.01); *A61K 31/4425* (2013.01)
USPC .......................................................... 424/49

(58) Field of Classification Search
CPC .... A64K 31/55; A64K 9/006; A64K 31/4425
See application file for complete search history.

(56) References Cited

U.S. PATENT DOCUMENTS

| | | | |
|---|---|---|---|
| 3,993,777 A | 11/1976 | Caughman et al. | |
| 4,590,057 A | 5/1986 | Hicks | |
| 4,657,758 A | 4/1987 | Goldemberg et al. | |
| 5,095,106 A | 3/1992 | Gaffar et al. | |
| 5,124,359 A | 6/1992 | Wachman et al. | |
| 5,401,723 A | 3/1995 | Gaffar | |
| 5,422,098 A | 6/1995 | Rolla et al. | |
| 5,733,540 A | 3/1998 | Lee | |
| 5,776,479 A | 7/1998 | Pallos et al. | |
| 6,368,576 B1 | 4/2002 | Jensen et al. | |
| 6,663,902 B1 | 12/2003 | Hei et al. | |
| 6,682,722 B2 * | 1/2004 | Majeti et al. .................... | 424/53 |
| 6,713,049 B1 | 3/2004 | White, Jr. et al. | |
| 6,749,869 B1 | 6/2004 | Richter | |
| 6,977,082 B2 | 12/2005 | Seitz, Jr. et al. | |
| 8,535,646 B2 | 9/2013 | Sokol et al. | |
| 2002/0156130 A1 | 10/2002 | Melman | |
| 2003/0232074 A1 | 12/2003 | Lipford | |
| 2004/0009245 A1 | 1/2004 | Vail, III et al. | |
| 2004/0126334 A1 | 7/2004 | White, Jr. et al. | |
| 2005/0025833 A1 | 2/2005 | Aschkenasy et al. | |
| 2005/0058673 A1 | 3/2005 | Scholz | |
| 2005/0169852 A1 | 8/2005 | Roberge et al. | |
| 2005/0182021 A1 | 8/2005 | Nichols et al. | |
| 2006/0063712 A1 | 3/2006 | Chiueh | |
| 2006/0166943 A1 | 7/2006 | Van Roey et al. | |
| 2006/0251684 A1 * | 11/2006 | Annis et al. .................... | 424/400 |
| 2007/0037723 A1 | 2/2007 | McDonnell et al. | |
| 2007/0281999 A1 | 12/2007 | Fox et al. | |
| 2008/0064711 A1 * | 3/2008 | Friedman ....................... | 514/277 |
| 2008/0206155 A1 | 8/2008 | Tamarkin et al. | |
| 2008/0255498 A1 | 10/2008 | Houle | |
| 2008/0317703 A1 | 12/2008 | Kawa et al. | |
| 2009/0081294 A1 | 3/2009 | Gin et al. | |
| 2009/0149429 A1 | 6/2009 | Arranz Plaza et al. | |
| 2010/0055152 A1 | 3/2010 | Wahi | |
| 2013/0272971 A1 * | 10/2013 | Pimenta et al. ................. | 424/52 |

FOREIGN PATENT DOCUMENTS

| | | |
|---|---|---|
| DE | 19529862 A2 | 2/1997 |
| EP | 0376363 A1 | 11/1989 |
| EP | 0351301 A2 | 1/1990 |
| EP | 0736250 | 10/1996 |
| EP | 1930012 A1 | 6/2008 |
| EP | 2193777 A1 | 6/2009 |
| EP | 2119426 A1 | 11/2009 |
| EP | 2226069 A1 | 9/2010 |
| EP | 2377577 A2 | 10/2010 |
| EP | 2298418 A1 | 3/2011 |
| EP | 2377577 A1 | 10/2011 |
| RU | 2302865 C2 | 6/2005 |

(Continued)

OTHER PUBLICATIONS

Sokol, B., Ghannoum, A., U.S. Appl. No. 13/655,365, filed Oct. 18, 2012.
Sokol, B., Ghannoum, A., U.S. Appl. No. 13/448,926, filed Apr. 17, 2012.
Ghannoum, A., Sokol, B., "Long-Lasting Surface Anti-Microbial and Method of Application," U.S. Appl. No. 13/734,363, filed Jan. 4, 2013.
Ghannoum, A., Sokol, B., "Method for Reducing Microbial Load for Individuals with Elevated Risk Conditions," U.S. Appl. No. 13/734,470, filed Jan. 4, 2013.
Department of Health and Human Services (Food and Drug Administration) (1994) Oral Health Care Drug Products for Over-the-Counter Human Use; Tentative Final Monograph for Oral Antiseptic Drug Products. Proposed Rules. Federal Register 59:6084-124.

(Continued)

*Primary Examiner* — Lezah Roberts
*Assistant Examiner* — Nannette Holloman
(74) *Attorney, Agent, or Firm* — Medley, Behrens & Lewis, LLC; Nathan T. Lewis

(57) ABSTRACT

In an embodiment, the barrier-forming composition includes a carbohydrate gum, a humectant, and an antimicrobial agent. The composition furthermore meets the following requirements: about 0.01%≤C≤about 0.4%; about 4.5%≤H≤about 65%; and 0.050%<A; or about 0%≤C≤about 0.4%; about 55%≤H≤about 65%; and 0.050%<A. C is the carbohydrate gum; H is the humectant; and A is the antimicrobial agent. All percentages are by weight of the total composition. In an embodiment the barrier-forming composition has an Rf value in water of 0 to about 0.25.

25 Claims, 33 Drawing Sheets

(56) References Cited

FOREIGN PATENT DOCUMENTS

| RU | 2325899 | 6/2008 |
|---|---|---|
| WO | 9959410 | 11/1999 |
| WO | 0027191 | 5/2000 |
| WO | 200701606 A2 | 2/2007 |
| WO | 2007016067 A3 | 2/2007 |
| WO | 2009067605 | 5/2009 |

OTHER PUBLICATIONS

Piteen, Frank-Albert et al., "Efficacy of Cetylpyridinium Chloride Used as Oropharyngeal Antiseptic" Arzneim.-Forsch/Drug Res. 51 (II), 588-595 (2001).

Johannes, Laura, "Keeping Cold and Flu Germs Out" Wall Street Journal (online) (Dec. 6, 2011) (retrieved on May 4, 2012 from http://online.wsj.com/article/SB10001424052970204903804577080410897264148.html?mod=WSJ_article_comments#articleTabs%3Darticle ).

Patent Translate, English Translation of EP 0351301 (generated on Jun. 6, 2012).

PCT Search Authority, International Search Report (Sep. 6, 2012).

PCT Search Authority, Written Opinion of the International Searching Authority (Sep. 6, 2012).

Roberts, Lezah, Non-Final Office Action in U.S. Appl. No. 13/448,926 (Nov. 27, 2012).

US Department of Health and Human Services, Periodontal (Gum) Disease: Causes, Symptoms and Treatments, Jan. 2006, pp. 1-16.

Vladimirova, T., PCT Search Report and Written Opinion, PCT/US2013/066863, Jan. 30, 2014 (6 pages).

Vladimirova, T., PCT Search Report and Written Opinion, PCT/US2013/066929, Feb. 6, 2014 (8 pages).

Vladimirova, T., PCT Search Report and Written Opinion, PCT/US2014/010174, Apr. 29, 2014 (9 pages).

Machine Translation of German Patent No. 19529862, Publication Date of Feb. 20, 1997 (7 pages).

Roberts, Lezah, Office Action in U.S. Appl. No. 13/734,363, Apr. 26, 2013 (20 pages).

Roberts, Lezah, Office Action in U.S. Appl. No. 13/448,926, May 3, 3013 (30 pages).

Lambert Phamacal Co., "So many times in a day in Danger", Life magazine, Dec. 1927 (3 pages).

Roberts, Lezah, Office Action in U.S. Application 13/734,470, Mar. 21, 2013 (21 pages).

Vukovic, L., Basic Health Publications: Users Guide to Echinacea and Other Cold & Flu Fighters, p. 7 (2004).

Maslova, E., PCT Search Report and Written Opinion, PCT/US2013/020254, May 16, 2013 (6 pages).

Roberts, Lezah, Office Action in U.S. Appl. No. 13/734,363, Nov. 8, 2013 (11 pages).

Roberts, Lezah, Office Action in U.S. Appl. No. 13/655,365, Mar. 21, 2014 (14 pages).

Roberts, Lezah, Final Office Action in U.S. Appl. No. 13/734,470 (Jan. 6, 2014). pp. 1-23.

Roberts, Lezah, Office Action in U.S. Appl. No. 14/014,448 (Jan. 16, 2014). pp. 1-20.

Roberts, Lezah, Final Office Action for U.S. Appl. No. 14/014,448, Oct. 24, 2014, 20 pages.

O'Shea, Chloe, First Examination Report for New Zealand Application No. 616044, Jul. 16, 2014, 3 pages.

\* cited by examiner

METHOD OF INHIBITING HARMFUL MICROORGANISMS AND BARRIER-FORMING COMPOSITION THEREFOR

CROSS-REFERENCE TO RELATED APPLICATION

This application claims the benefit of priority to U.S. provisional application No. 61/477,147, filed on Apr. 19, 2011, entitled "Compositions, Methods of Use, and Methods of Making Barrier Products." That provisional application is incorporated herein by reference for all purposes.

FIELD

This disclosure relates to barrier-forming compositions and methods for preventing communicable diseases.

BACKGROUND

There has been a longstanding need for devices, compositions, and other treatments that will effectively prevent communicable diseases. Attempts at solving this problem include wearing masks or respirators and avoiding or quarantining of individuals or animals that are known or expected to be sick or carrying germs. Such approaches are common in certain countries where masks are worn by persons encountering contaminated environments such as public transportation or public gathering places.

Other attempts to prevent infection have included large amounts of zinc, vitamins, or herbs that are theorized to work internally to boost the body's immune system.

While numerous solutions exist for killing microorganisms once they have contacted a person or animal, the effectiveness of such solutions is dependent on quick recognition of the germ contact and application of the germ-killing composition prior to the microorganism binding to a mucosa, whereby it would enter the body and infect the individual. For example, washing with an anti-bacterial soap may be effective for killing germs on the hands; however, it is very easy for a person to unwittingly touch a contaminated surface and put their hands near or in their mouth or nose before washing their hands.

Physical devices such as masks are uncomfortable, zinc, vitamin C, and herbal remedies have unproven results, and solutions for killing germs that have already contacted the body are often ineffective for prevention of infection since they are intermittent, transitory options that do not provide sustained protection.

Compositions have been developed for forming blocking barriers topically on human skin or in the oral or internal cavities. However, such compositions are not for preventing infection of communicable diseases.

SUMMARY

In an embodiment, the barrier-forming composition includes a carbohydrate gum, a humectant, and an antimicrobial agent. The composition furthermore meets the following requirements: about $0.01\% \leq C \leq about\ 0.4\%$; about $4.5\% \leq H \leq about\ 65\%$; and $0.050\% < A$; or about $0\% \leq C \leq about\ 0.4\%$; about $55\% \leq H \leq about\ 65\%$; and $0.050\% < A$. C is the carbohydrate gum; H is the humectant; and A is the antimicrobial agent. All percentages are by weight of the total composition.

In an embodiment, the barrier-forming composition includes a carbohydrate gum, a humectant, and an antimicrobial agent. The composition meets the following requirements: about $0.01\% \leq C \leq about\ 0.4\%$; and about $4.5\% \leq H \leq about\ 65\%$; or about $0\% \leq C \leq about\ 0.4\%$; and about $55\% \leq H \leq about\ 65\%$. All percentages are by weight of the total composition. The barrier-forming composition has an Rf value in water of 0 to about 0.25.

In an embodiment, a method for making a mucosal barrier-forming composition includes mixing and heating: a carbohydrate gum; a humectant; and an antimicrobial agent. The composition meets the following requirements: about $0.01\% \leq C \leq about\ 0.4\%$; about $4.5\% \leq H \leq about\ 65\%$; and $0.050\% < A$; or about $55\% \leq C \leq about\ 65\%$; about $0\% \leq H \leq about\ 0.4\%$; and $0.050\% < A$. All percentages are by weight of the total composition.

The articles "a" and "the," as used herein, mean "one or more" unless the context clearly indicates to the contrary.

The terms "item" and "apparatus" are used synonymously herein.

The term "therapeutic," as used herein, is meant to also apply to preventative treatment.

The term "or," as used herein, is not an exclusive or, unless the context clearly indicates to the contrary.

DETAILED DESCRIPTION

Figure 1:
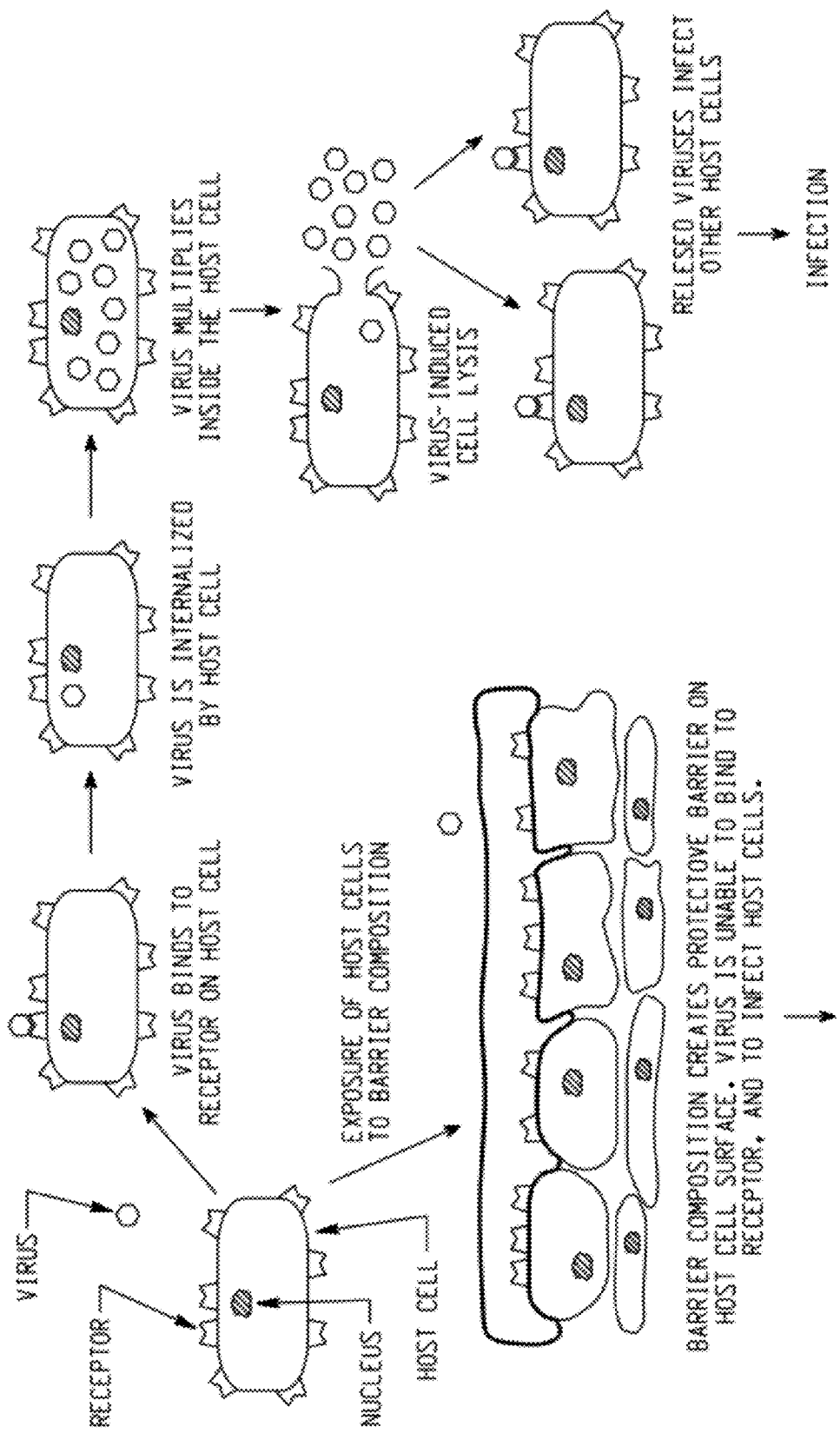
FIG. 1 is a depiction of a proposed mechanism of antimicrobial activity in an embodiment of the barrier-forming composition.

The mucosa lining the mouth, gut, and body cavities of mammals represents the first barrier to the entry of pathogenic microorganisms to mammalian bodies where they can cause both local and systemic infections. The epithelium mucosal lining forms a barrier that reduces the entry of commensals organisms (Monica Boirivanta and Warren Strober, "The Mechanism of Action of Probiotics" Current Opinion in Gastroenterology 2007, 23:679-692).

In this application, a method and composition is disclosed that blocks or neutralizes microorganisms that cause infectious disease from contacting or infecting mucosa, which in turn prevents microorganisms from disseminating into body and causing infection. The method and composition incorporates an antimicrobial agent that can inhibit microorganisms (bacteria, fungi, and viruses) known to cause infections. The method protects human mucosa by forming a barrier over it and an antimicrobial agent is included that can kill or inhibit microorganisms (bacteria, fungi and viruses). This dual action composition and method (barrier plus antimicrobial) is applicable to human or other mammal mucosa or, for example, surfaces in the oral cavity, nasal cavity, vaginal cavity, throat, and other orifices, including, but not limited to, the ears. It can also be applied to medical devices, such as trachea devices. This unique and unexpected solution addresses a long-felt but unresolved need for preventing communicable diseases caused by microorganisms.

A barrier-forming composition that is safe (i.e. does not cause damage to the mucosa) and forms a barrier that inhibits the passage of pathogenic microbes through the mucosal tissues is desirable. Another desirable property is an ability to inhibit microbial growth through static or cidal activity for an extended period of time. Without being bound by theory, the mechanism of action of the barrier-forming composition disclosed herein is based on a synergistic dual-action mechanism, in which germs are trapped in the formed barrier, and subsequently killed by the antimicrobial active ingredient. In an embodiment the barrier-forming composition is not hydrophilic, which, without being bound by theory, is theorized to enhance it sustained effectiveness.

As shown in the Examples below, the properties of the barrier-forming composition and its effectiveness to prevent a wide variety of communicable diseases were assessed using at least ten different approaches based on: (1) an in vitro anti-microbial susceptibility testing; (2) an in vitro time kill assay; (3) an in vitro biofilm model; (4) an in vitro filter insert-based model, (5) an in vivo-like engineered human oral mucosa (EHOM) model; (6) electron microscopy evaluation;

(7) hydrophobicity assay; (8) physico-chemical compatibility assays; (9) cell culture-based model using monolayer of human cell lines; and (10) human clinical trials.

The method and composition described herein may be particularly useful when a human, or more generally, a mammal, has a disrupted mucosa. A disruption may be caused be a wound or scratch. The mucosa of the oral cavity and gastrointestinal (GI) tract serve as an important mechanical barrier that helps to prevent a local or systemic invasion of various microbes and the absorption of microbial products that are normally present in the oral cavity and the lumen of the gut. "Gastrointestinal mucosal injury in experimental models of shock, trauma, and sepsis," Crit. Care Med. 1991; 19:627-41.). Derangement in the barrier function of the mucosa plays a central role in the pathophysiology of systemic infection. In other words, disruption of this mucosa will lead to infections.

Elimination or reduction of the risk of a breach in the first line of defense is important, and the maintenance of mucosal integrity is important. (Anders Heimdahl, "Prevention and Management of Oral Infections in Cancer Patients" Supportive Care in Cancer, Vol. 7, No. 4, 224-228 (1999).) Thus, having an intact mucosa is an important host defense against systemic infection, particularly in immunocompromised patients (e.g. cancer patients). (Shahab A. Khan, John R. Wingard, "Infection and Mucosal Injury," Cancer Treatment Journal of the National Cancer Institute, Monographs No. 29 (2001). A barrier-forming composition that blocks and kills harmful microorganisms and that does not interfere with healing of a disrupted mucosa is a unique and unexpected solution to the susceptibility of the problems of those with disrupted mucosa, particularly those that also have immunodeficiency.

In an embodiment, a barrier-forming composition may be administered in a method for preventing or inhibiting an infectious disease in a mammal. By prevention, it is not meant that no infection from microorganisms is possible, but that the risk of infection from microorganisms encountered subsequent to application of the barrier-forming composition is reduced. For the full preventive effect, the barrier-forming composition should be applied prior to the mammal encountering a contaminated environment or item. This is not to say that some benefit could not be obtained from administering the barrier-forming composition during the encounter with a contaminated environment or item. The use of the term "mammal" herein, means a human or animal commonly defined as a mammal.

In another embodiment, a barrier-forming composition is administered in a method preventing an infectious disease in mammal with a disrupted mucosa, such as for example an immunocompromised mammal. The disrupted area in a mucosa of the mammal is identified and a therapeutically effective amount of a barrier-forming composition is administered to at least the disrupted area of the mucosa of the mammal. The barrier-forming composition provides a barrier on the disrupted area of the mucosa that effectively inhibits microorganisms from disseminating to a disrupted area of the mucosa.

In another embodiment, the barrier-forming composition is administered on an item or apparatus prior to the apparatus encountering a contaminated environment and prior to the apparatus encountering a mucosa of a mammal. The barrier-forming composition provides a barrier on the apparatus that traps and kills the microorganisms, thereby preventing the microorganisms from passing to the mucosa or causing infection.

In an embodiment of the method of preventing an infectious disease, a step includes identifying a contaminated environment that the mammal or item is expected to encounter. The contaminated environment is an environment such as an indoor or outdoor space or a proximity to another mammal or human that is known or expected to be contaminated with harmful viral, fungal, or bacterial microorganisms. The determination of whether a given environment may be contaminated may be based on the time of year, published information on flourishing diseases in the community, or observing others that appear to be sick or spreading germs by sneezing, etc.

Predicting or identifying whether the contaminated environment or item will be encountered can be a decision based on whether the mammal plans or expects to enter the environment or encounter the item in the near future. This may include estimating a time when the contaminated environment or item will be encountered. The barrier-forming composition may then be administered about twenty-four hours or less prior to the estimated time of encounter with the contaminated environment or item, such as, for example, about sixteen hours or less, about twelve hours or less, about six hours or less, or about two hour or less. The barrier-forming composition sets up quickly and should be operable to prevent or inhibit harmful microorganisms from infecting mucosa, for example, within less than one minute of application, such as within 30 seconds. Thus, it could be applied during the encounter with the contaminated environment or item and have effectiveness.

Harmful microorganisms are those known to cause infectious disease such as, for example, the treatment and prevention of infectious diseases, such as communicable diseases caused by microorganisms, such as *Candida* species (e.g. *C. albicans, C. glabrata, C. krusei, C. tropicalis*), *Staphylococcus* species (including methicillin-resistant *S. aureus*, MRSA), *Streptococcus* species (e.g. *S. sanguis, S. oxalis, S. mitis, S. salivarius, S. gordonii, S. pneumoniae*), *Acinetobacter baumannii, Aggregatibacter actinomycetemcomitans, Fusobacterium nucleatum*, and other microorganisms such as microorganisms that cause upper respiratory infections, and cold and influenza viruses. In an embodiment, the barrier-forming composition and method of treatment and prevention described herein may be useful, for example, for prevention of sexually transmitted diseases [such as, for example, infections caused by human immunodeficiency virus (HIV), Herpes simplex, or human papilloma virus (HPV)], common cold (e.g. caused by rhinovirus), and infections caused by Epstein-Barr Virus (EBV).

The barrier-forming composition has shown effectiveness against microorganisms with a diameter of, for example, about 30 nm or greater, such as about 100 nm (HIV, spherical), about 100 to about 300 nm (influenza, spherical and elongated forms), about 120 nm to about 260 nm (EBV spherical/disk forms), and about 30 nm (rhinovirus, spherical). Thus, the composition should also be effective against other microorganisms with diameters of about 30 nm, or greater than about 30 nm.

The microorganisms may be air-borne microorganisms. In an embodiment the microorganisms are those that cause communicable diseases. In an embodiment, the microorganisms do not include those that cause allergic reactions or dental problems, such as, for example, cavities (caries), gingivitis, or seasonal allergies. Similarly, in an embodiment, the method of prevention does not solely or additionally prevent dental problems or allergic reactions, such as, for example, cavities (caries), gingivitis, or seasonal allergies. In another embodiment, however, microorganisms, such as fungi that may generally be classified as allergens, other allergens, and airborne irritants to the mucosa, are blocked by the barrier and the method. In the allergen blocking embodiment, the identification of the contaminated environment may, for example, be based on the season of the year, or pollen or other allergen or irritant forecasts. It may also be based, for example, on the mammal's expectation to be in a location known or expected to produce a high number of allergens or airborne irritants, such as, for example, an outdoor environment, including, for example, a forest, a park, or a lake.

In an embodiment, the barrier-forming composition and method of treatment and prevention described herein may be useful, for example, for prevention of infections in environments such as hospitals and infections common in such environments that are contaminated with infectious microorganisms. As mentioned above, the methods and compositions disclosed herein may be especially applicable for immunocompromised patients. In addition, the barrier-forming composition may be useful for prevention of infections by microorganisms that commonly infect wounds.

The contaminated environment may include, for example, a public transportation vehicle, a public gathering place, and a room or vehicle containing a mammal known or expected to be ill, or a close proximity to a mammal known or expected to be ill. More information on environments commonly recognized as contaminated environments, such as an airplane, a nursery, and a health center, is disclosed in Yang, et al., "Concentrations and Size Distributions of Airborne Influenza A Viruses Measured Indoors at a Health Centre, a Day-Care Centre, and on Aeroplanes," J.R. Soc. Interface (Feb. 7, 2011), which is incorporated herein by reference.

More specifically, in an embodiment, the public transportation vehicle may be, for example, an airplane, a bus, or a taxi. A public gathering place may be, for example, a doctor's office, a hospital, a school, a nursery, a church, a hotel, or a restaurant. The close proximity to a mammal known or expected to be ill may be, for example, within a one foot radius, or in the same motor vehicle with the mammal. A publicly used airplane may be mentioned as a common and particularly noteworthy example of an environment that many would identify as being a contaminated environment.

In an embodiment, the barrier-forming composition and method of treatment and prevention described herein may be useful, for example, for prevention of infections from items that may be contaminated in activity related treatments, such as, for example, ventilator use (which would include medical devices related to the ventilator and contacting the patient). As another example of a contaminated item, treatment and prevention of fungal infections through applications to the body, and or items or surfaces coming into contact with the body, such as shoes, may also be mentioned. In an embodiment the contaminated item may be, for example, a food, a drink, utensils, drink containers and accessories, an item for use by children, a medical apparatus, or a dental apparatus.

In an embodiment of the method of preventing an infectious disease, a step includes administering a therapeutically effective amount of a barrier-forming composition to a mucosa of the mammal prior to the mammal encountering the contaminated environment or item. By a therapeutically effective amount, it is meant enough to coat the targeted mucosa with enough of the barrier-forming composition to form a barrier that will result in a barrier layer forming on the mucosa. For example, about 100 microliters to about 10 ml, such as, for example, about 1 ml to about 8 ml, or about 2 ml to about 5 ml for a mouthwash formulation, or about 0.125 ml to about 2 ml, such as about 0.5 ml to about 1 ml for a spray formulation. The dosage amount may also be expressed in terms of a volume per square cm, such as, for example, from about 0.5 to about 50 $\mu l/cm^2$, such as, about 5 to about 40 $\mu l/cm^2$, or about 10 to about 25 $\mu l/cm^2$ for a mouthwash formulation; or for a spray formulation, for example, about 0.625 to about 10 $\mu l/cm^2$, such as, about 2.5 to about 5 $\mu l/cm^2$. Other delivery mediums, such as dissolvable strips, may have dosages derived from these ranges given the adjustments for concentrations and other factors known to those of skill in the art. In addition, the average thickness of the film formed on the mucosa from the barrier-forming composition may range, for example, from about 0.001 to about 0.2 mm, such as about 0.01 mm to about 0.1, or about 0.08 to about 0.15 mm. For example, for a given human or animal, the therapeutically effective amount can be determined based on the age or weight or size of the mammal to be treated, and the dosage may be those listed above. For non-human mammals, in particular, the dosage amount may be adjusted according to the per square cm values given above and the approximate surface area of the mucosal surface or body cavity to be treated.

In an embodiment, the barrier-forming composition administered in a therapeutically effective amount to a mucosa provides a barrier layer on the mucosa that inhibits the microorganisms from penetrating to the mucosa. In an embodiment, the inhibition of the microorganisms also includes killing or deactivating the microorganism's harmful activity. In an embodiment, the barrier-forming composition blocks and/or kills all harmful microorganisms contacting the barrier-forming composition. In another embodiment, the barrier substantially blocks and/or kills enough harmful microorganisms to prevent them from causing an infectious disease. In the latter case, if the harmful microorganism's penetration of the mucosa is slowed and/or diluted it will enhance the body's own ability to prevent the microorganisms from causing disease or widespread infection. In vitro testing demonstrates that embodiments of the barrier-forming composition prevent all bacteria from reaching the mucosal surface for long periods, including about six hours or more, about sixteen hours or more, and about twenty-four hours or more. In vitro testing shows that in viruses exposed to embodiments of the barrier-forming composition, growth may be inhibited for about two or more days (such as influenza), to about nine days, (such as HIV), after which the viral count is still below the MIC for extended periods, such as about two or three days Inhibitory activity against influenza virus was observed for up to 48 hours.

In vivo testing indicates that embodiments of the barrier-forming composition are therapeutically effective to reduce microbial count in the oral cavity for about six hours or more.

In an embodiment, in a continued dosage method of prevention or treatment, the barrier-forming composition may be administered in a series of doses, such as, for example, about every 1 to 12 hours, about every 2 to 8 hours, or about every 4 to 6 hours. This method of prevention can be continued, for example, for a day or more, such as for about two days to about a week. This continued dosage method may be preferred when the subject is in prolonged contact with a contaminated environment or item. In vivo testing has shown that about 80% of humans following the continued dosage method show a decrease of about 50% or greater of microbial load in the oral cavity over six days of treatment.

The mucosa, may, for example, may be a mucosal surface in the oral cavity, the nasal cavity, or the pharyngeal cavity, such as, the nasopharynx (epipharynx), the oropharynx (mesopharynx), or the laryngopharynx (hypopharynx). The mucosa may also be in the vaginal cavity, stomach, intestine, throat or other orifices of a mammal, including, but not limited to the ear canal.

In an embodiment, administering the composition includes taking the barrier-forming composition in a mouthwash form so as to contact the oral mucosa of the mammal. After a selected amount of time in the oral cavity, e.g. at least about 10 seconds, for example about 15 seconds to about 5 minutes, or about 1 minute to about 3 minutes. Subsequently the composition is discharged from contact with the oral cavity. In another embodiment, the composition is administered by spraying into an oral or nasal orifice of the mammal. Other administration methods include, for example, rubbing or applying a gelled barrier-forming composition onto the mucosa. The barrier-forming composition may be administered to a mammal through many different delivery systems, including, for example: liquids, gels, lubricants, lotions, creams, pastes, aerosolized particles, strips, sprays, rinses, dressings, such as for wound dressings, infusion or layering of the barrier-forming composition into or onto products, such as on condoms, lozenges, or gums. For example, the barrier-forming composition may be administered in the form of a lozenge with a liquid center comprising the barrier-forming composition, or a dissolvable strip comprising the barrier-forming composition.

In an embodiment, the barrier composition may be used to combat transmission of harmful microorganisms from hand-to-mouth or hand-to-nose contact. In this embodiment, the barrier composition is applied to block neutralize or kill microorganisms introduced into a mammal's oral, nasal, or pharyngeal cavity through the mammals hand-to-mouth or hand-to-nose contact. The method includes identifying a contact with a contaminated item by a hand of the mammal, wherein the contaminated item or environment is known, or expected to be, contaminated with harmful viral, fungal, or bacterial microorganisms. This may include contact with the contaminated items or environment listed above.

After such a contact is identified, the hand or both hands that had the contact with the contaminated item may be considered to be contaminated. At this point the barrier composition is administered in a therapeutically effective amount to an oral, nasal, or pharyngeal mucosa of a mammal prior to the mammal's hand-to-mouth or hand-to-nose contact. The barrier-forming composition then provides a barrier on the mucosa that inhibits the microorganisms from contacting the mucosa, and neutralizes or kills the microorganisms.

In an embodiment that illustrates a proposed mechanism of the barrier-forming composition, shown in FIG. 1, the barrier-forming composition provides anti-viral activity. When a virus comes into contact with a cell, it will bind to receptor on the host cell. Over time, 5 to 6 hours, or so, the virus is internalized by the host cell, the virus multiplies inside the host cell, and it induces cell lysis causing additional virus particles to infect other host cells.

In contrast, in a cell treated with the barrier-forming composition, a protective barrier is on the surface of the host cell. The barrier, which is thick enough to cover the cell and any receptors on the cell, prevents the virus particle from binding to the cell receptors. Thus, infection and lysis is also prevented. The barrier-forming composition retains the barrier for a long duration, such as a duration of about 2 hours or more, a duration of about 6 hours or more, a duration of about 16 hours or more, a duration of about 16 hours to about 24 hours, or a duration of about 24 hours or more, thereby protecting host cells and preventing infection. The antimicrobial activity is also retained for a long duration, such as about 2 hours or more, about 6 hours or more, or up to about 24 hours or more, thereby protecting host cells and preventing infection.

Without being bound by theory, the same mechanism described above and depicted in FIG. 1 is applicable to the anti-bacterial, and anti-fungal activity of the composition and method of prevention described herein.

In an embodiment the barrier-forming composition includes a combination of: a carbohydrate gum, a humectant; and an antimicrobial agent. In an embodiment, the composition meets the following requirements (where C is the carbohydrate gum; H is the humectant; and A is the antimicrobial agent):

about 0.01%≤C≤about 0.4%;
about 4.5%≤H≤about 65%; and
0.050%<A
or
about 0%≤C≤about 0.4%;
about 55%≤H≤about 65%; and
0.050%<A All percentages are by weight of the total composition.

In an embodiment, the barrier-forming composition includes glycerin or one or more similar humectant substances. The concentration of the humectant may range from about 2% to about 70% weight percent of the entire composition, such as, for example, about 4.5% to about 65%, about 7% to about 35%, or about 15% to about 45%. Humectants similar to glycerin may be classified generally as polyols. The humectants may be, for example, glycerin, sorbitol, xylitol, propylene glycol, polyethylene glycol, and mixtures thereof. In an embodiment, glycerin may be used at high concentrations such as about 55 to about 65% in the absence of a gum.

In an embodiment, the composition also includes a gum. The gum may be, for example, a polysaccharide, xanthan gum, gum Arabic, or guar gum. Such gums may be generally classified as carbohydrate gums that have an overall negative charge. In another embodiment, the gum may be, for example, xanthan gum, guar gum, gum Arabic, tragacanth, gum karaya, locust bean gum, carob gum, and pectin. These gums may also be generally classified as carbohydrate gums that have an overall negative charge. The gum may be present in a weight percentage of the total composition ranging from about 0.01% to about 0.4%, such as for example, about 0.25% to about 0.35%, about 0.05% to about 0.25%, or about 0.4%.

In an embodiment, an antimicrobial agent is present in the composition. For example, the composition may include one or more anti-viral agents, or antifungals. In addition, the effect of such antimicrobials includes static and/or cidal activity.

The antimicrobial agent may include, but is not limited to cationic antimicrobial agents and pharmaceutically acceptable salts thereof, including, for example, monoquaternary ammonium compounds (QAC, cetrimide, benzalkonium chloride, cetalkonium chloride, cetylpyridinium chloride, myristalkonium chloride, Polycide), biquaternaries and bis-biguanides (Chlorhexidine, Barquat, hibitane), and biguanides, polymeric biguanides, polyhexamethylene biguanides, Vantocil, Cosmocil, diamidines, halogen-releasing agents including chlorine- and iodine-based compounds, silver and antimicrobial compounds of silver, peracetic acid (PAA), silver sulfadiazine, phenols, bisphenols, hydrogen peroxide, hexachloroprene, halophenols, including but not limited to chloroxylenol (4-chloro-3,5-dimethylphenol; p-chloro-m-xylenol).

In addition, the antimicrobial may also be or include: antibacterial agents, both cidal and static, and different classes, for example tetracycline, chloramphenicol, fusidic acid, fluoroquinolone, macrolide antibacterial agents, oxazolidinones, quinolone- and naphthyridone-carboxylic acid, citral, trimethoprim and sulfamethoxazole (singly and combined), aminoglycoside, polymyxin, penicillins and their derivatives. In addition, the antimicrobial may also include, for example: antifungal agents in the following classes: azoles, polyenes, echinocandins, and pyrimidines. Combinations of the any of the foregoing antimicrobial agents are also contemplated. Many of the foregoing are cationic species or their pharmaceutically acceptable salts, and in an embodiment, cationic antimicrobials are utilized in the composition.

The antimicrobial may be present, for example, in an amount ranging from about 0.05% to 0.1% by weight of the total composition, such as, for example, about 0.05% to about 0.6% or about 0.6% to about 0.1%. In an embodiment, the antimicrobial is about 5% or less, or about 3% or less, or about 1% or less, such as when the antimicrobial used does not cause solubility problems at higher concentrations.

In embodiments, the composition may further include other components, such as, for example, copovidone and other lubricating agents, parabens such as methyl paraben or propylparaben, flavoring agents, preservatives, such as sodium benzoate, buffering agents, such as monosodium and disodium phosphate, and carboxymethylcellulose. These components may, for example, be included in amounts ranging from about 0.01% to about 5% by weight of the total composition, such as, for example, about 0.1% to about 2%. Flavoring agents may also be used. Buffering agents (such as monosodium or disodium phosphate) may be used to tailor the composition to the pH of the body cavity treated Purified water may be used as the diluent component of the composition.

In an embodiment, the composition can also function to create a retained benefit through the inclusion of additional components providing additional beneficial activity, such as, for example, probiotics, antacids, vitamins, drugs, nutraceuticals, silver, natural or synthetic small molecules, anti-oxidants, or immunostimulators, and combinations thereof. In an embodiment, silver may be used as the antimicrobial.

Some antimicrobials, including cetyl pyridinium chloride, are known to be negatively affected in their antimicrobial properties by additional active components. Thus, in an embodiment, the composition consists essentially of the gum, the humectant, and the antimicrobial. In an embodiment, the composition is exclusive of agents for acting against the teeth and/or gums, including, for example, teeth whitening or desensitizing agents. In an embodiment, the composition is also exclusive of cellooligosaccharides. In an embodiment, the composition is exclusive of one or more of time-release agents, allergy-relief compounds, azelastine, silicon based oils, essential oils, polyvinyl pyrrolidone, and potassium nitrate. For the avoidance of doubt, none of the above should be construed to mean that all embodiments are exclusive of these compounds.

In general, the dual-action mechanism of providing a barrier from microorganisms to the mucosa and an antimicrobial agent provides a long-lasting effect, characterized by both in vitro. Simulated in vivo, and in vivo examples below. In in vivo examples the barrier-forming composition was shown to have antimicrobial effect (cidal or static) for at least 6 hours, while the barrier property was not tested in actual human tests, simulated in vivo tests (on artificial human mucosa EHOMs) indicated the barrier itself had a significantly extended duration past 6 hours, such as greater than about 8 hours, about 6 to about 16 hours, and about 24 hours, or more. In addition, in vitro tests indicate the antimicrobial effect had a significantly extended duration past 6 hours, depending on the microorganism tested, such as greater than about 8 hours, about 6 to about 16 hours, or about 24 hours, or more.

Post antimicrobial effect (PAE) is defined as suppression of microbial growth that persists after limited exposure to an antimicrobial agent. Having a longer PAE is considered advantageous for antimicrobial agents as it allows for persistent inhibition of microbial growth, and may affect dosing regimens as agents with long PAEs may need less frequent administration than those with short PAEs.

In embodiments of the method and composition disclosed herein the PAE of the composition when applied to a mucosa has a PAE that persists for about 6 hours or more, such as about 6 hours to about 16 hours, or about 16 hours to about 24 hours.

In an embodiment, the composition has a Weybridge viscosity of about 16 to about 20 cps, such as, for example, about 17 to about 19 cps.

In an embodiment, at least a portion of the composition is ingested and is safe for human consumption in the therapeutically effective dosage.

It should be noted that not all mucosa in the treated cavity (e.g. oral, nasal, pharyngeal, or other) need to be covered with the barrier-forming composition, in order for the composition and method to be effective. In such a case, the composition and method are still effective to reduce microbial load in the cavity. Without being bound to theory, due to the trapping and killing dual-action mechanism, the barrier-forming composition will trap and kill microbes that otherwise would pass over the composition to reach any uncovered portions of the cavity in which the composition is applied. That said, the applied composition should be effective to cover a substantial percentage of the mucosal surface in the treated cavity, such as, for example, about 50% or more of the cavity, such as about 75% or more, or about 90% or more.

Without being bound by theory, the barrier-forming composition is not hydrophilic which allows the barrier-forming composition to have a greater affinity to adhere to and cover the mucosal surface. Furthermore, in an embodiment, the antimicrobial being embedded in the non-hydrophilic composition will allow for sustained antimicrobial activity in the mucosal environment. In an embodiment the barrier-forming composition is amphiphilic or has amphiphilic components.

One measure of hydrophilicity is the Rf (relative front) value, determined by chromatography in water. In an embodiment, the composition has an Rf value in water of 0 to about 0.25, such as about 0.0001 to about 0.15, or about 0.03 to about 0.1.

In an embodiment, the composition has a pH of about 4 to about 8, such as about 5 to about 7, or about 6 to about 7.5. The pH can be tailored to be compatible with the mucosa to be treated.

As the Examples below show, the barrier-forming composition has been shown to block the passage of a wide variety of representative bacteria and viruses. Because viruses are amongst the smallest infectious microorganisms, and because the barrier-forming composition forms a mechanical barrier blocking viruses from the mucosal cells, it is expected that the barrier-forming composition would be an effective preventative treatment not only for viruses but also for larger microorganisms, including a wide range of bacteria and fungi.

Several experiments were performed to assess the safety of the composition on mammals and the ability of the spray formulation to form a protective barrier on an Engineered Human Oral Mucosa (EHOM) model. The experimental evidence showed that the composition formed a barrier over tissues, which prevents microorganisms from penetrating into the tissues

EXAMPLES

Example 1

Human gingival epithelial cell and fibroblast cultures

Normal human gingival cells (epithelial cells and fibroblasts) were obtained from ScienCell Research Laboratories (Carlsbad, Calif., USA). The fibroblasts were cultured in Dulbecco's modified Eagle's medium (DME, Invitrogen Life Technologies, Burlington, ON, Canada) supplemented with fetal bovine serum (FBS, Gibco, Burlington, ON, Canada) to a final concentration of 10%. The epithelial cells were cultured in Dulbecco's modified Eagle's (DME)-Ham's F12 (3:1) (DMEH) with 5 μg/mL of human transferrin, 2 nM 3,3',5' of tri-iodo-L-thyronine.

0.4 μg/mL of hydrocortisone, 10 ng/mL of epidermal growth factor, penicillin and streptomycin, and 10% FBS (final concentration). The medium was changed once a day for epithelial cells and three times a week for fibroblasts. When the cultures reached 90% confluency, the cells were detached from the flasks using a 0.05% trypsin-0.1% ethylenediaminetetra acetic acid (EDTA) solution, washed twice, and resuspended in DMEM (for the fibroblasts) or DMEH-supplemented medium (for the epithelial cells).

Example 2

Engineered human oral mucosa (EHOM) tissue

The EHOM model was produced by using the gingival fibroblasts and epithelial cells of Example 1 that were used to form a complex three-dimensional spatial cellular organization similar to that found in normal human oral mucosa. The lamina propria was produced by mixing Type I collagen (Gibco-Invitrogen, Burlington, ON, Canada) with gingival fibroblasts, followed by culture in 10% FBS-supplemented medium for four days. The lamina propria was then seeded with gingival epithelial cells to obtain the EHOM. The tissue specimens were grown under submerged conditions until the total surface of the lamina propria was covered with epithelial cells. To produce stratified epithelium, the EHOM was raised to an air-liquid interface for four more days to facilitate the organization of the epithelium into its different strata.

Figure 2:
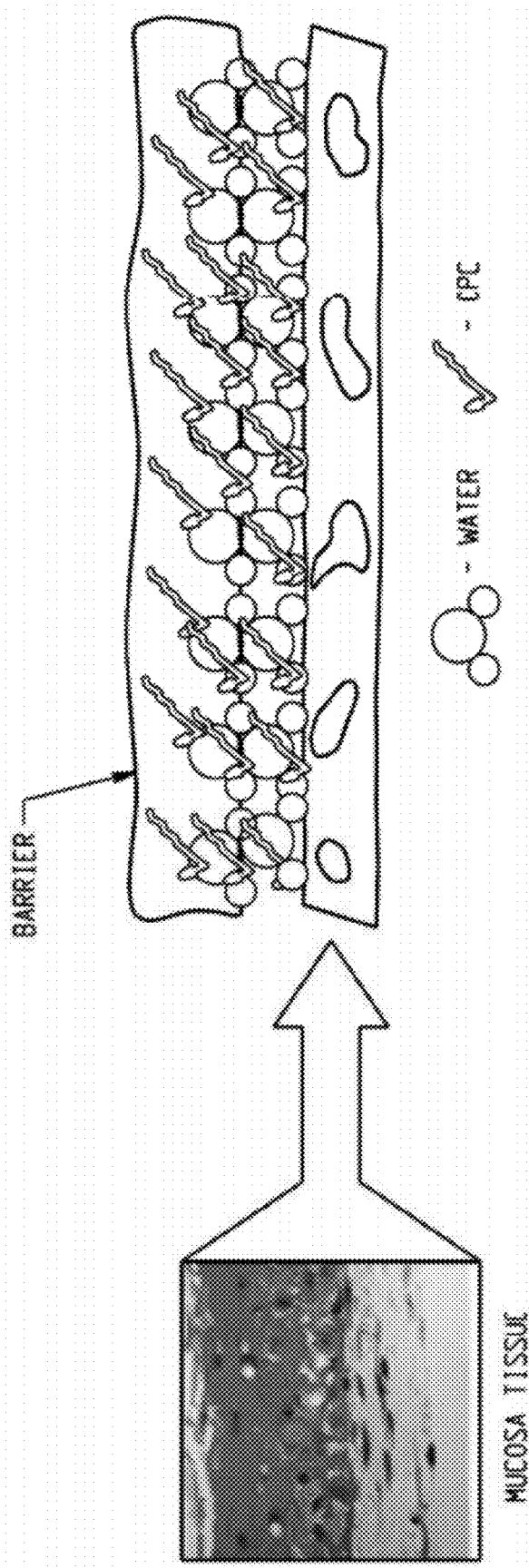
FIG. 2 is a schematic showing the formation of a barrier on a mucosal surface, as described in Example 2.

The lamina propria is a thin layer of loose connective tissue that lies beneath the epithelium and together with the epithelium constitutes the mucosa. FIG. 2 shows an illustration of the EHOM mucosal tissue, with an arrow pointing to its location in a schema depicting mucosa covered with the barrier-forming composition.

Examples 3-9

Examples of the barrier-forming compositions were created by adding the ingredients listed below in a 50-mL centrifuge tube, and vortexing to bring to "free-flow" consistency. The constituents of the compositions and their approximate amounts are given in Table I (the values in Table I are percentages by weight of the total composition):

Based on the results below, the preservatives were found to be superfluous to the barrier formation and antimicrobial activity.

Example 10

Monolayer wound repair assay

Wound repair assays were performed on the epithelial cells and fibroblasts of Example 1. Briefly, gingival epithelial cells ($1 \times 10^4$ cells) and fibroblasts ($1 \times 10^3$ cells) were seeded into wells of 6-well plates and grown in Dulbecco's modified Eagle's (DME)-Ham's F12 (3:1) (DMEH) with 5 μg/mL of human transferrin, 2 nM 3,3',5' of tri-iodo-L-thyronine, 0.4 μg/mL of hydrocortisone, 10 ng/mL of epidermal growth factor, penicillin and streptomycin, and 10% FBS (final concentration). Upon confluency, wounds were made in the confluent monolayer of each well using a 200 μL pipette tip.

Examples 11-15

In Examples 11 and 12, the epithelial cell cultures from Example 10 were exposed to diluted barrier-forming compositions of Examples 3 and 4 for about 2 minutes. In Examples 13 and 14, the fibroblast cultures from Example 10 were exposed to diluted barrier-forming compositions of Examples 3 and 4 for about 2 minutes. Prior to exposure, Example 3 was diluted with saline to a 1% concentration and Example 4 was diluted with saline to a 5% concentration. Following exposure, the spray was washed out twice with warm sterile culture medium, then cell cultures were over layered with DME for fibroblasts and DMEH for epithelial cells, and cultured for 6 and 24 hours in a 5% $CO_2$ humid atmosphere at 37° C. Control Example 15, which was an untreated culture from Example 10, was also tested.

Wound repair/cell migration was ascertained using an optical microscope, and digital photographs were taken (Nikon, Coolpix 950). The percentages of wound closure (cell growth/migration) were calculated by comparing relative wound areas before and after exposure to our barrier spray using formula I:

$$\frac{\text{(initial scratch size)} - \text{(size after a specified culture period)}}{\text{value of the (initial scratch size)} \times 100}. \quad \text{I}$$

Figure 3:
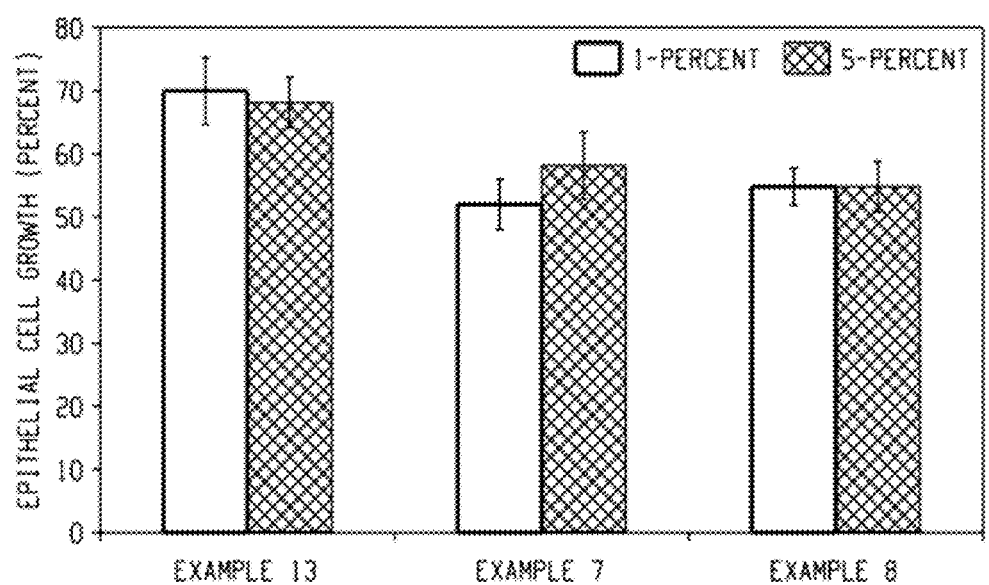
FIG. 3 is a graph showing the repair process as a percentage on a wounded epithelial cell sample through cell growth and migration after 6 hours to cover the scratched space in each of Examples 11-15.
Figure 4:
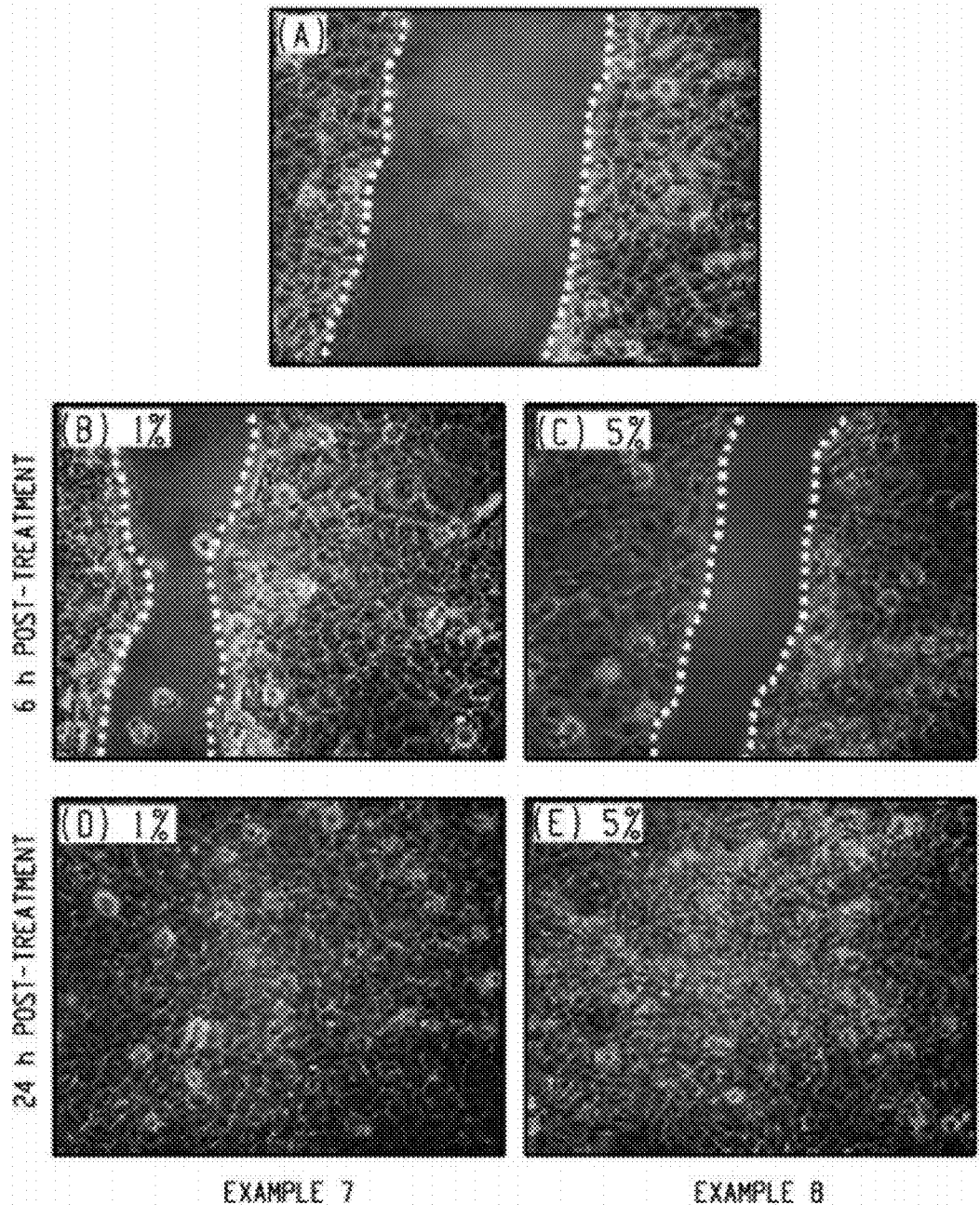
FIG. 4 shows microscopic photographs showing epithelial cell growth and migration on both untreated control Example 15 and treated Examples 16 and 17 on a wounded epithelial sample.

FIG. 3 shows a graph of the wound repair data generated from formula I after 6 hours post-treatment. FIG. 4 also shows photographs indicating the wound repair of the epithelial cells cultures treated with the 1% diluted barrier-forming composition and the control Example 15.

Following contact with the barrier-forming compositions, epithelial cells (FIG. 4A) and fibroblasts (data not shown) migrated progressively starting at 6 hours post contact with the barrier-forming compositions of Examples 11 and 12. Epithelial cells were small and cuboidal in shape, in both non-exposed and barrier-forming composition-exposed cul-

TABLE II

|  | Example 3 | Example 4 | Example 5 (control) | Example 6 (control) | Example 7 | Example 8 | Example 9 |
|---|---|---|---|---|---|---|---|
| Glycerin | 7 | 35 | 35 | 35 | 35 | 7 | 7 |
| Xanthan Gum | 0.01 | 0.4 | 0.4 | 0.4 | 0.4 | 0.01 | 0.01 |
| Cetyl Pyridinium Chloride | 0.05 | 0.05 |  |  | 0.1 | 0.06 | 0.05 |
| Preservatives | No | No | No | Yes | Yes | Yes | Yes |

*Purified water comprised the remaining portion of the composition.
**Preservatives included methylparaben (0.1%), propylparaben (0.1%), sodium benzoate (0.5%)

tures (FIG. 4A-E). Fibroblasts were elongated cells with small nucleus in both culture conditions (unexposed and cetylpyridinium chloride-based products exposed cells) (data not shown). Cell growth and migration to cover the wounded zone were comparable in both the control Example 15 and the treated Examples 11 and 12 as compared to the original wound (FIG. 4F). Follow up over 24 hours showed that each of Examples 11 and 12 covered the edges of the scratch giving confluent monolayers (FIG. 4D-E).

This experiment was repeated five separate times with similar results. The treated Examples 11 and 12 did not show a major side effect on gingival epithelial cells growth/migration nor on cells differentiation (no cells presenting large cytoplasm and large nucleus).

Examples 16-19

Cytotoxicity assay

The engineered human oral mucosa (EHOM) model of Example 2 was used to determine whether the composition of Examples 10 and 11 were safe and did not promote tissue damage or cell necrosis. In Example 16 and 17, the epithelium surface (10 cm$^2$) was over layered with a thin layer (300 µl) of the Example 3 barrier-forming composition at a dilution of 5% and the Example 4 composition at a dilution of 1% (both were diluted in serum free culture medium) for time periods of about 2 minutes. The variation in time period was not deemed to have an effect on the results and just reflects the time it took to conduct the procedures. Control Example 18 was a control that was not treated with the barrier-forming composition. The EHOM tissues were then rinsed twice with warm sterile culture medium and incubated in a 5% $CO_2$ humid atmosphere at 37° C. for 24 hours. Following this incubation period, to assess whether the engineered tissue was damaged, each EHOM was macroscopically examined for the presence of holes due to the contact with the barrier spray formulation. Photos were taken of these EHOM to confirm such possibility. Additionally, biopsies were collected from each EHOM and subjected to histological staining using eosin and hematoxylin.

In Examples 16 and 17, EHOM exposed to Examples 3 and 4 in the 1 and 5% dilutions, similar to untreated control Example 18, do not show any macroscopic damage such as holes. (See FIG. 5). The absence of such damage was monitored after 10 minute tissue contact with 5% dilution Example 3 mouthwash (Example 7A) and 1% dilution spray (Example 7B) compositions. This was confirmed by histological analyses showing multilayer organisation of the epithelium on the top of a fibroblast-populated connective tissue. No specific damage was observed in EHOM tissues in Examples 16 or 17. The Example 16 and 17 treated-EHOM structures were comparable to the untreated control Example 18.

The same observation was noted in an Example 19, which was the same as Example 16, except it included an EHOM treated with a 1% dilution (data not shown).

Figure 5:
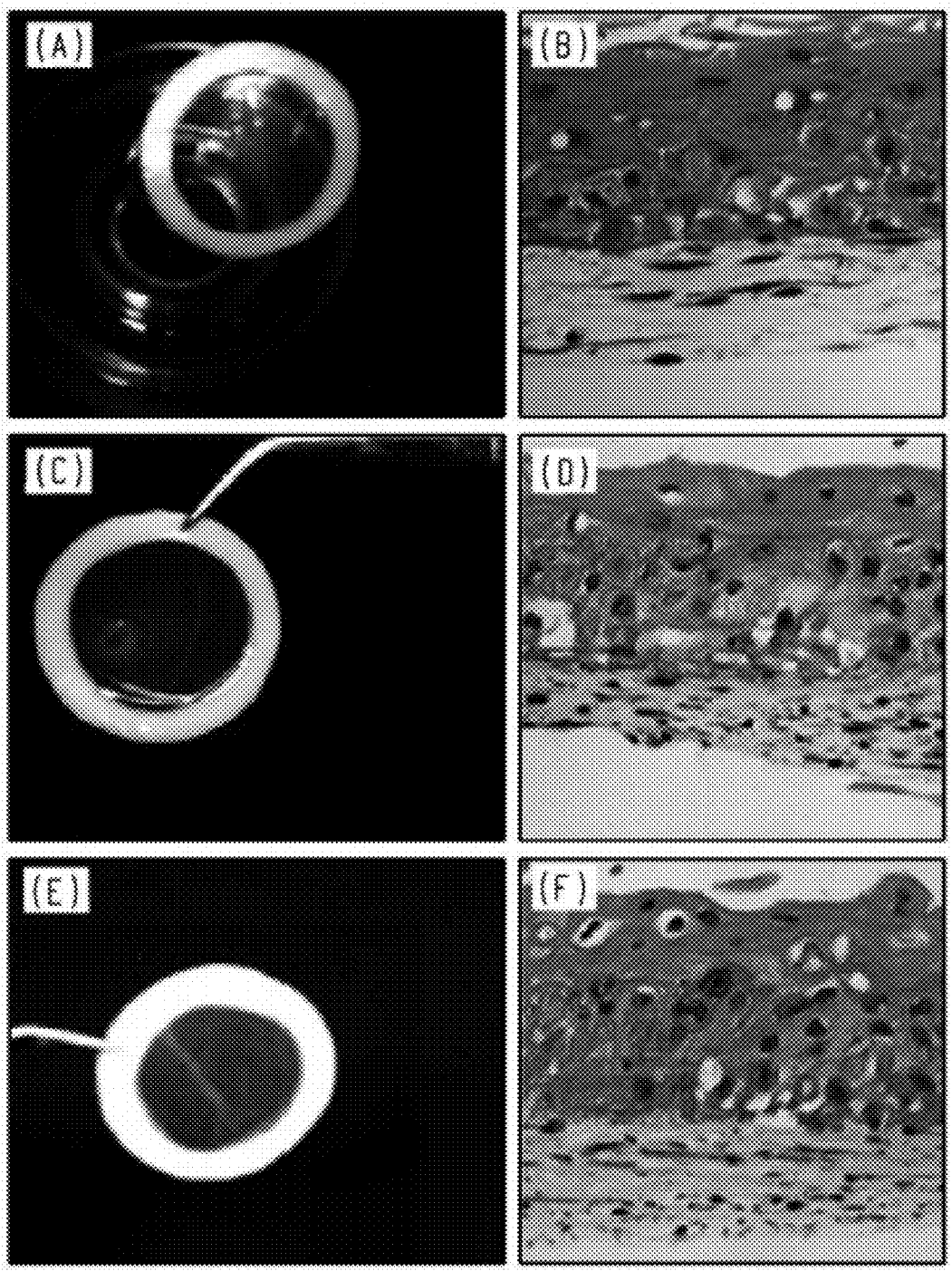
FIG. 5 shows photos of magnified cross-sections of the barrier-forming composition-treated and untreated engineered human oral mucosa (EHOM) of Examples 11-15.

FIG. 5 shows the effect of the barrier-forming composition on EHOM macroscopic shape and structure. Panels A and B show control Example 18. Panels C and D show Example 16 (spray composition) and panels E and F show Example 17 (mouthwash composition).

Examples 20-25

Side effects, if any, of the barrier spray composition on EHOM injury was also assessed by measuring the leakage of intracellular LDH into the culture medium.

In Examples 20-23, EHOM tissues were exposed to (A) 1% or (B) 5% dilutions of Examples 3 and 4, respectively, for 10 minutes, followed by growth in culture medium for 24 hours. Examples 24 and 25 were controls that were not treated. 50 µl of a supernatant of each of Examples 20-25 were then transferred to a sterile 96-well flat-bottom plate. Each well was supplemented with 50 µl of reconstituted substrate mix, and the plate was incubated for 30 min at room temperature in the dark. To estimate LDH levels, aliquots of the culture supernatant were collected and subjected to an LDH cytotoxicity assay (Promega, Madison, Wis., USA), as per the manufacturer's protocol. This assay measures the conversion of L-lactate and NAD to pyruvate and NADH by the released LDH. To stop the reaction, 50 µl of stop solution was added to each well. Next 100 µl of the mixture were transferred to a 96-well flat-bottom plate, and the absorbance was read at 490 nm with an X-Mark microplate spectrophotometer (Bio-Rad, Mississauga, ON, Canada).

In the LDH and wound repair experiments, the following test methods were used. Each experiment was performed at least four times, with experimental values expressed as means±SD. The statistical significance of the differences between the control (absence of barrier spray) and the test (presence of spray) values was determined by one-way ANOVA. Posteriori comparisons were done using Tukey's method. Normality and variance assumptions were verified using the Shapiro-Wilk test and the Brown and Forsythe test, respectively. All of the assumptions were fulfilled. P values were declared significant at ≤0.05. Data were analyzed using the SAS statistical package (version 8.2, SAS Institute Inc., Cary, N.C., USA).

Figure 6:
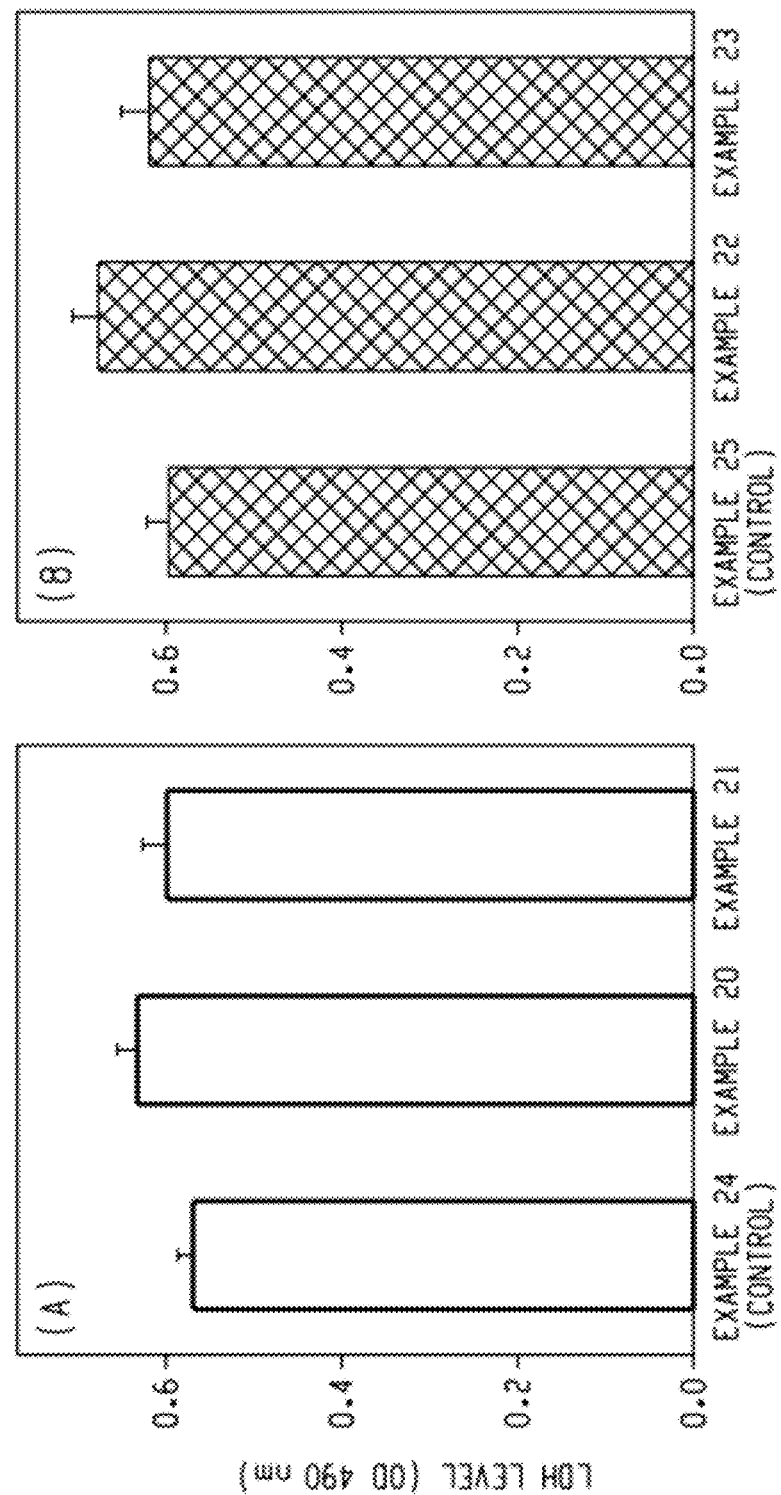
FIG. 6 is graph showing an LDH assay of Examples 16-19 and 20-25.

Results presented in FIG. 6 showed no significant difference in LDH levels in barrier-forming composition treated structures as compared to untreated tissues. These observations were made at 6 hours (data not shown) and 24 hours (FIG. 6) post-exposure to the barrier-forming composition treated Examples. FIG. 6(A) shows Control Example 24 and the 1% dilution treated Examples 20 and 21; and FIG. 6(B) shows a Control Example 25, and the 5% dilution treated Examples 22 and 23. This data confirm the non-toxic effect of Examples 3 and 4. Similarly, contact for 2 minutes with Examples 3 and 4 did not show any difference as compared to the controls (data not shown).

Example 26

Determination whether Barrier-forming composition Damages EHOM Structure

EHOMs of Example 2 were treated with Example 4 for about 2 minutes, washed with culture medium then cultured for 24 hours. Tissue was then examined for possible macroscopic tissue damage (presence or not of holes). Tissue damage was also investigated by histological analyses. For this purpose, biopsies were taken from each EHOM. They were fixed with 4% paraformaldehyde solution and then embedded in paraffin. Thin sections (4 µm) were stained with eosin-hematoxilyn. Sections were mounted with a coverslip in 50%-glycerol mounting medium, observed through an optical microscope, and photographed. No damage to the treated EHOMs was ascertained.

Examples 27 and 28

Determination Whether the Barrier-forming composition Affects Mechanical Barrier Function of EHOM Against Microbial Passage Through Mucosal Tissue In Examples 27 and 28, two approaches were used to determine whether the control Examples formed a barrier that blocked the microbial passage through the mucosal tissues and also had an inherent anti-microbial effect. Growth in pass-through chamber and growth on EHOM surface was assessed by evaluating growth in agar media.

In Example 27, EHOMs of Example 2 were put in contact with 1 and 5% dilutions (diluted in serum free culture medium) of Example 4 for 2 minutes. Tissues were then washed twice with serum free culture medium then over layered with $1 \times 10^6$ candida microbial cells in a volume of 300 μl. Tissues were then put on air-liquid culture plates and incubated for 24 hours in 5% $CO_2$ humid atmosphere at 37° C. Next, the culture medium underneath the EHOM (ventral chamber) was collected and seeded on Sabouraud agar plate to verify whether or not the microorganisms penetrated through the tissue and reached the culture medium below. A culture was also obtained from the EHOM surface and seeded on Sabouraud agar plate. The process is graphically depicted in FIG. 7.

In Example 28, EHOMs of Example 2 that were treated with 1 and 5% dilutions of the Example 4 composition for 2 minutes were over layered with candida microbial cells for 24 hours were flipped onto Sabouraud dextrose agar plates and left in place for 5 minutes. The EHOMs were then removed and the plates were incubated for 24 hours at 30° C., after which microbial growth was ascertained macroscopically and photographed. Each experiment was repeated 5 independent times with similar results.

Figure 8:
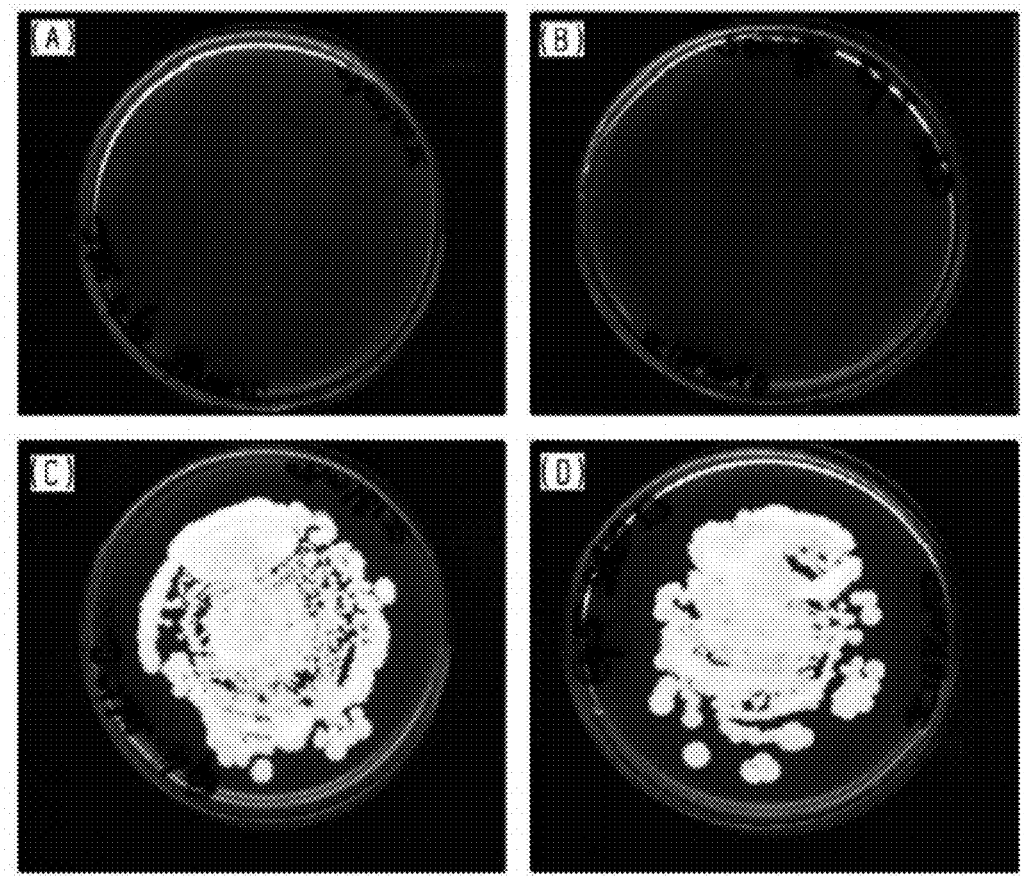
FIG. 8 show photographs of agar media plates showing microbial growth in the upper and lower chambers of an EHOM assay, as described in Examples 27-28.

FIG. 8 shows the results of the cultures of the EHOM surface (panels C and D) and the culture of the pass-through liquid from the bottom (ventral) chamber (panels A and B). The A and C panels were EHOMs treated with a 1% dilution of Example 4, and the B and D panels were EHOMS treated with a 5% dilution of Example 4. This data indicates that Example 4 composition forms a barrier that prevents passage of microbes through the EHOM tissues but does not have an inherent anti-microbial effect.

Examples 29 and 30

In Examples 29 and 30, Examples 27 and 28 were repeated, except the EHOM were infected with *S. mutans*. Similar results were obtained that indicated that the barrier-forming compositions formed a barrier preventing the *S. mutans* microbes from passing through the barrier, but did not have an antimicrobial effect.

Examples 31 and 32

Determination Whether the Barrier-forming composition Affects Mechanical Barrier Function of EHOM Against Microbial Invasion In Example 32, a set of EHOM tissues from Example 2 was treated with the barrier-forming composition of Example 4 and then overlaid with *C. albicans*. In control Example 31a control set was not treated with the barrier-forming composition prior to overlayering with *C. albicans*. Immediately after each contact period, biopsies were taken from each EHOM, fixed with paraformaldehyde solution, and embedded in paraffin. Thin sections (4 μm) were stained with eosin-hematoxylin. Sections were observed using an optical microscope to analyze the invasion/penetration of microbial cells into the tissue. Following microscopic observations, representative photos were taken from each condition and presented. The experiment was repeated three times with similar results. Similar results were also obtained with treatment with Example 3 (data not shown).

Figure 9:
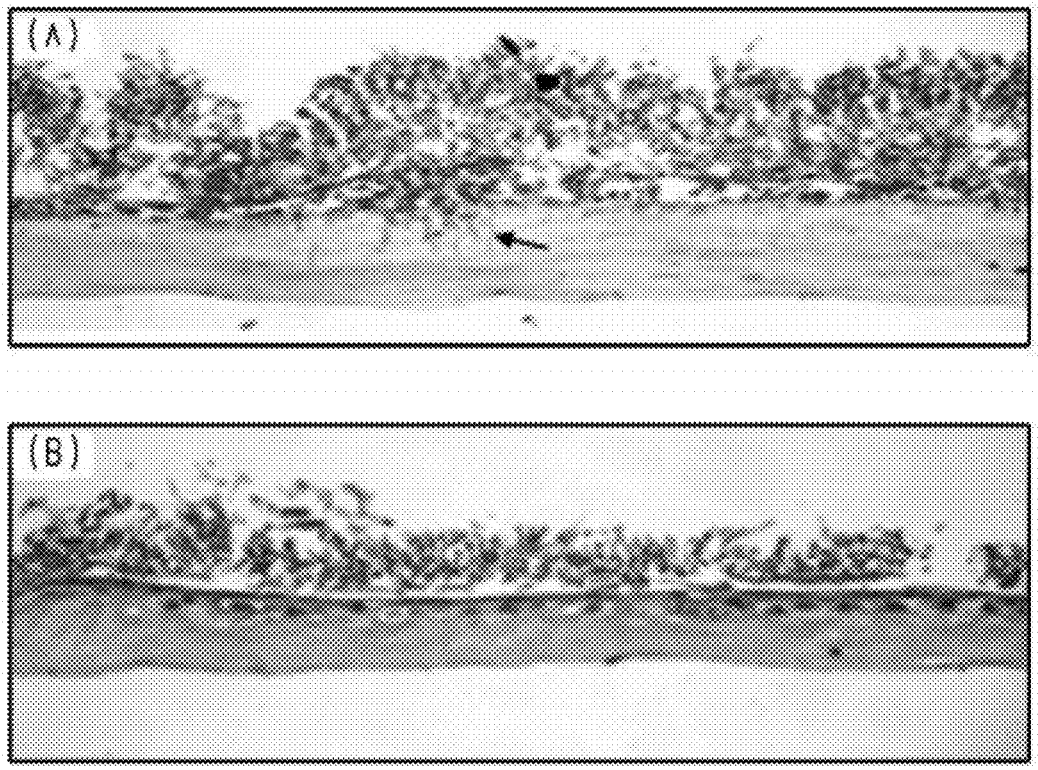
FIG. 9 shows photographs of magnified cross-sections of the barrier-forming composition-treated and untreated engineered human oral mucosa (EHOM) of Examples 31-32.

FIG. 9 shows the effect of the barrier-forming composition on microbial invasion of EHOM tissues. Panel (A) is a representative photograph of the untreated control Example 31, and panel (B) is a photograph of the treated Example 32. The arrow indicates invading fungal hyphae in the untreated control Example 31.

Examples 33-40

The EHOM model described above was also used to evaluate the ability of Examples 5-7 to form a barrier that: (a) prevents oral bacteria (*S. mutans*) and fungi (*Candida albicans*) from penetrating/invading human oral mucosa, and (b) does not cause damage to host cells (cytotoxicity assay).

Examples 33-40 were formulated according to Table III below.

TABLE III

| | Barrier-forming composition Pre-Treatment | Microbe Overlay | FIG. reference |
|---|---|---|---|
| Example 33 | None | *C. albicans* | FIG. 10(A) |
| Example 34 | Example 5 | *C. albicans* | FIG. 10(B) |
| Example 35 | Example 6 | *C. albicans* | FIG. 10(C) |
| Example 36 | Example 7 | C. albicans | FIG. 10(D) |
| Example 37 | None | *S. mutans* | FIG. 11(A) |
| Example 38 | Example 5 | *S. mutans* | FIG. 11(B) |
| Example 39 | Example 6 | *S. mutans* | FIG. 11(C) |
| Example 40 | Example 7 | *S. mutans* | FIG. 11(D) |

In Examples 33-40, after pre-treatment and incubation according to the procedures of Examples 27 and 28: (1) the flow-through medium was collected from the lower chamber; and (2) tissues were flipped and placed onto the surface of Sabouraud dextrose agar Petri dishes, and incubated for 24 hours. Collected flow-through media were spread onto agar media plates, and incubated for 24 hours also as described in Examples 27 and 28. Table III also indicates the Figure in which a photo of each Example was taken showing the microbial growth on each flipped Example culture.

Figure 10:
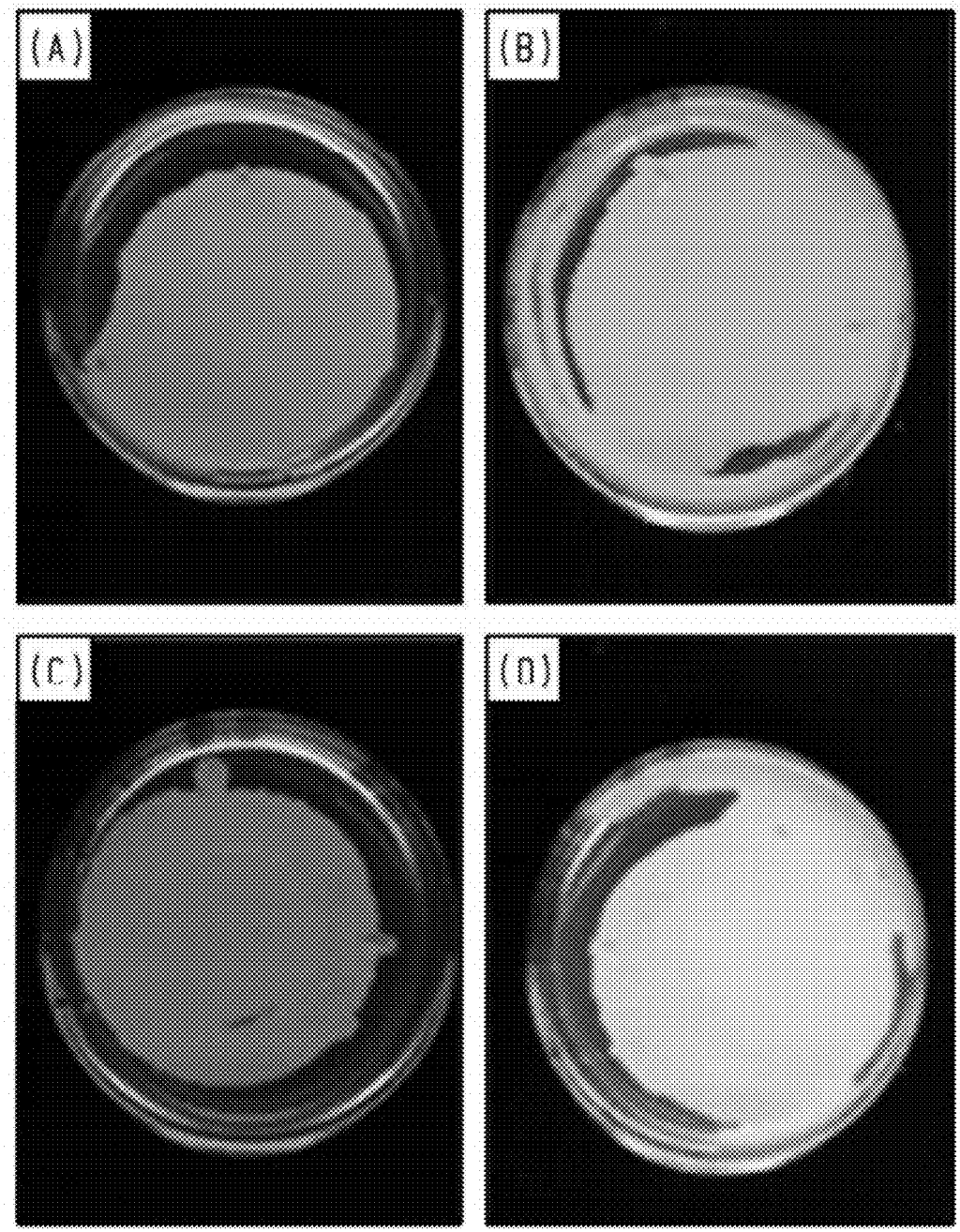
FIG. 10 shows photographs of microbial growth on untreated EHOM or EHOM treated with an example barrier-forming composition, followed by infection with *C. albicans*, as described in Examples 33-40.
Figure 11:
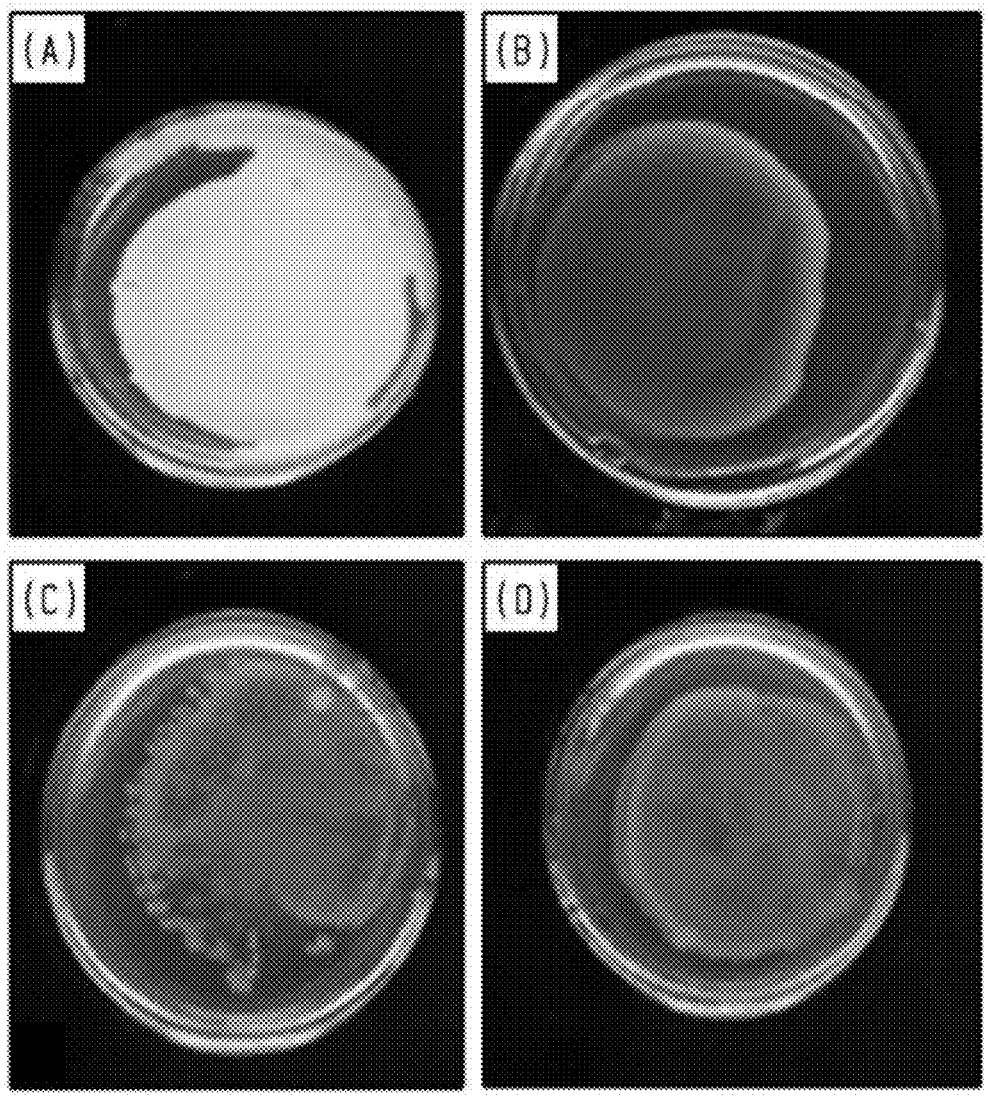
FIG. 11 shows photographs of microbial growth on untreated EHOM or EHOM treated with formulations followed by infection with *S. mutans*, as described in Examples 33-40.
Figure 12:
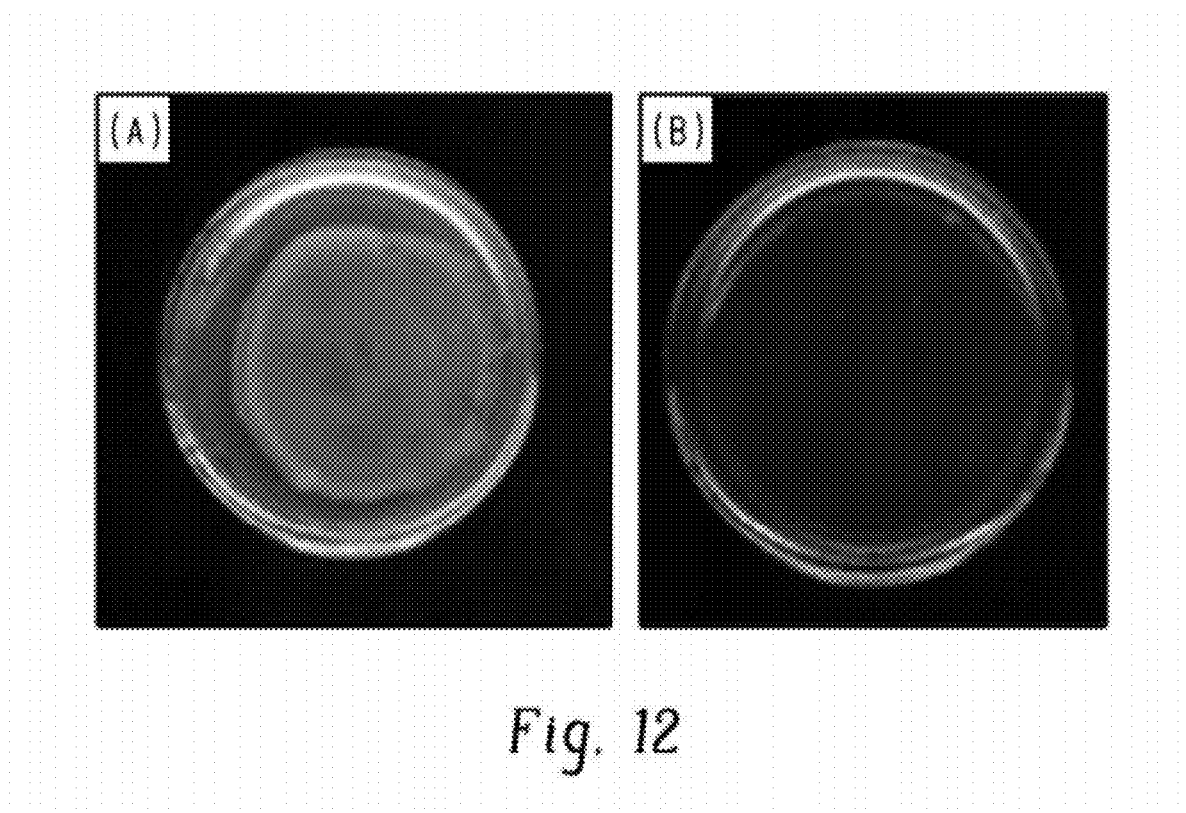
FIG. 12 shows photographs of microbial growth from "flow-through" media (collected from the lower chamber) of EHOM treated with an example barrier-forming composition, as described in Example 33-40.

FIGS. 10 and 11 show that both *Candida* and *Streptococcus* were able to grow on the surface of EHOM treated with the compositions of Examples 5-7. In contrast, as shown in FIG. 12, no microbial growth was observed when the "flow-through" medium collected from the lower chambers of EHOMs of Examples 36 or 40, i.e. those treated with the Example 7 composition This indicates that treatment of the EHOMs with the Example 7 composition did not cause damage to the surface of the mucosal tissues and organisms were unable to penetrate the treated EHOM. Similar results were obtained with EHOM treated with the compositions of Examples 5 and 6 (data not shown). These data indicate that the combination of glycerine and xanthan gum is capable of forming a protective barrier on mucosal tissues.

Examples 41-47

Tested Formulations are not Toxic and do not Cause Damage to the Cells/Tissues

In Examples 41-47, the EHOM model was used to assess the toxicity of the composition. Examples 41-47 were formulated as stated in Table IV.

TABLE IV

| | Barrier-forming composition Pre-Treatment | Microbe Overlay | FIG. Reference |
|---|---|---|---|
| Example 41 | None | *C. albicans* | FIG. 13(A) |
| Example 42 | Example 5 | *C. albicans* | FIG. 13(A) |
| Example 43 | Example 6 | *C. albicans* | FIG. 13(A) |
| Example 44 | Example 7 | *C. albicans* | FIG. 13(A) |
| Example 41A | None | *S. mutans* | FIG. 13(B) |
| Example 45 | Example 5 | *S. mutans* | FIG. 13(B) |

TABLE IV-continued

| | Barrier-forming composition Pre-Treatment | Microbe Overlay | FIG. Reference |
|---|---|---|---|
| Example 46 | Example 6 | S. mutans | FIG. 13(B) |
| Example 47 | Example 7 | S. mutans | FIG. 13(B) |

After pre-treatment and incubation according to the procedures of Examples 27 and 28, culture supernatant was collected from the Example 41-48 EHOM tissues and used to measure LDH activity.

Figure 13:
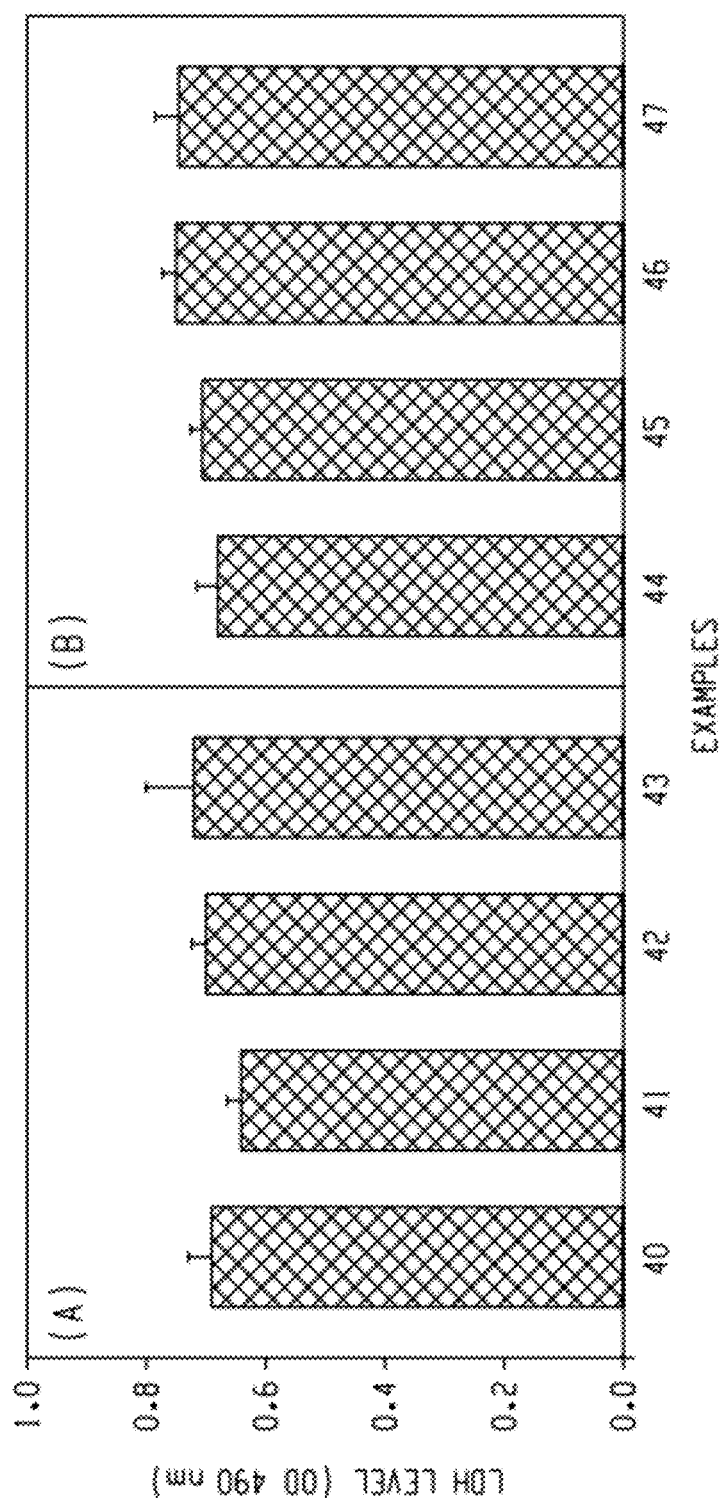
FIG. 13 presents graphs showing LDH release by EHOM treated with saline (control) or example barrier-forming compositions, followed by infection with (A) *C. albicans* or (B) *S. mutans*, as described in Examples 40-47.

As shown in FIG. 13, no significant increase in LDH levels was observed in Examples 41-48 irrespective of whether the formulations contained cetylpyridinium chloride with or without preservatives and infected with either Candida albicans or S. mutans, respectively. These data confirmed the non-toxic effect of the Example barrier-forming compositions and that these formulations maintained the integrity of the host mucosal tissues.

Data are mean±SD and were computed as stated in Example 25 above. No significant difference between untreated and treated tissues was noted.

Taken together, the data indicates that the example compositions represent an effective and a safe barrier that can prevent microorganisms from penetrating and invading human mucosal tissues.

Examples 48-61

Preclinical evaluation of the barrier-forming composition showed that the composition was effective against many bacteria and yeasts. The antimicrobial activities of the Example 7 barrier-forming composition were evaluated against a number of clinical isolates obtained from patients, including S. salivarius, P. gingivalis, S. pyogenes, S. pneumonia, Fusobacterium nucleatum, S. mutans, S. aureus, Y. enterocolitica, S. oxalis, S. mitis, C. albicans, C. krusei, C. tropicalis, and C. glabrata. Activity of the Example 7 barrier-forming composition was evaluated by determining its minimum inhibitory concentration (MIC) using reference methods described in the Clinical and Laboratory Standards Institute (CLSI) documents M07-A8, M11-A7, and M27-A3.

A standardized inoculum of several types of aerobic or anaerobic bacteria ($1\times10^4$ cells/ml) was incubated with serially diluted solutions of Example 7 (containing 0.1% CPC, or 1 µg/ml) or 2% chlorhexidine gluconate (CHX, 20 µg/mL) as a comparative example. Cells were allowed to grow in the presence or absence (growth control) of the test agents for 24 hours. The MIC for each agent was defined as the concentration that induced a 100% growth inhibition (compared to no-drug control).

A similar microdilution-based CLSI method (M27-A2) was used to evaluate the activity of Example 7 against albicans and non-albicans Candida species.

TABLE V

| | Organism | Example 7 (µg/mL CPC) | Chlorhexidine (µg/mL chlorhexidine) |
|---|---|---|---|
| Example 48 | S. salivarius | 0.98 | 19.6 |
| Example 49 | P. gingivalis | 0.98 | 19.6 |
| Example 50 | S. pyogenes | 0.98 | 19.6 |
| Example 51 | S. pneumonia | 0.98 | 19.6 |
| Example 52 | F. nucleatum | 1.95 | 19.6 |
| Example 53 | S. mutans | 1.95 | 19.6 |
| Example 54 | S. aureus | 3.91 | 19.6 |
| Example 55 | Y. enterocolitica | 3.91 | 19.6 |
| Example 56 | S. oralis | 500 | 19.6 |
| Example 57 | S. mitis | 500 | 19.6 |
| Example 58 | C. albicans | 0.25 | 19.6 |
| Example 59 | C. krusei | 0.06 | 19.6 |
| Example 60 | C. tropicalis | 0.06 | 19.6 |
| Example 61 | C. glabrata | 0.125 | 19.6 |

The barrier-forming composition was also found to have potent antimicrobial activity against: MRSA, Acinetobacter baumannii, Streptococcus sanguis, S. gordonii, and Aggregatibacter actinomycetemcomitans.

As can be seen in Table V, the Example 7 composition exhibited potent activity against many aerobic and anaerobic bacteria, as well as the fungi.

The MIC of the Example 7 barrier-forming composition against S. oralis and S. mitis was noticeably elevated (500 µg/mL) compared to other organisms. It is interesting to note that S. oralis and S. mitis are normal commensals of the oral cavity. Activity of the commonly used antimicrobial chlorhexidine (2% solution) was also determined by the same method. Table V shows the MIC of the Example 7 barrier-forming composition and chlorhexidine (2% solution) as a comparative example against various microorganisms.

Taken together, these results demonstrate that Example 7 possesses potent activity against pathogenic bacteria and fungi commonly isolated from the oral cavity. This activity was more potent than that observed for chlorhexidine.

A similar activity profile was observed for the barrier-forming compositions of Examples 10 and 11.

Example 62

As a further comparison, published data shows that the tested barrier-forming composition has a better or at least equivalent MIC compared to CPC alone (i.e. not in a composition according to the barrier formulation disclosed herein). See Frank-Albert Pitten and Axel Kramer, "Efficacy of Cetylpyridinium Chloride Used as Oropharyngeal Antiseptic," Arzneim.-Forsch./Drug Res. 51 (II), pp 588-595 (2001), which is incorporated herein by reference. The data varies based on the microorganism tested, but, for example, CPC (alone) against S. mutans has an MIC of 5.0-6.25 µg/mL, which is much less effective than the 1.95 µg/mL reported in Example 53. This was an unexpected result since CPC has the risk of losing its activity when mixed with other excipient chemicals in a formulation. See Department of Health and Human Services (Food and Drug Administration) (1994) Oral Health Care Drug Products for Over-the-Counter Human Use; Tentative Final Monograph for Oral Antiseptic Drug Products. Proposed Rules (21 CFR Part 356, Docket No. 81N-033A, RIN 0905-AA06). Federal Register 59:6084-124.

Examples 63-69

Duration of Antimicrobial Activity of Barrier-forming compositions in vitro: Determination of Post-Antimicrobial effect (PAE)

The PAE of Example 8 against several microorganisms was evaluated in Examples 63-68. Control Example 69 was also provided. Several microorganisms were exposed to Example 8 (at a concentration equal to the MIC) for 1 min followed by three washes to remove residual formulation. The treated cells were then spread on agar medium plates, which were incubated at 37° C., and the time taken for the cells to regrow was determined. PAE was expressed as the time (in hours) for which growth inhibition (%) was maintained by the Examples 63-68, compared to the untreated control Example 69.

Figure 14:
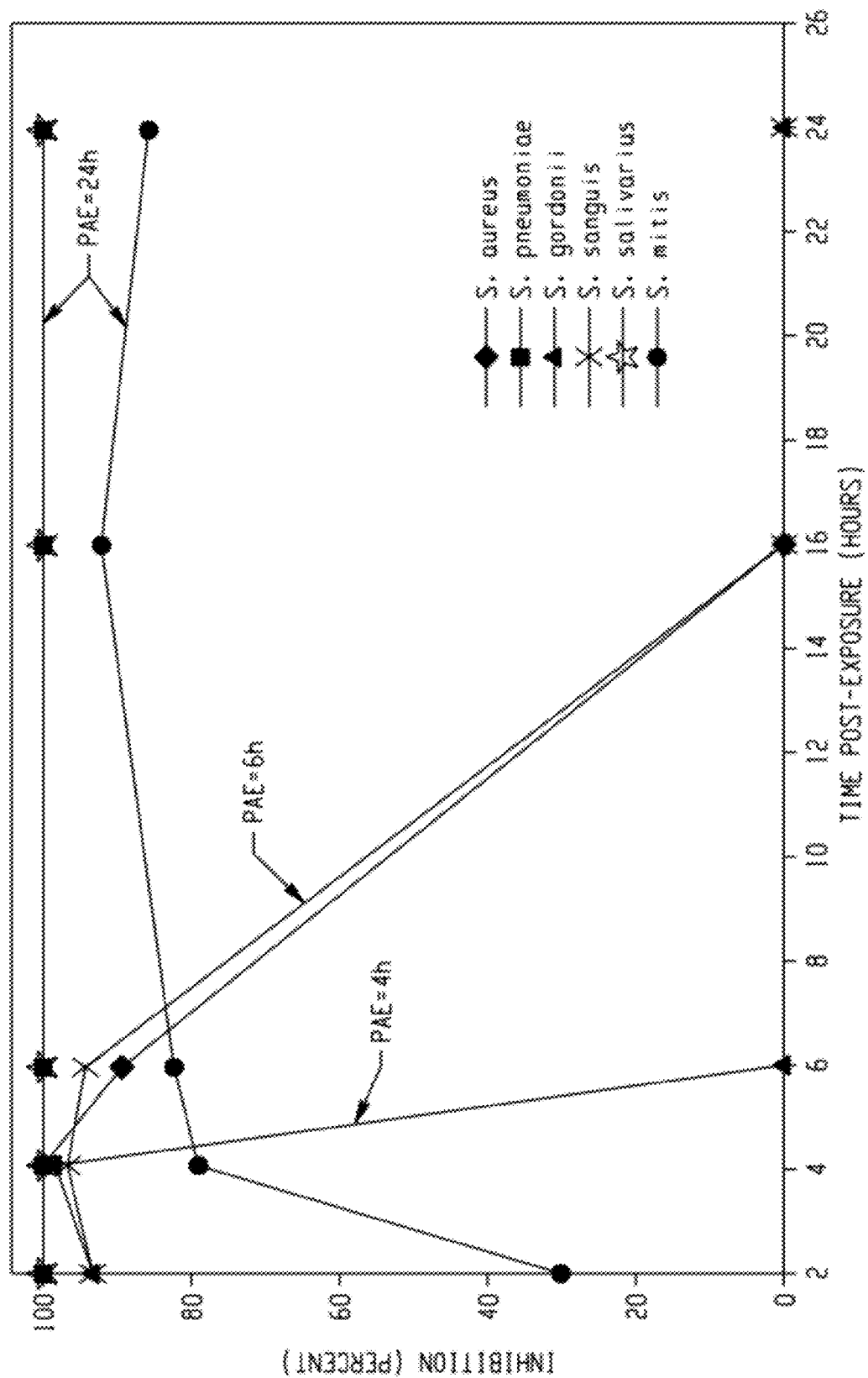
FIG. 14 is a graph showing post-antimicrobial effect of barrier-forming compositions against bacteria and fungi, as described in Examples 48-61 and 61-69.

As shown in FIG. 14, Example 8 exhibited a PAE ranging between 4 hours to 24 hours, depending on the organism tested (*S. aureus, S. pneumonia, S. gordonii, S. sanguis, S. salivarius,* and *S. mitis*). Similar activity of Example 8 was observed against *Candida* (data not shown). Other Example barrier-forming compositions exhibited similar PAE against microorganisms.

Example 70

Testing of PAE for the Example 7 barrier-forming composition against *S. mutans* compared to a similar comparative Example with lower CPC content showed that the PAE of Example 7 was 24 hours, while that of Comparative Example 70 was 6 hours. Thus demonstrating the Example 7 exhibits greater prolonged antimicrobial activity than comparative Example 70, and that additional amounts of CPC have more than a simple additive effect on anti-microbial activity.

Examples 71-76

Scanning electron microscopy was also used to show that treatment of *S. sanguis,* (Example 71), S. oxalis, (Example 72), and *C. albicans* (Example 73) with the composition of Example 3 resulted in destruction of cellular integrity.

In Examples 71-73, cells were grown in the presence of Example 3 for 24 hours. Next, the cells were washed to remove residual formulation, dehydrated by passing through a series of alcohol solutions (10% to 100%, v/v) and processed for SEM analysis. Control Examples 74-76 differed from Examples 71-73 in that they were not grown in the presence of Example 3.

Figure 15:
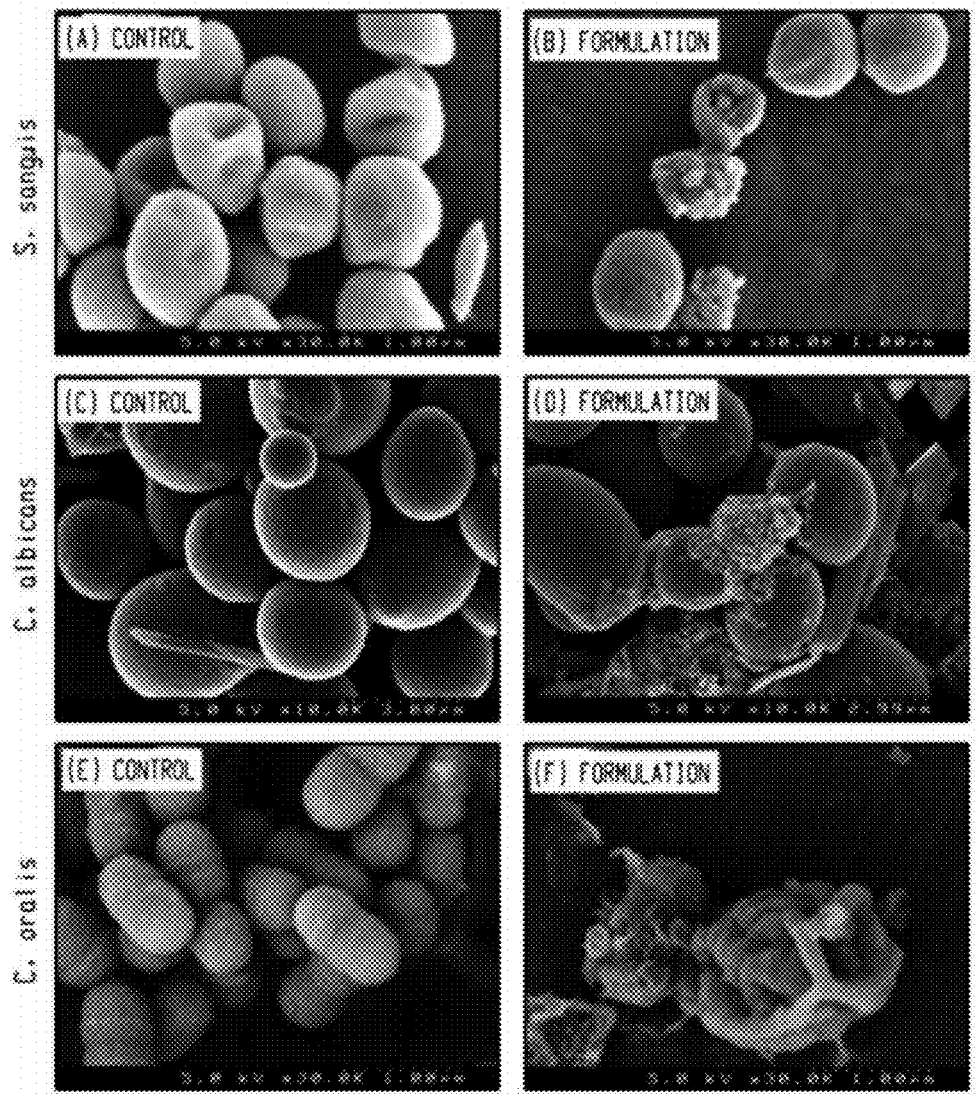
FIG. 15 shows scanning electron micrographs of *S. sanguis*, *C. albicans*, and *S. mutans*, untreated or treated with barrier-forming composition, as described in Examples 71-76.

The SEM photos showed that unlike untreated control Examples 74-76, which demonstrated healthy intact cells (FIG. 15 A, C, E), microbes exposed to the Example 3 barrier-forming composition were deformed, collapsed, and exhibited total destruction of cellular integrity with clear evidence of leakage of cytoplasmic material. (FIG. 15, B, D, F).

Examples 77-79

Since biofilms are precursors to certain infectious diseases, in Examples 77-79, experiments were performed to determine whether the barrier-forming compositions can prevent formation of biofilms by bacteria and yeasts. Biofilms were formed using an in vitro model. See Chandra et al. "In vitro Growth and Analysis of *Candida* Biofilms" Nature Protocols 3(12): 1909-1924 (2008).

In Examples 77-79 a standard biofilm model was employed to determine whether the Example 3 barrier-forming composition exhibits activity against bacterial and fungal biofilms. In Examples 77-79, three different microorganisms (*C. albicans, S. oralis,* and S. salivarius) were adhered on substrate for 90 minutes to allow biofilms to form to adhesion phase. Next, discs containing the adherent bacteria were incubated for 15, 30 or 60 minutes with 50% concentration of Example 3 (1:1 dilution with appropriate medium). Following incubation, biofilms were scraped, spread on culture media, incubated and colony forming units (CFUs) were determined. Media diluted with phosphate buffered saline (PBS, 1:1) were used as a control. Table VI reports data at 0 (Control), 15, 30, and 60 minutes.

TABLE VI

Effect of Barrier-forming composition on Early Phase Biofilms (log CFU)

| Exposure time | Example 77 C. albicans | Example 78 S. oralis | Example 79 S. salivarius |
|---|---|---|---|
| Control | 5.44 | 3.25 | 3.16 |
| 15 min | 0 | 0 | 0 |
| 30 min | 0 | 0 | 0 |
| 60 min | 0 | 0 | 0 |

Figure 16:
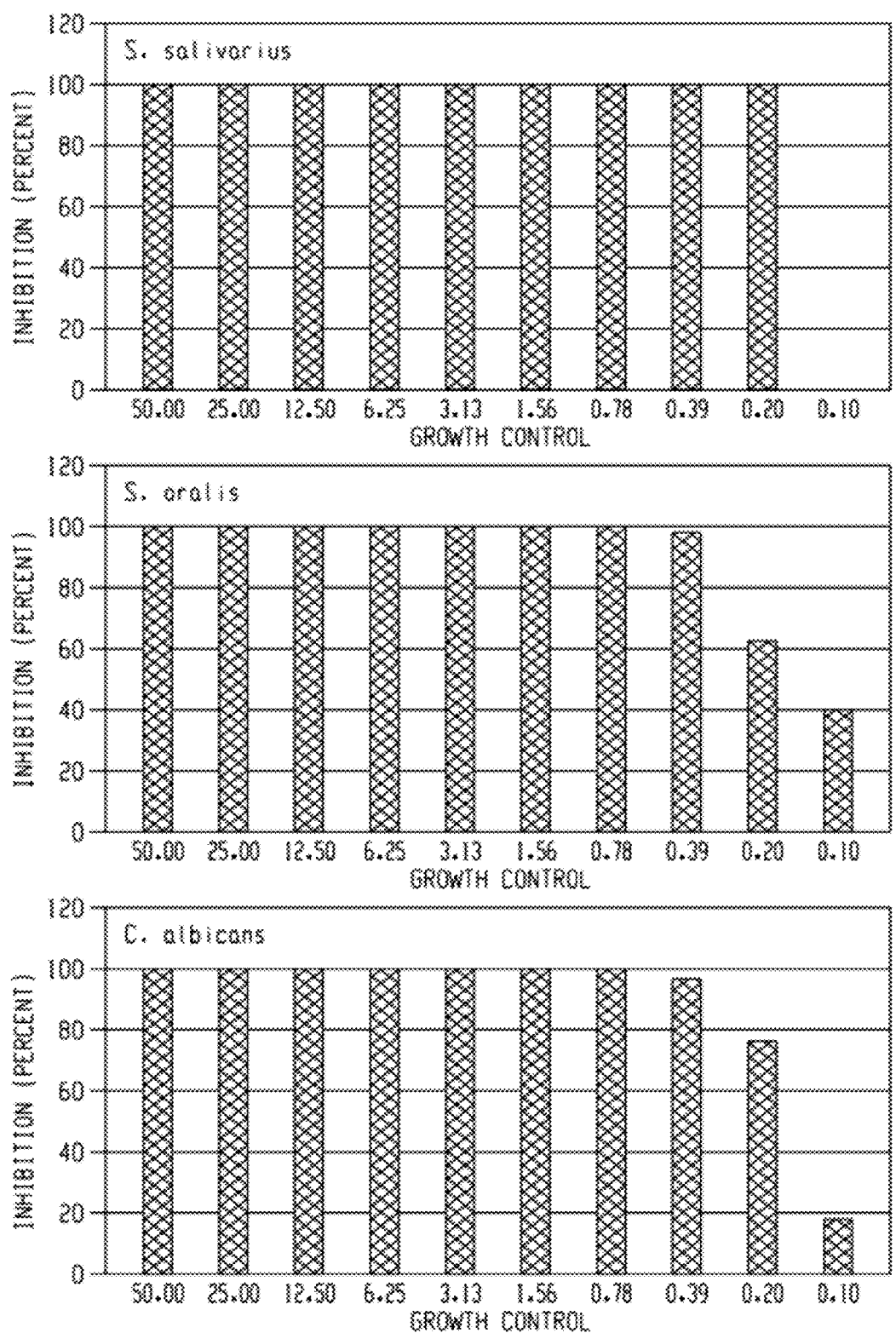
FIG. 16 presents graphs depicting activity of an example barrier-forming composition against biofilms formed by bacteria and fungi, as described in Examples 77-79.

FIG. 16 also reports data on Examples 77-79 as a graph of % inhibition versus growth control. These results showed that Example 3 barrier-forming composition inhibited bacterial and fungal microbes with an MIC of 0.2% against biofilms formed by *S. salivarius, S. oralis,* or *C. albicans.*

Examples 80 and 81

Figure 17:
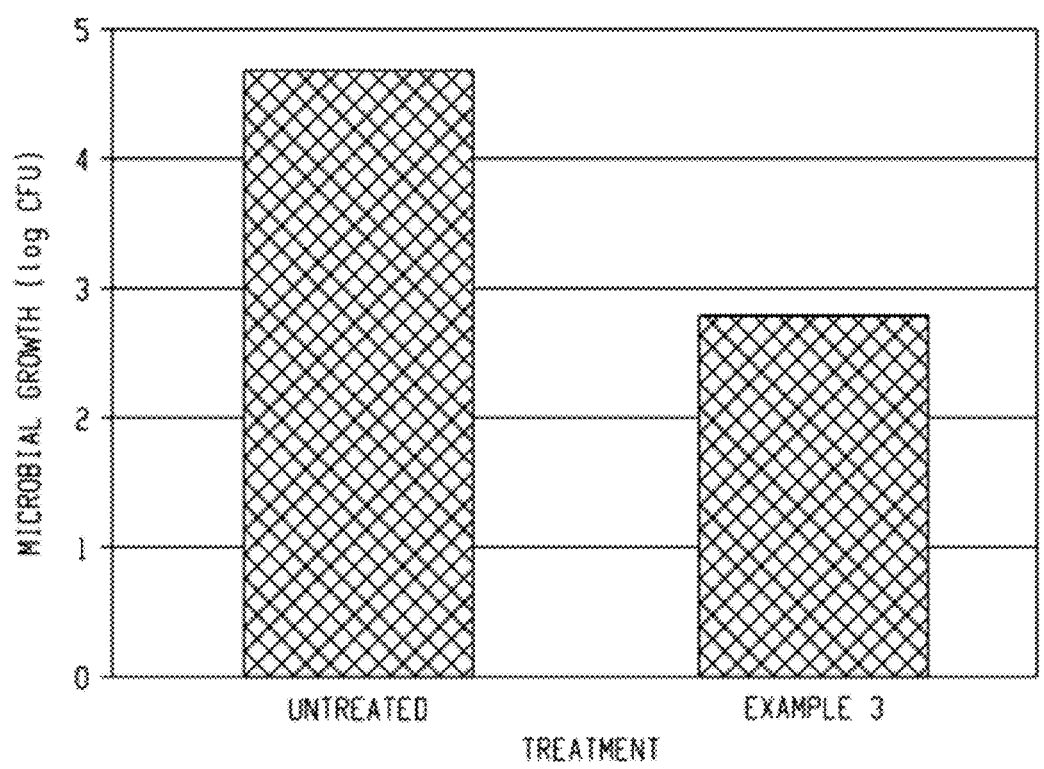
FIG. 17 is a graph showing activity of an example barrier-forming composition on microbial biofilms after a 1-min exposure, as described in Examples 80-81.

In Example 80 we evaluated the effect of 1 minute exposure of *C. albicans* early phase biofilms to Example 3, and found that even with an exposure for as short a time as 1 minute, it was able to inhibit biofilm formation (FIG. 17). Example 81 was an untreated control sample.

Examples 82-84

Ability of Barrier-forming composition to Treat Mature Biofilms

To determine whether the barrier-forming composition can treat biofilms, we evaluated its activity against fully formed mature biofilms. Biofilms were grown to mature phase, and then exposed to Example 7 for 2 or 4 hours, and the resulting CFUs were determined. A composition that causes at least 2-log reduction in microbial CFUs compared to untreated cells is considered to be effective against microbial biofilms.

As shown in Table VII, exposure to Example 7 resulted in complete eradication of biofilms formed by *C. albicans* and S. oxalis, and a 3.4-log reduction in CFUs for biofilms formed by *S. salivarius* compared to the untreated control (log CFU=3.95 vs. 7.36, respectively).

TABLE VII

Effect of Example 7 on mature biofilms (log CFU)

| Exposure time | Example 82 C. albicans | Example 83 S. oralis | Example 84 S. salivarius |
|---|---|---|---|
| Control | 5.60 | 7.40 | 7.36 |
| 2 h | 0 | 0 | 4.00 |
| 4 h | 0 | 0 | 3.95 |

In summary, the results indicate that Example 15 possesses potent activity against biofilms formed by bacteria and fungi.

Examples 85-86

The Barrier-forming composition is Also Active Against Viruses

The activity of barrier-forming composition against viruses, including respiratory viruses (influenza virus H1N1, strain 2009/H1N1/infA) and the human immunodeficiency virus (HIV) was determined.

The barrier-forming composition inhibits the infectivity of influenza A

To evaluate the effect of the barrier-forming composition on the infectivity of influenza virus, Madin Darby canine kidney (MDCK) cells were grown to ≥90% confluence at 37° C. prior to infection. MDCK cells are used routinely for assays involving influenza viruses.

In Example 85 cell monolayers were exposed to the Example 7 barrier-forming composition. In control Example 86 the cell layers were exposed to optiMEM (+P/S,+Lglu) tissue culture media for different times: (1) T1: 30 min exposure, (2) T2: 1 h exposure, (3) T3: 2 h exposure. Next, the formulation was removed and the cell monolayers were infected with influenza virus (multiplicity of infection (MOI)=0.1). Cells that were untreated or infected immediately after exposure (TO) were used as baseline controls. Infected cells were then centrifuged, resuspended in 500 µL of growth medium, and incubated at 32.5° C. for 48 hours. Immunofluorescence microscopy (using FITC labeled anti-influenza antibody) was also used to evaluate the effect of the Example 7 barrier-forming composition on the ability of influenza virus to infect mammalian cells.

Figure 18:
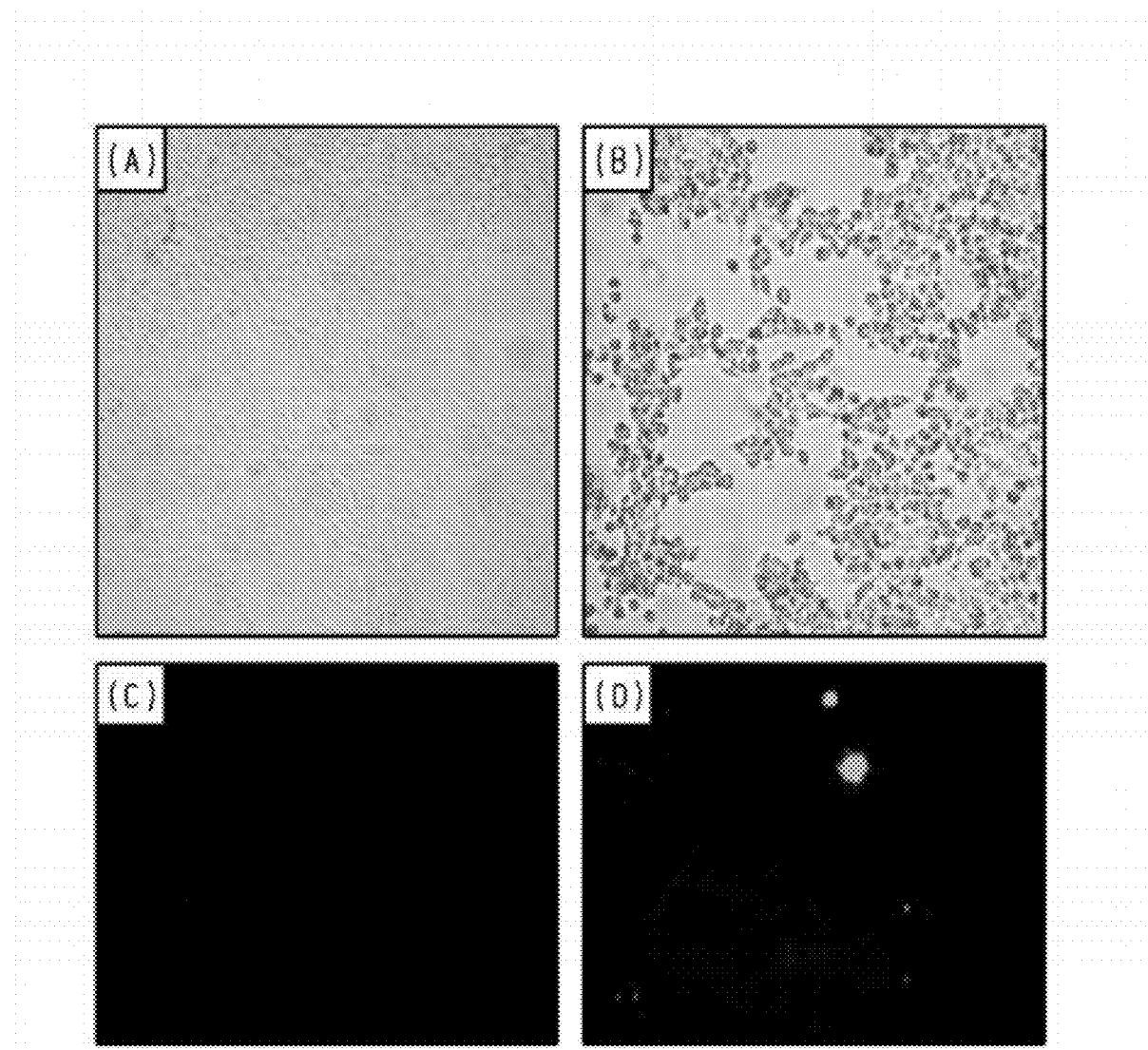
FIG. 18 presents fluorescent microscopy photographs showing the effect of an example barrier-forming composition on cytopathic effects (CPE) of influenza (H1N1)-infected MDCK cells, as described in Examples 85-86.

FIG. 18 shows the effect of Example 7 on cytopathic effects of influenza-infected MDCK cells (Example 85) (panels A and C), and control Example 86 (panels B and D). Images were obtained from: phase contrast (A-B), and immunofluorescence microscopy (C-D). No identifying cytopathic effect (CPE) was observed in formulation-treated cells. Untreated cells displayed typical CPE including focal rounding and degenerative changes.

The data showed that exposure of cell monolayers to Example 7 for 30 minutes, 1 hour, or 2 hours remained confluent and healthy (Example 85). In contrast, in the untreated cells and cells treated immediately prior to infection (T0) (control Example 86) demonstrated substantial cytopathic effect. As seen in FIG. 18 panel C, no fluorescence was observed in the barrier-forming composition treated cells of Example 85, while the untreated cells of Example 86 exhibited fluorescence (FIG. 18 panel D).

Figure 19:
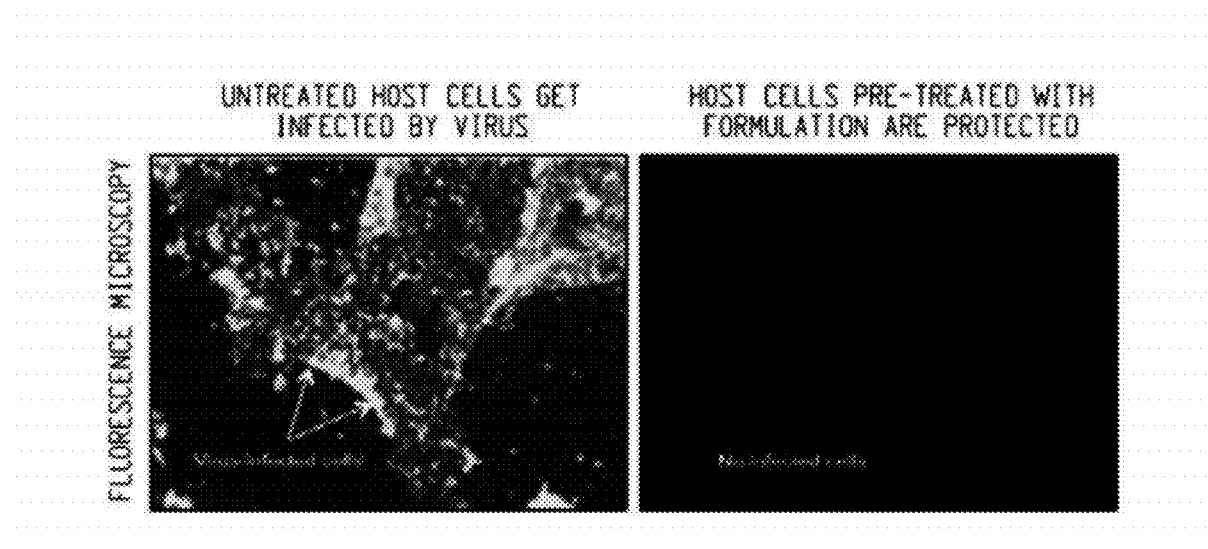
FIG. 19 presents fluorescent microscopy photographs showing the effect of an example barrier-forming composition on against H1N1 virus, as described in Examples 85-86.

Further fluorescence microscopy images corresponding to Examples 85 and 86 are presented in FIG. 19.

Examples 87 and 88

Activity of Barrier-forming composition on Viral Load Using Quantitative PCR

Figure 20:
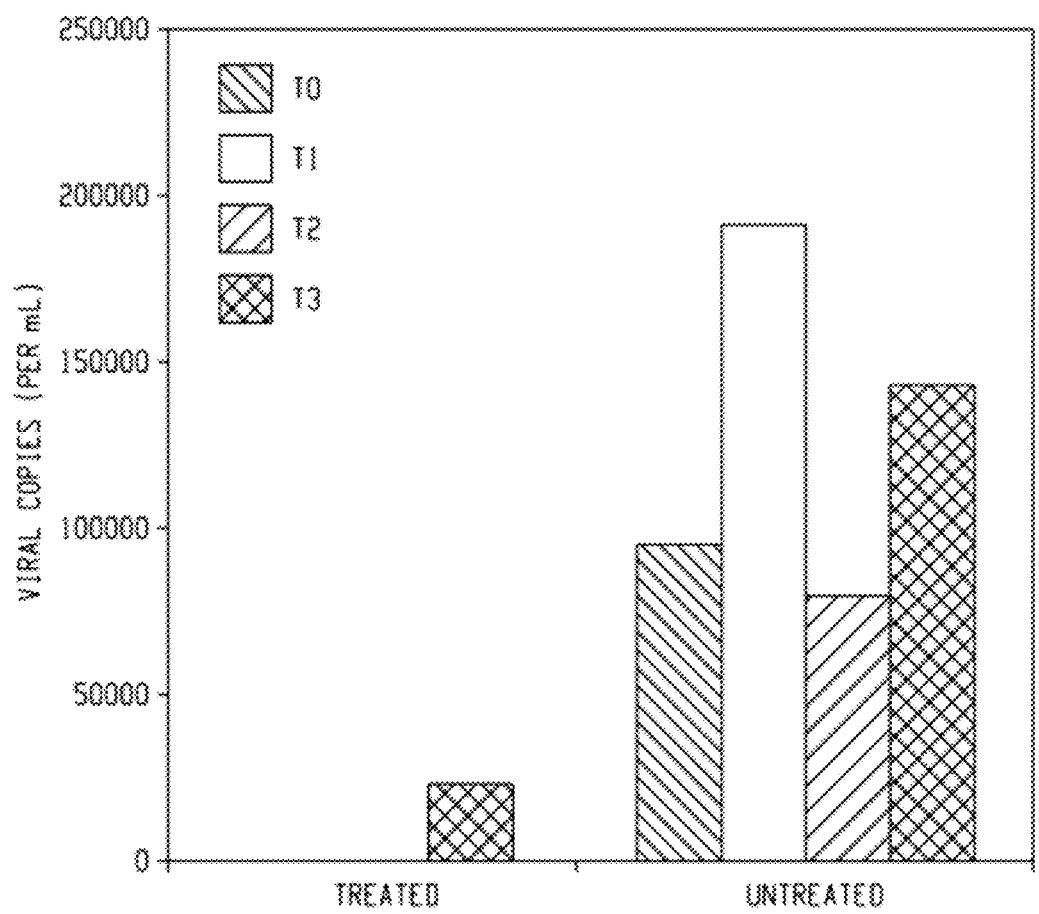
FIG. 20 is a graph showing levels of influenza virus in infected barrier-forming composition treated and -untreated cells, as determined by quantitative PCR, as described in Examples 87-88.

FIG. 20 shows levels of influenza virus in infected treated cells (Example 87) and untreated cells (Example 88), as determined by quantitative PCR. In Example 87, cells were treated with Example 7 and in control Example 88 the cells were left untreated. Later the supernatants were collected and analyzed for the presence of virus.

Cell culture supernatants from the same assay as in Examples 87 and 88 were collected and nucleic acid extracted using QIAamp Viral RNA Kit (QIAGEN, Valencia, Calif.). Random hexamer primers (Invitrogen Carlsbad, Calif.) were used to create a cDNA library for each specimen. Reverse transcription reactions were performed with M-MLV RT (Invitrogen, Carlsbad, Calif.) according to the manufacturer's specifications. Quantitative analysis was performed on a StepOne Plus Taqman Real Time PCR (Applied Biosystems, Branchburg, N.J.) using TaqMan Universal PCR Master Mix (Applied Biosystems, Branchburg, N.J.), 2 µl of cDNA sample, and primers/probes targeting the influenza matrix gene. A reference standard was prepared using a cDNA fragment of the H1N1 matrix gene and human RNAse P amplified by conventional RT-PCR, gel purified (QIAquick, Qiagen, Valencia, Calif.), and quantified using a spectrophotometer (Beckman Coulter, Brea, Calif.).

As shown in FIG. 20 and Table IV, the Example 87 cells treated Example 7 for 30 min or 60 min did not have detectable influenza at 48 hours post infection. Moreover, treatment with Example 7 for 2 hours resulted in a 6-fold decrease in viral load, compared to the untreated control or those treated immediately prior to infection (Example 88).

TABLE VIII

|  | Example 87 | Example 88 (control) |
|---|---|---|
| 30 min | 0 | 192000 |
| 60 min | 0 | 79800 |
| 120 min | 23400 | 143000 |

Examples 89-91

Barrier-forming composition has Direct Antiviral Effect Against Influenza Virus

To determine whether the barrier-forming composition has direct antiviral activity against influenza virus, we infected African Green Monkey Kidney (CV-1) cells (grown in 24-well plates to 90% confluence) with influenza virus that was pre-treated with Example 7. CV-1 cells are routinely used a highly susceptible substrate for diagnosis and study of viruses.

In Examples 89-91, a standardized amount of influenza (0.1 MOI) was pretreated for 5 minutes at room temperature with: (1) Example 7 (to form Example 89), (2) control Example 6, a compound without CPC but with preservatives (to form Example 90), and (3) control Example 5 placebo alone (a compound without CPC and preservatives) (to form Example 91). After the 5 minute incubation virus/drug mix was diluted by an additional equal volume with optiMEM (+P/S,+Lglu) to dilute out the treatment compositions.

In Examples 89-91, CV-1 cells were prepared as described in above. The Example 89-91 treated and untreated viruses were then inoculated onto the cells as described above.

Figure 21:
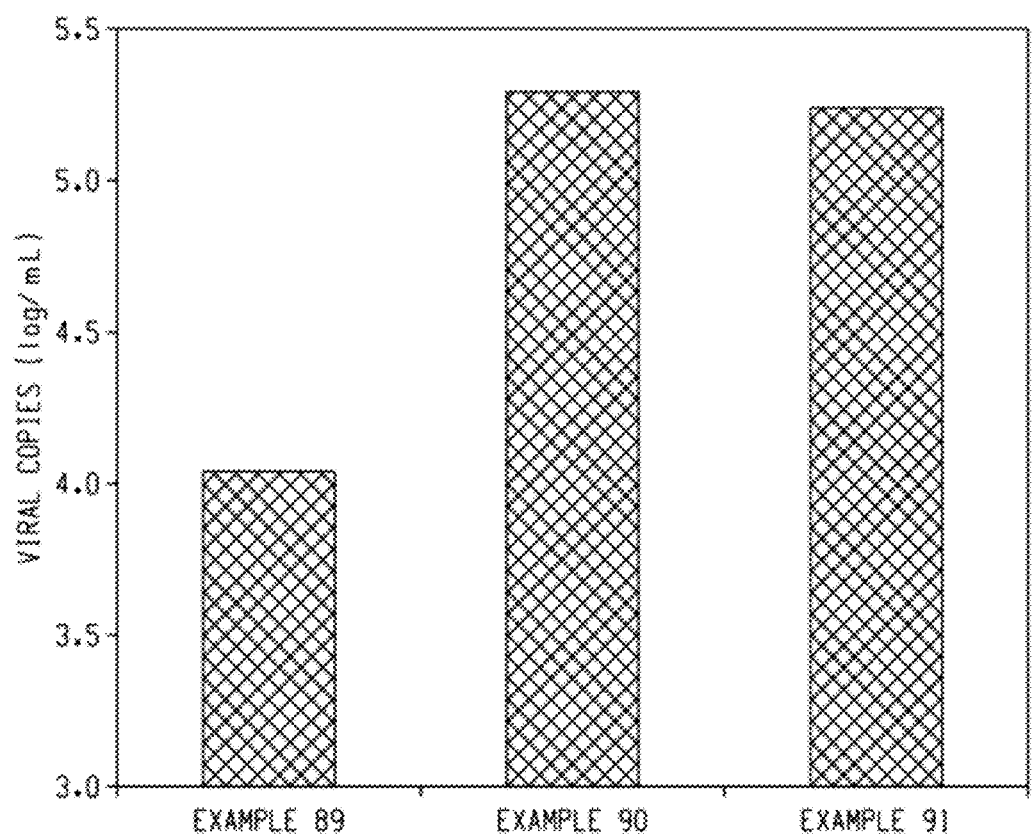
FIG. 21 is a graph showing direct antiviral activity of example barrier-forming compositions prepared with or without preservatives and antimicrobial agent (CPC) against influenza virus, determined using quantitative PCR, as described in Examples 89-91.

Influenza viral load was determined by real time PCR as described above. The data as shown in FIG. 21 showed significant decrease in viral load for influenza virus pretreated with the Example 7 barrier-forming composition containing the antimicrobial agent CPC (Example 89), compared to those containing only the barrier-forming composition and/or preservative but no CPC (Examples 90 and 91). Pre-treatment of virus with Example 7 exhibited significant decrease in viral copies, compared to formulations with no CPC.

These results demonstrate that the Example 7 barrier-forming composition possesses direct antiviral activity against influenza virus that is not inherent in Examples 5 and 6.

Examples 92 and 93

In Examples 92 and 93, the barrier-forming composition's ability to inhibit the infectivity of influenza A (2009/H1N1/infA) was tested. African Green Monkey Kidney (CV-1) cells were grown in 24-well plates to 90% confluence. Next, the barrier-forming composition, Example 7, was applied to the cells (20% Example 7, 80% OptiMeM, working CPC concentration of 0.02%.) in Example 92. Each time point matched with control Example 93 (No barrier-forming composition applied, 100% OptiMeM). The barrier-forming composition was allowed to dwell on the surface for 30 minutes, and then removed from the cell monolayer. Cells were thoroughly washed twice with sterile optiMEM (+PfS,+

Lglu). Influenza was inoculated at MOi=0.1 at 30 minute intervals from T0 through T+6 hours. Following infection, cells were then centrifuged @ 2200 rpm×30 minutes and 500 μl of optiMEM (+P/S, +Lglu, 2 μg/ml trypsin (sigma-Aldrich, St Louis, Mo.)) was applied. Infected cells were grown at 32.5° C. for 96 hours at 5% $CO_2$. The influenza viral load was determined by real time PCR.

Figure 22:
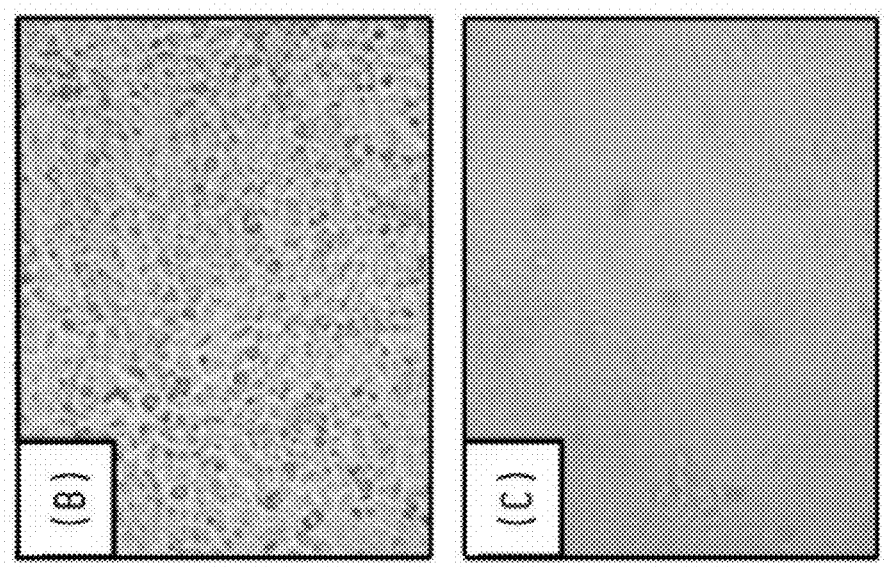
FIG. 22 shows the activity of an example barrier-forming composition against H1N1 virus over a 6 hour time period. Panel (A) is a graph showing a percent inhibition in viral growth compared to an untreated control. Panels (B) and (C) are micrographs of (B) untreated and (C) barrier-forming composition treated cells.
Figure 22:
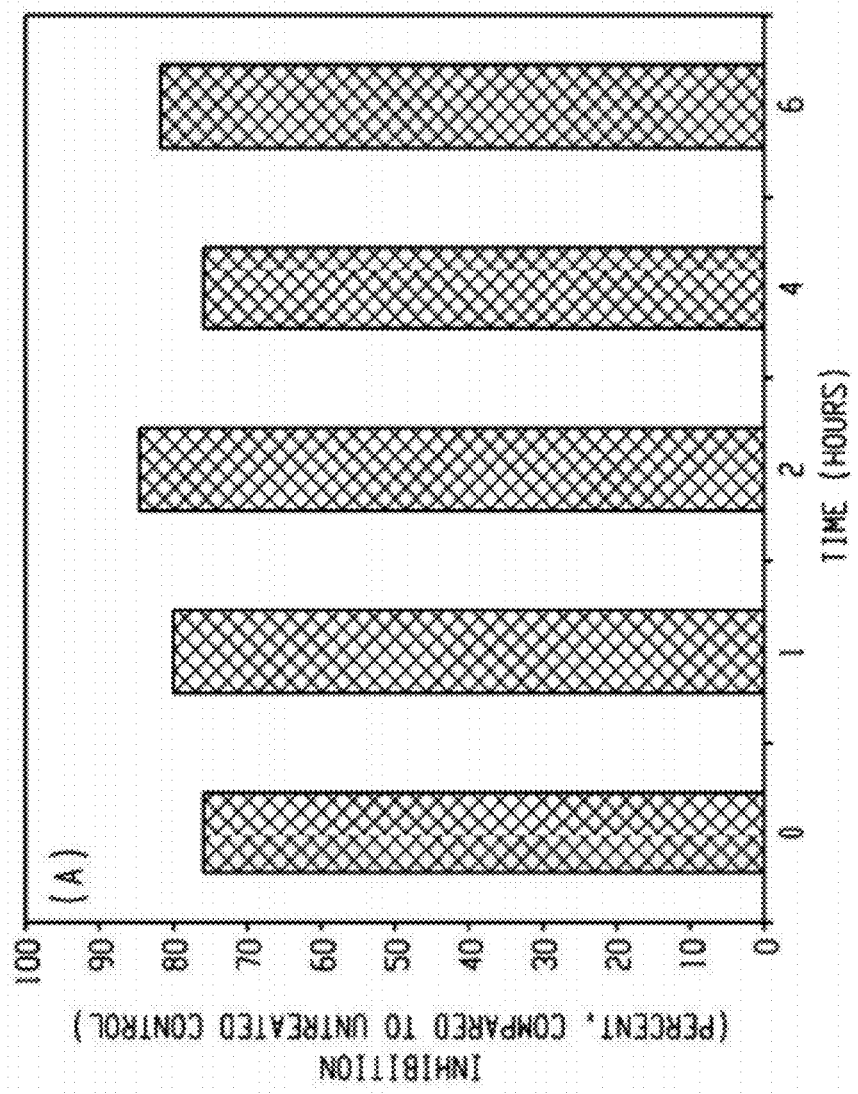

As shown in FIG. 22, pre-treatment of host monolayers with glycerine-xanthan gum formulation results in inhibition of viral infection by up to 84.93% compare to untreated controls. The fact that inhibition of viral infection was observed in host cells despite removal of the barrier-forming composition demonstrates that the barrier-forming composition formed a protective barrier on host cells, which prevented viral invasion at least 6 hours.

FIG. 1 may be referred to as a possible mechanism accounting for the inhibition of infection.

Examples 94-96

Barrier-forming composition Exhibits Activity Against HIV

Figure 23:
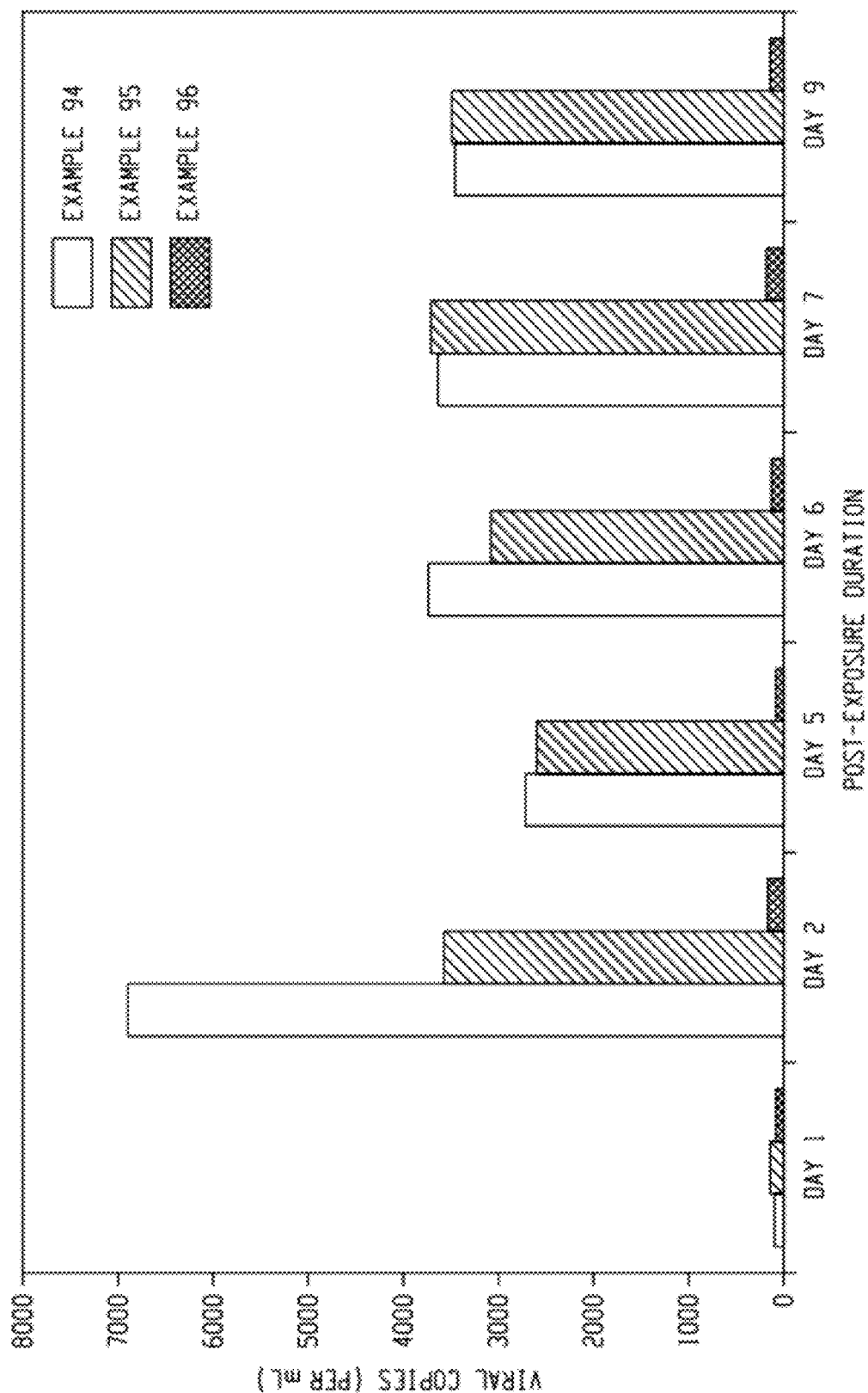
FIG. 23 is a graph showing the activity of formulations against HIV, as described in Examples 94-96.

Examples 70-72 determined whether the barrier-forming composition possessed activity against HIV. Host MT mammalian cells were plated into 96-well round bottom plates at a density of 15,000 cells/well in RPMI/10% FBS/PS. The next day (Day 2), virus was pretreated with control Example 5 (to form Example 94), control Example 6 (to form Example 95), or Example 7 (to form Example 96) for 5 minutes and added to cells. After 24 hours of exposure to formulation, the MT (macaque) mammalian cells were washed 3 times with phosphate buffered saline (PBS) and fresh media was replaced. Supernatant (10 μL) was collected post-treatment on Days 1, 2, 5, 6, 7, and 9, and the viral load was determined by reverse transcriptase (RT) activity. FIG. 23 shows a graph of the viral copies per mL for each of Examples 72-74 over a 9 day span.

The results showed that Example 7 in Example 96 exhibited anti-HIV activity at all time points monitored post-treatment.

The control Example 5 or control Example 6 without CPC and/or preservative in Examples 94 and 95 exhibited only minimal anti-HIV activity.

In summary, our findings demonstrate that the barrier-forming composition Example 7 containing CPC exhibits long-lasting antiviral activity against HIV.

Example 97

Representative organisms viral lesions are important infections in different mucosal tissues. In Example 97 an experiment was performed to determine whether the barrier-forming composition exhibits activity against the common oral Epstein-Barr virus (EBV). Western blotting was used to evaluate the ability of the Example 8 barrier-forming composition to degrade lytic viral protein EAD (indicating inhibition of viral replication).

Figure 24:
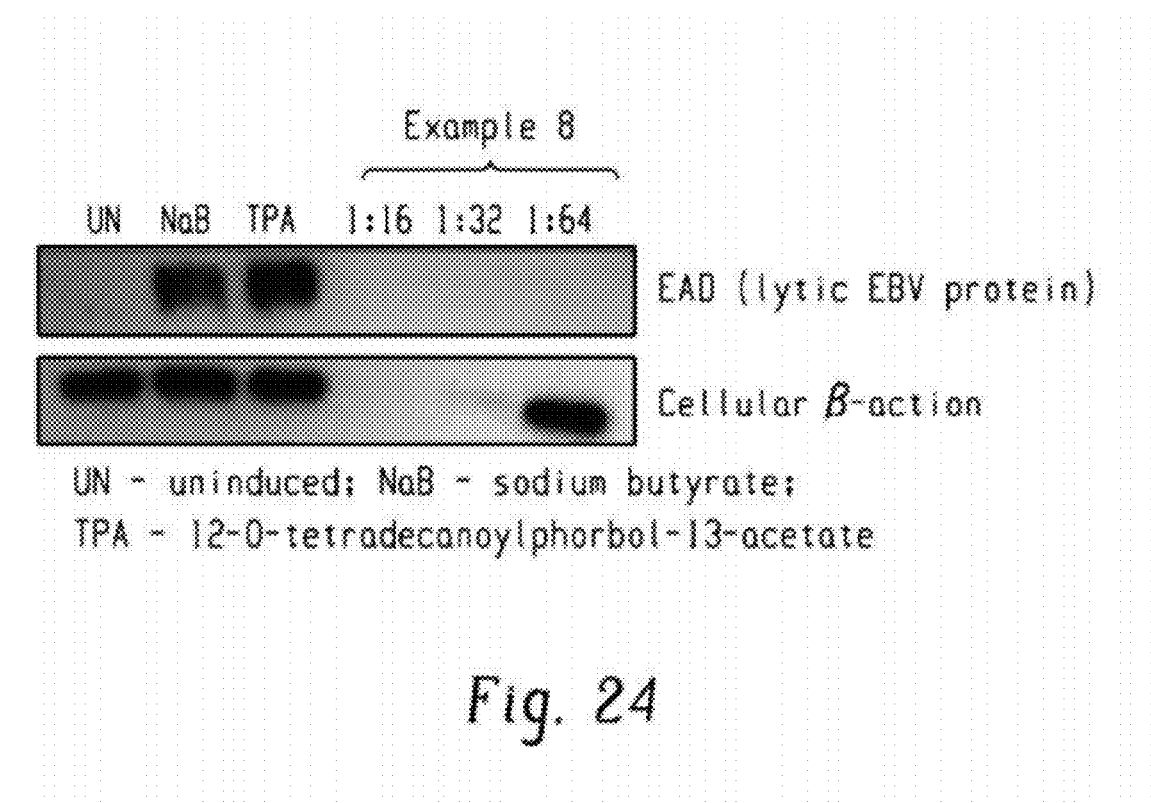
FIG. 24 is a Western blot showing activity of Example 8 against Epstein-Barr Virus (EBV), as described in Example 97.

In Examples 97, EBV-infected gastric epithelial cells were exposed to different dilutions (1:16, 1:32 and 1:64) of Example 8, and the presence of EAD protein was detected using specific antibodies. Presence of cellular β-actin was used as an indicator of epithelial cell integrity. As shown in FIG. 24, 1:64 dilution of Example 8 degraded EAD without affecting cellular actin. These results demonstrate that Example 8 specifically inhibits viral replication, and as such, is an effective anti-viral and useful for prevention of viral infection.

Examples 98-100

Duration of Anti-Microbial Barrier versus Commercial Mouthwash Product

Figure 7:
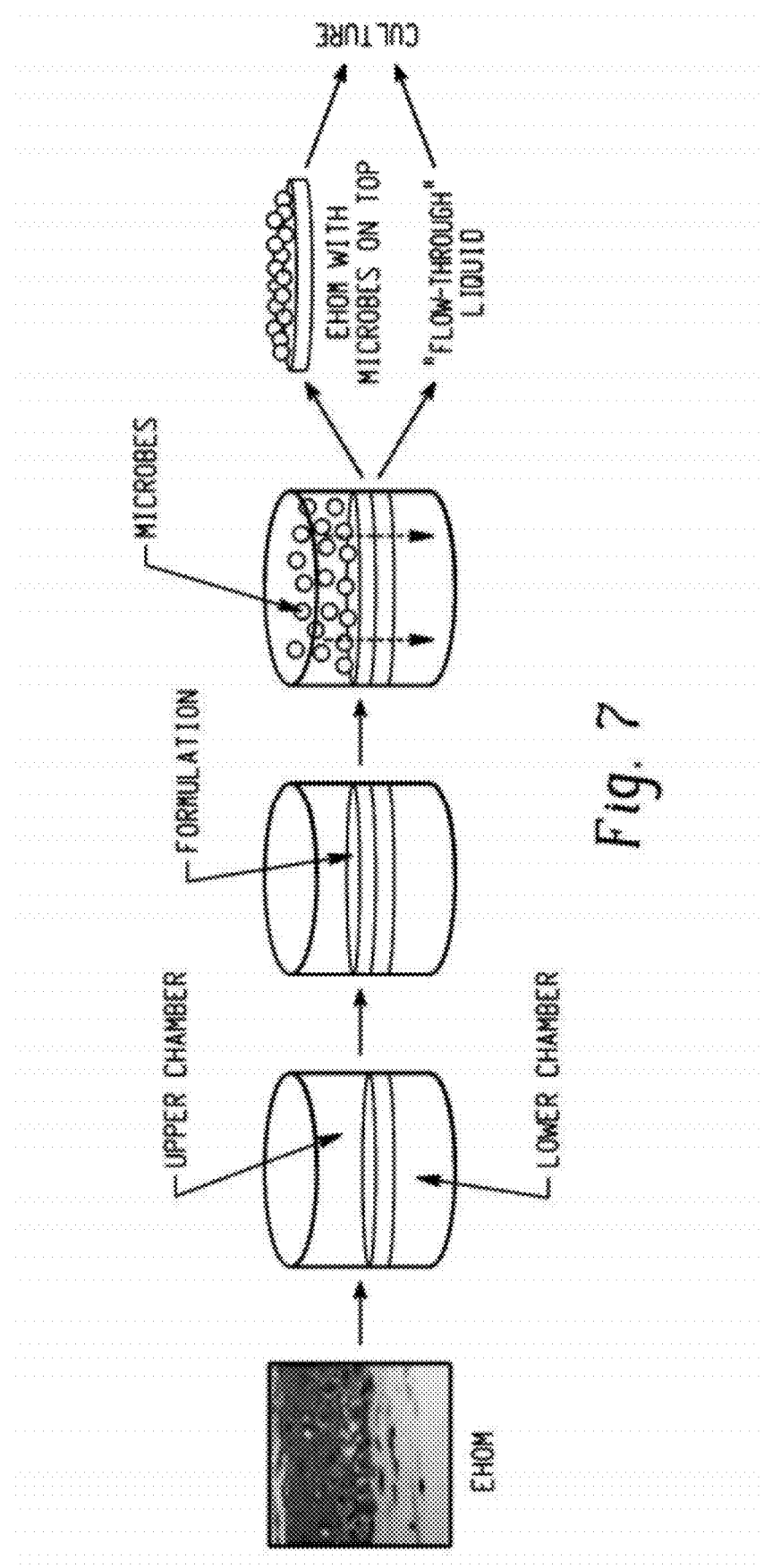
FIG. 7 is a schema showing the method of evaluation of microbial growth in the upper and lower chambers of an EHOM assay, as described in Examples 27-28.

To determine the duration for which the barrier-forming composition can maintain the antimicrobial activity, bacteria and fungi were exposed to an EHOM of Example 2 that was treated with the barrier-forming composition of Example 7 in a well and an EHOM of Example 2 that was treated with a comparative commercial product in a well for 2 minutes. The bacterial and fungal microbes were overlaid on top of the control untreated EHOM (Example 98) and the treated EHOMs (Example 99 and Comparative Example 100). Next the residual (flow-through) solution was removed from the bottom well (lower chamber of the EHOM model) and spread onto agar medium plates. FIG. 7 depicts this test method for further clarity. These plates were then incubated at 37° C., and the number of microbial cells (colony forming units, CFUs) growing after 24 hours were counted.

In control Example 98 an untreated EHOM was tested. In Example 99 S. mitis bacteria was overlaid on the barrier-forming composition as described above. Example 100 is a comparative example showing the activity of commercially available LISTERINE (containing ethanol (26.9%), menthol, thymol, methyl salicylate, and eucalyptol) against S. mitis bacteria. Table IX shows the results.

TABLE IX

| | CFUs of S. mitis bacteria in flow through liquid from EHOM | | |
|---|---|---|---|
| Time post-exposure | Example 98 (control) | Example 99 | Example 100 (comparative) |
| 2 hours | 1150000 | 5820 | 780000 |
| 4 hours | 1400000 | 5500 | 800000 |
| 6 hours | 1600000 | 6000 | 840000 |

Examples 101-103

In Examples 101-103, the same procedure of Examples 98-100 was performed except Candida albicans fungus was tested on the barrier-forming composition as described above. Table X shows the results. Example 103 is comparative, showing the activity of commercially available LISTERINE.

TABLE X

| | CFUs of Candida albicans in flow through liquid from EHOM | | |
|---|---|---|---|
| Time post-exposure | Example 101 (control) | Example 102 | Example 103 (comparative) |
| 2 hours | 1150000 | 12000 | 124000 |
| 4 hours | 2900000 | 12000 | 252000 |
| 6 hours | 3900000 | 13000 | 350000 |

The data further showed that Example 7 barrier-forming composition maintained activity for up to and including 24 hours. Taken together, these results showed that unlike LISTERINE, the Example 7 barrier-forming composition continued to maintain an intact barrier on EHOM tissues for up to and including 24 hours.

Examples 104-153

Figure 33:
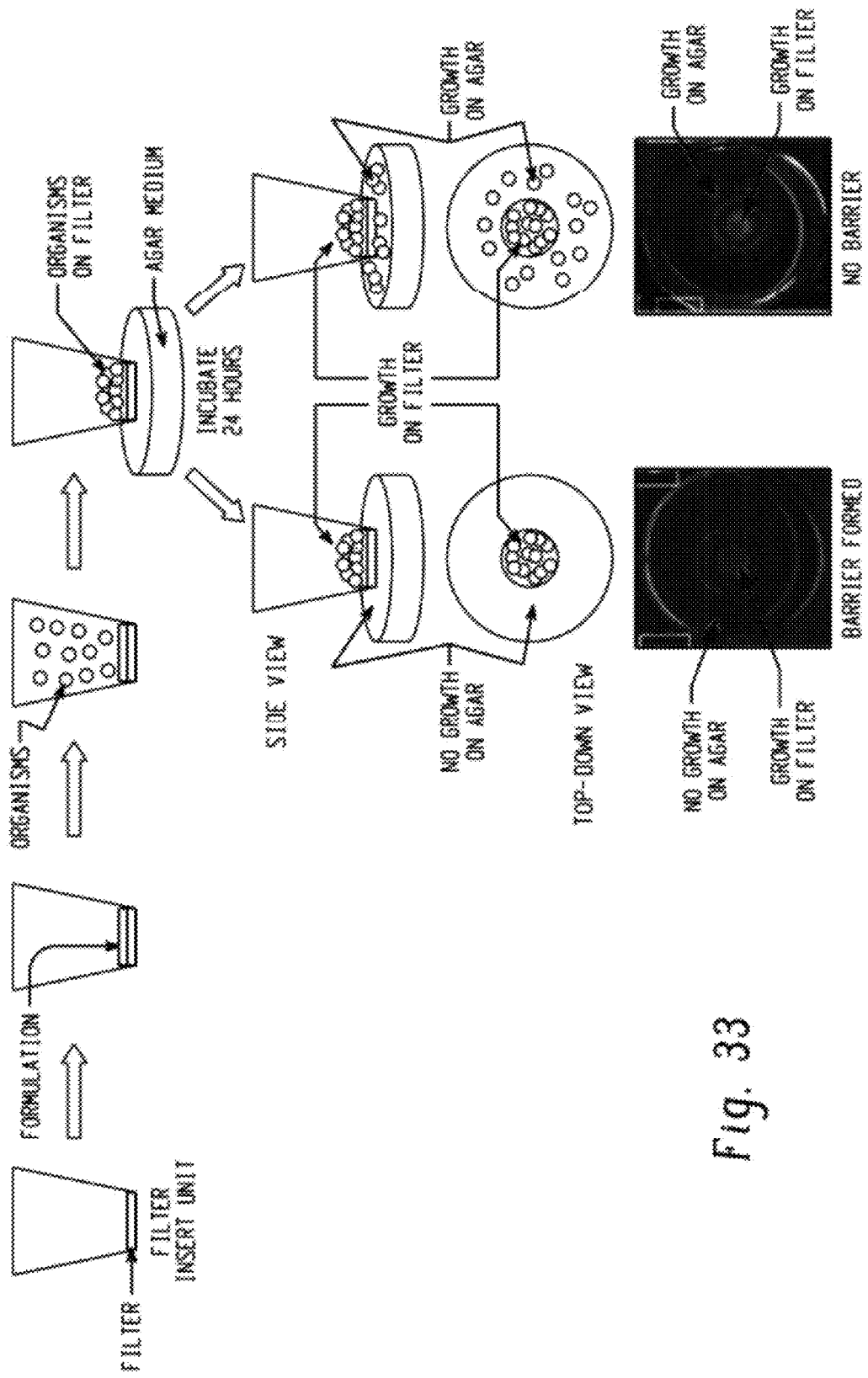
FIG. 33 shows is a schema describing the in vitro filter insert-based model to evaluate penetration of microbes across the barrier formed by example barrier-forming compositions, as described in Examples 199-205.

To identify further examples of concentrations of glycerin and xanthan gum that can form a barrier effective in preventing the passage of microorganisms, different concentrations of the gum xanthan gum and humectant glycerin were tested (5%-95% glycerin; 0.005%-0.5% xanthan gum) singly and in combination using an in vitro filter insert-based barrier model. FIG. 33 shows the general test method used for Examples 104-153.

Filter inserts of 3 μm and 8 μm diameter pore size were used for testing the passage of bacteria (Streptococcus salivarius) and fungi (Candida albicans), respectively. Glycerin or xanthan gum or their combinations (100 μL aliquots) were overlaid on the surface of the filter to form a barrier. The filter had a diameter of 24 mm. Thus, the film had a thickness of approximately 0.01 mm on the filter, mimicking a value in the range of thicknesses of the composition film when applied in a therapeutically effective amount to the mouth. Next, $5 \times 10^4$ cells of either bacteria or fungi were applied on top of the formed barrier in the filter inserts. Next, we placed these filter inserts on the surface of agar medium (Brain Heart Infusion (BHI) medium for bacteria, Sabouraud Dextrose (SD) medium for fungi) in 6-well plates. The plates along with the filter inserts were incubated overnight for 24 hours at 37° C.

The plates were monitored for the presence of bacterial or fungal growth CFUs (colony forming units) in the agar medium as well as in the filter insert. Microbial growth in the filter insert only, but not in the agar medium, demonstrated that an effective barrier was formed on the filter, which prevented passage of microorganisms. Conversely, growth in the agar medium around the filter insert suggested that the tested agents failed to form an effective barrier, allowing the organisms to go through the filter.

The results reported in Table XI showed that glycerin was able to form a barrier at concentrations greater than or equal to 55%, when tested alone. In contrast, xanthan gum alone did not form a barrier at any of the concentrations tested (ranging from 0.005% to 0.4%). However, it was observed that when combined with 0.01% xanthan gum, a barrier was formed at glycerin concentrations 7%, 45%, 55%, and 65%. Furthermore, combination of 0.4% xanthan gum with glycerin concentrations of 7%, 15%, 25%, 35%, 45%, 55%, and 65% also formed a barrier. Therefore, specific combinations of glycerin and xanthan gum were identified that can form a barrier that prevents passage of microorganisms in an in vitro filter insert-based model.

TABLE XI

|  |  | Examples 104-112 | Example 113 | Examples 114-121 | Examples 122-129 | Examples 130-137 | Examples 138-145 | Examples 146-153 |
|---|---|---|---|---|---|---|---|---|
|  |  | Xanthan Gum (%) | | | | | | |
|  |  | 0 | 0.005 | 0.01 | 0.05 | 0.1 | 0.2 | 0.4 |
| Glycerine (%) | 0 | No | No | No | No | No | No | No |
|  | 5 | No |  | No | No | No | Yes | No |
|  | 7 | No |  | Yes |  |  |  | Yes |
|  | 15 | No |  | No | No | No | Yes | Yes |
|  | 25 | No |  | No | No | No | Yes | Yes |
|  | 35 | No |  | No | No | No | Yes | Yes |
|  | 45 | No |  | Yes | No | No | Yes | Yes |
|  | 55 | Yes |  | Yes | No | No | Yes | Yes |
|  | 65 | Yes |  | Yes | No | No | Yes | Yes |

'No': no barrier formed;
'Yes': barrier formed

Microbial cells retained by the compositions of Examples 104-153 formed on filter inserts were trapped by the barrier, and were viable, thus demonstrating that the formed barrier does not have an inherent antimicrobial property without an antimicrobial agent. In other words, the microbes retained in the barrier were still active and could pose a threat to infection; for example, if they are freed from the barrier by abrasion or after the barrier loses its integrity.

Examples 154-157

In addition to the Examples above on EHOM samples, further testing was performed to further demonstrate the barrier-forming composition (a) does not damage the host tissues, and (b) is able to prevent microbial invasion into the human mucosal tissues. These criteria were tested for two representative combinations (glycerine:xanthan gum; 7%:0.01% and 35%:0.4%), selected based on the in vitro results of Examples 104-153, because they successfully formed a barrier. Formulations containing these two combinations were tested using the EHOMs of Example 2 that mimic the mucosal lining.

The EHOMs were treated with the various formulations of Examples 3 and 4 in either 1% (Examples 154 and 155) or 5% (Examples 156 and 157) dilutions in normal saline [0.9%]) for about 2 minutes to form Examples 154-157. Each EHOM was covered with 300 μL of one of the tested formulations and left under the sterile hood for 10 minutes at room temperature (25° C.). At the end of the contact period, tissues were washed twice with culture medium to remove the formulations.

Example 158

After treatment with Examples 3 and 4, the EHOMs were then examined for possible macroscopic tissue damage (presence of holes). Tissue damage was also investigated by histological analyses. For this purpose, biopsies were taken from each EHOM and fixed with 4% paraformaldehyde solution and then embedded in paraffin. Thin sections (4 μm) were stained with eosin-hematoxilyn and mounted with a coverslip in 50%-glycerine mounting medium, observed through an optical microscope, and photographed. The treated EHOMs and a control untreated EHOM were examined for macroscopic tissue damage and structural changes. There was no visible damage (holes) in the untreated or treated tissues at a magnification of ×500 in five different EHOMs tested.

Example 159

Evaluation of Barrier-Forming Composition Causing Damage to Host Cells (Cytotoxicity assay)

Figure 25:
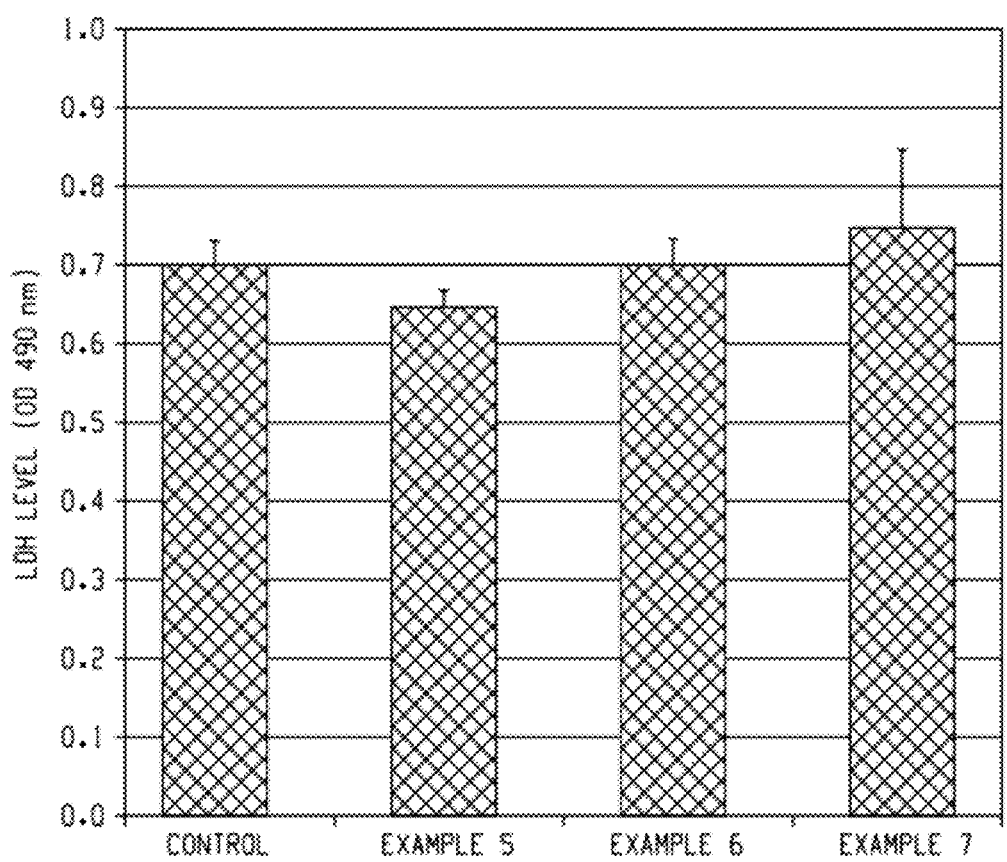
FIG. 25 is a graph showing LDH levels as an indicator of cellular integrity in untreated (control) EHOM or EHOMs tissues exposed to Examples 5-7, as described in Examples 154-159.

The Example 156 and 157 EHOMs that were treated with the 5% dilution of Examples 3-7 of the barrier-forming composition were then over-layered with $1 \times 10^6$ cells of either *C. albicans* or *S. mutans* in a volume of 100 μl. The EHOMs were then placed on air-liquid culture plates and incubated for 24 hours in 5% $CO_2$ humid atmosphere at 37° C. Following this incubation period, aliquots of the culture supernatant were collected and subjected to a Lactate dehydrogenase (LDH) cytotoxicity assay (Promega, Madison, Wis., USA), as per the manufacturer instructions. 50 μl of each supernatant were transferred to a sterile 96-well flat-bottom plate. Each well was supplemented with 50 μl of reconstituted substrate mix, and the plate was incubated for 30 minutes at room temperature in the dark. To stop the reaction, 50 μl of stop solution was added to each well. Next 100 µl of the mixture was transferred to a 96-well flat-bottom plate, and the absorbance was read at 490 nm with an X-Mark microplate spectrophotometer (Bio-Rad, Mississauga, ON, Canada). LDH was assessed using LDH cytotoxicity assay. Data are means±SD. No significant difference between EHOMs treated with the Example composition and an untreated, uninfected EHOM control was noted. FIG. 25 graphically shows the results of these tests on an untreated control example, and those treated with Examples 5, 6, and 7. Similar results were obtained for the EHOMs treated with Examples 3 and 4. The tested Examples all maintained the integrity of the mucosa.

Example 160

Figure 26:
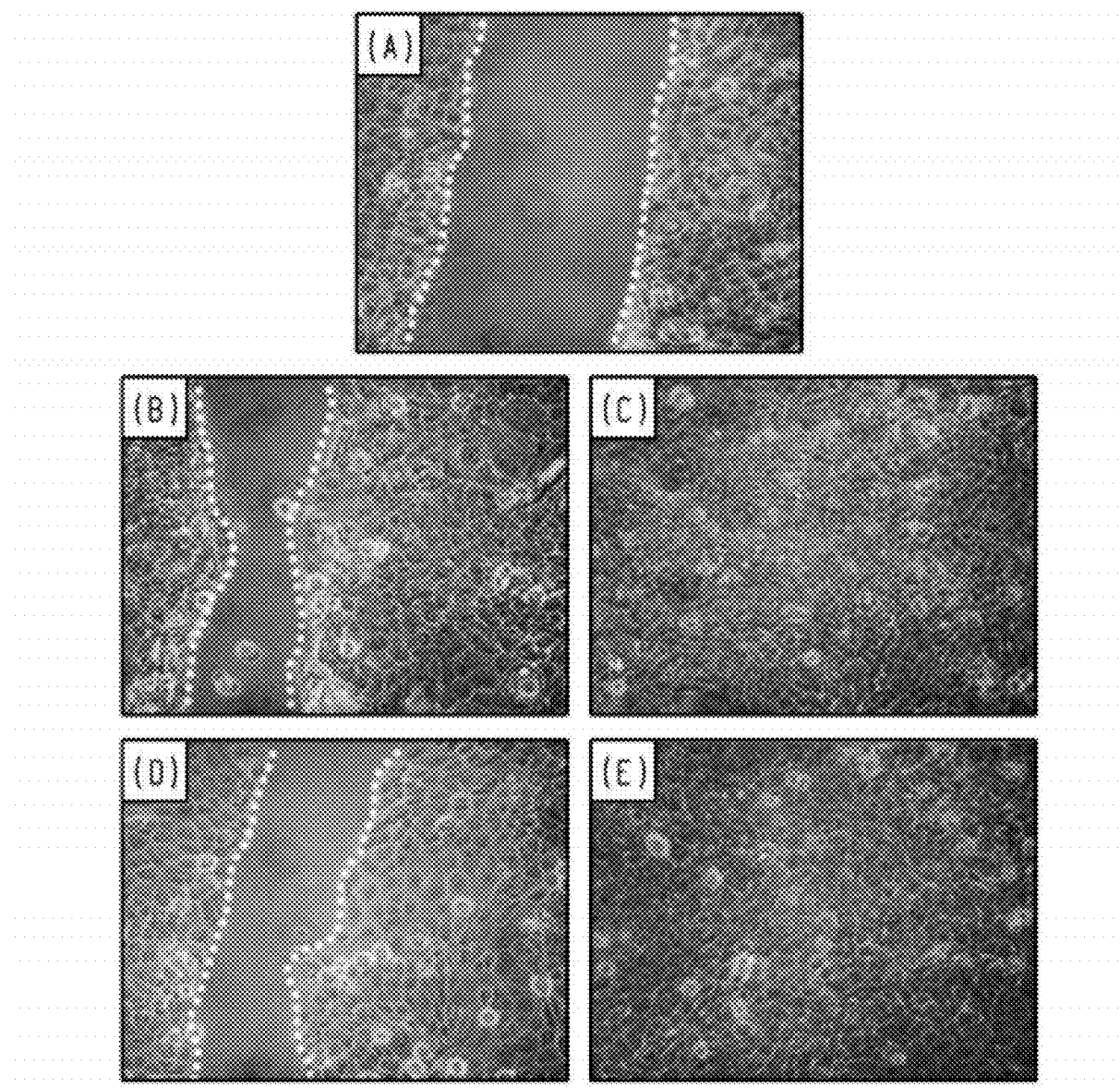
FIG. 26 shows representative photographs of a wounded oral epithelial cell culture treated with Example 3 (5% dilution) for 10 minutes, immediately after the wound (panel A), after about 6 hours (panel D), and after about 24 hours (panel E), as described in Example 160. Panels B and C show an equivalent wound on an untreated control confluent culture of oral epithelial cells after about 6 hours and about 24 hours, respectively.

Effect of Barrier-Forming Composition Formulations on Gingival Cell Growth/Migration Wound repair assays were performed. Briefly, oral (gingival) epithelial cells ($1 \times 10^4$) and fibroblasts ($1 \times 10^3$) were seeded into wells of 6-well plates and grown in appropriate culture medium. Upon confluency, wounds were made in the confluent monolayer of each well using a 200 µL pipette tip. Cultures were then exposed to 1 and 5% by weight dilutions of Examples 3 and 4 for about 2 minutes. Following exposure, the formulations were washed out twice with warm sterile culture medium, and then cell cultures were overlayered with DEM for fibroblasts and with DEM for fibroblasts and DMEH for epithelial cells, and cultured for 6 and 24 hours in a 5% $CO_2$ humid atmosphere at 37° C. Wound repair/cell migration was ascertained using optical microscope, and digital photographs were taken (Nikon, Coolpix 950). FIG. 26 shows representative photographs of a wounded oral epithelial cell culture treated with Example 3 (5% dilution) for 10 minutes, immediately after the wound (panel A), after about 6 hours (panel D), and after about 24 hours (panel E). Panels B and C show an equivalent wound on an untreated control confluent culture of oral epithelial cells after about 6 hours and about 24 hours, respectively. Similar results were seen for the cell culture treated with Example 4.

The percentage of wound closure (cell growth/migration) was calculated by comparing relative wound areas before and after exposure to the formulations using formula I stated above.

The epithelial cells were small and cuboidal in shape in both treated and untreated cultures. Similar results were observed for scratch wound model using fibroblasts (data not shown). Taken together, this data indicate that example compositions are not toxic and do not negatively impact cell growth/migration and wound healing.

Example 161

Glycerine-Xanthan Gum Formulations Form a Coating on the Human Oral Mucosa

Figure 27:
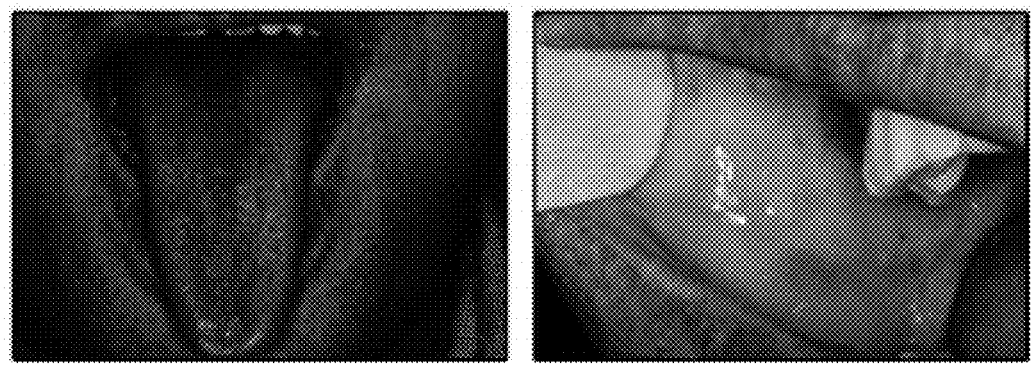
FIG. 27 are photographs demonstrating the ability of an example barrier-forming composition to coat the oral mucosal surface.

To determine whether glycerine-xanthan gum formulation can form a coating on the human oral mucosa, we spiked the Example 7 formulation with Gentian Violet (GV) as a marker dye. The spiked product (750 µL) was sprayed onto the oral cavity of human volunteers. Post-application, the oral cavity was inspected for staining, and the images were captured using a digital camera. As shown in FIG. 27, the formulation stained both cheeks and the dorsal/ventral surface of the tongue.

Examples 162 and 163

Exposure of Microbes to Barrier-Forming Composition Inhibits Cell Growth: Time-Lapse Microscopy To determine the inhibitory activity and duration for which barrier-forming compositions exhibit activity against microbes, time-lapse analysis was performed on cells exposed to the barrier-forming composition, compared to untreated bacteria and fungi.

In Example 162, *S. mutans* microbial cells were exposed to Example 7 for one minute, washed to remove any residual agent, and allowed to grow in a petri-dish containing fresh growth medium. Growth of organisms at 37° C. was monitored for a 6 hour period, and photomicrographs were taken every 20 minutes over the 6 hour incubation period using a camera connected to the microscope.

In control Example 163 the same procedure was followed with untreated cells.

Figure 28:
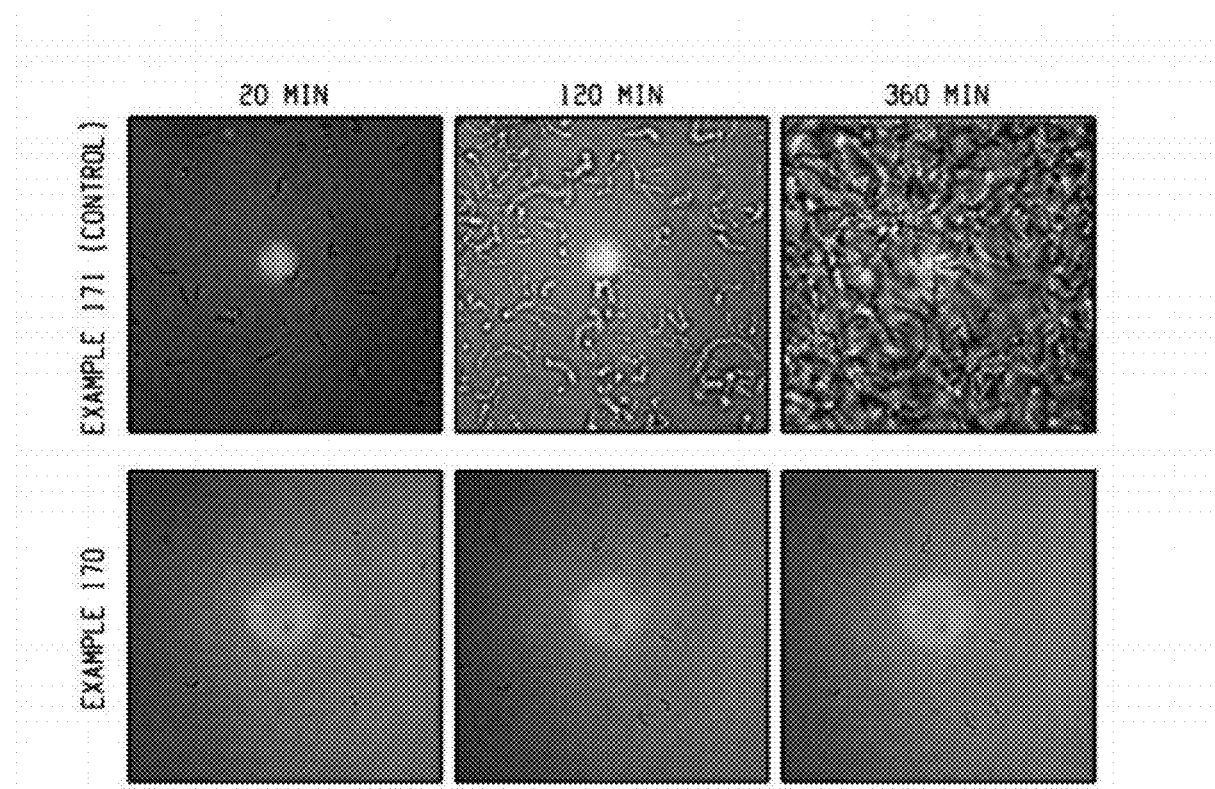
FIG. 28 are photographs showing time-lapse microscopy of bacterial growth after a 1 minute exposure to an example barrier-forming composition, as described in Examples 162-163. Images represent bacterial growth after 20 min, 120 min, or 360 min post-exposure.

As shown in FIG. 28, in contrast to the untreated bacteria, where cells reached confluence by 6 hours, microbes treated with the Example 7 barrier-forming composition failed to regrow during the same time period post-exposure. Similarly, exposure of *Candida* cells to the Example 7 barrier-forming composition completely inhibited growth during the incubation period (data not shown).

These results further confirmed that the barrier-forming composition possesses prolonged antimicrobial activity.

Examples 164-166

In vivo Study: Barrier-Forming Composition (Example 7) Lowers the Oral Microbial Load in Humans: Short- and Long-Term Activity Short-Term Activity The duration of activity of Example 7 was determined in healthy individuals by evaluating the effect of a single application on microbial burden of the oral cavity. In Examples 164-166, three healthy individuals (over 18 years of age, healthy mouth) were enrolled with informed consent, and asked to apply a single application of the composition of Example 7 on their cheeks. A single application was defined as three sprays of 0.25 ml each in volume. Next, swabs were collected from these individuals at baseline (pre-treatment), 1 hour, 2 hours, and 6 hours post-treatment. Swabs were cultured on agar media plates specific for aerobic or anaerobic organisms, incubated for 24-28 hours at 37° C., and the number of CFUs were counted. Effect of Example 7 on microbial burden was determined (CFUs), and percentage inhibition was calculated for each post-exposure time point relative to the baseline (0 minutes) CFUs.

Figure 29:
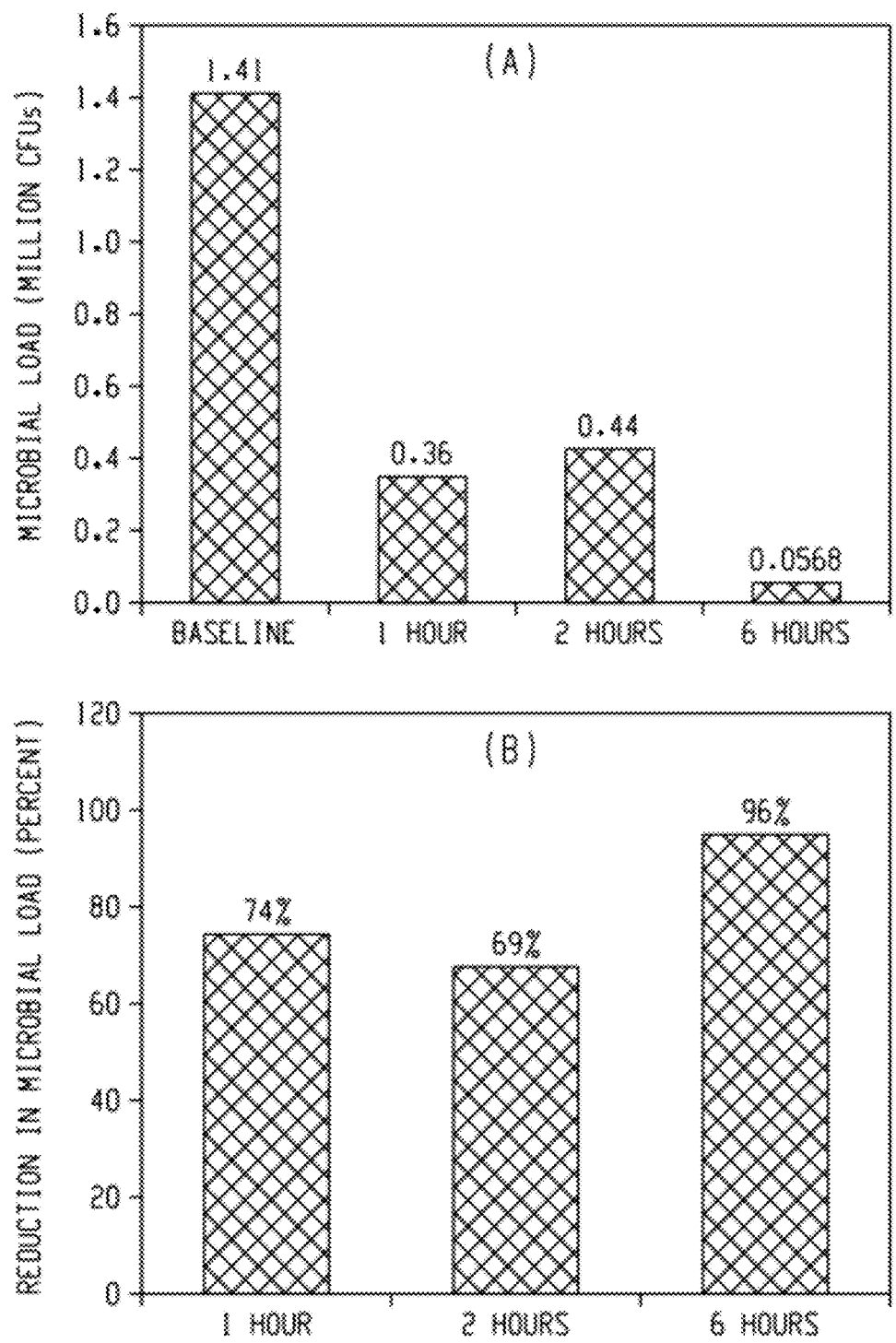
FIG. 29 is a graph showing the effect of a single dose of an example barrier-forming composition on oral microbial burden of a healthy individual, as described in Example 164-166. (A)—Microbial load in CFUs, (B) reduction in microbial load (%) compared to baseline.

The results showed that application of Example 7 led to consistent reduction in microbial load for up to 6 hours (See FIG. 29A, which shows CFUs of a representative tested individual. Treatment with the barrier-forming composition resulted in 69% to 96% reduction of the microbial burden in the oral cavity (See FIG. 29B, which shows a representative individual's reduction in microbial load.)

Examples 167-169

Long-Term Activity

The activity of the barrier-forming composition over a 5-day period against oral microbes was evaluated. In Examples 167-169, three healthy individuals were enrolled, and asked to apply a single dosage (three sprays as defined above) of Example 7 three times daily (approximately 9 AM, noon, and 3 PM) for a 5-day period (representing a typical 5-day work-week). Swabs were collected from these individuals at baseline (before application on day 1) and at the end of the day on each day during the 5-day period. Collected swabs were cultured on agar media plates, incubated for 24-28 hours at 37° C. and at 5% $CO_2$ humidity, and the number of CFUs were counted.

Figure 30:
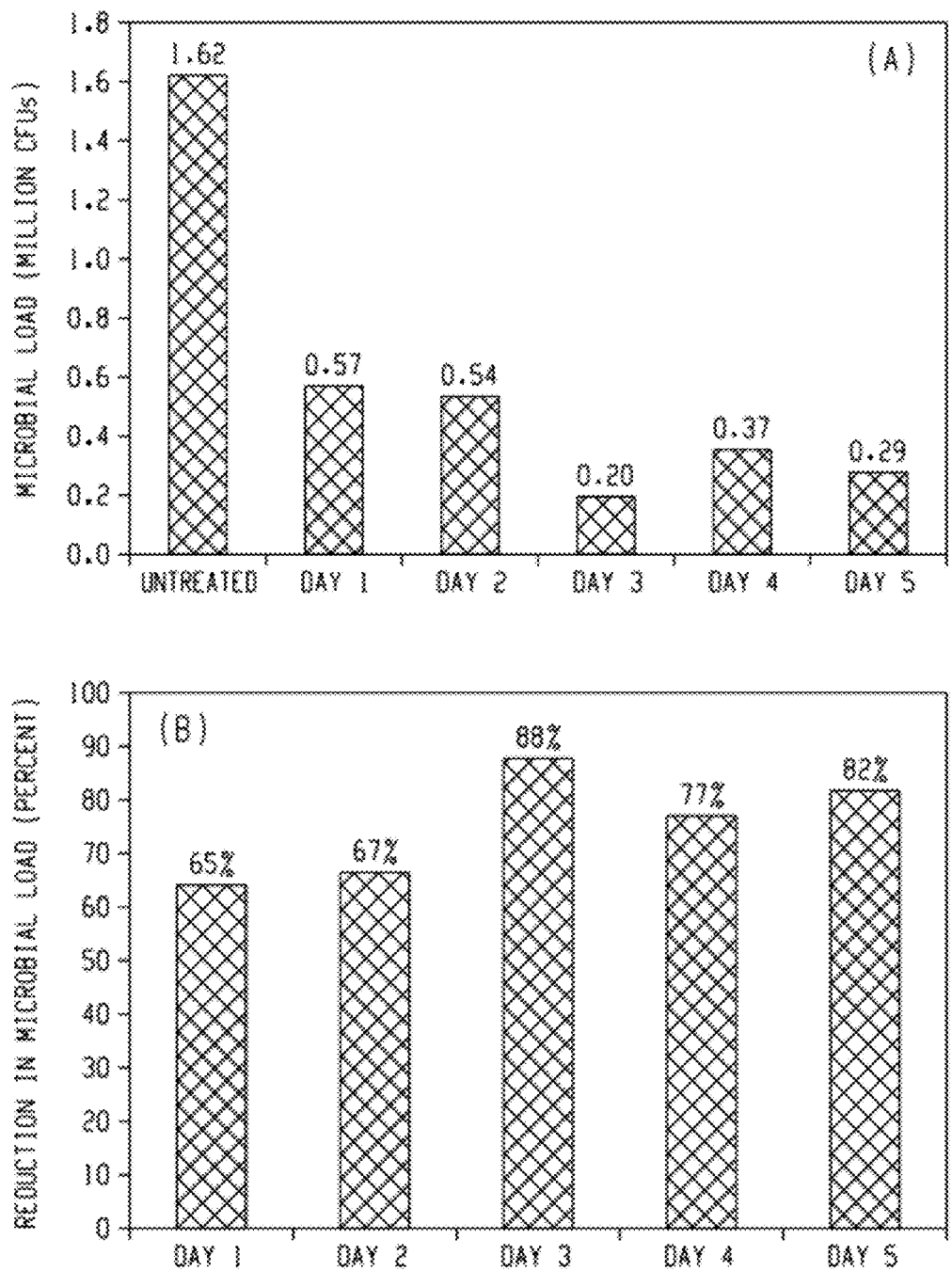
FIG. 30 is a graph showing the effect of an example barrier-forming composition on levels of oral microbes over a 5-day period in three healthy adults, as described in Examples 167-169.

The effect of the Example 7 barrier-forming composition on microbial burden was determined (as median CFUs for the three subjects), and percentage inhibition was calculated for each post-exposure time point relative to the baseline (0 min) CFUs. FIG. 30 shows these results in a graph of CFUs versus time (FIG. 30A) and reduction in microbial load versus time (FIG. 30B). Examples 167-169 demonstrate that application of Example 7 over 5 days led to consistent reduction in microbial load over the 5-day test period (FIG. 30A). Treatment with the Example 7 barrier-forming composition resulted in 65%-88% reduction of the median microbial burden in the oral cavity of the study participants (FIG. 30B).

Examples 170-198

Figure 31:
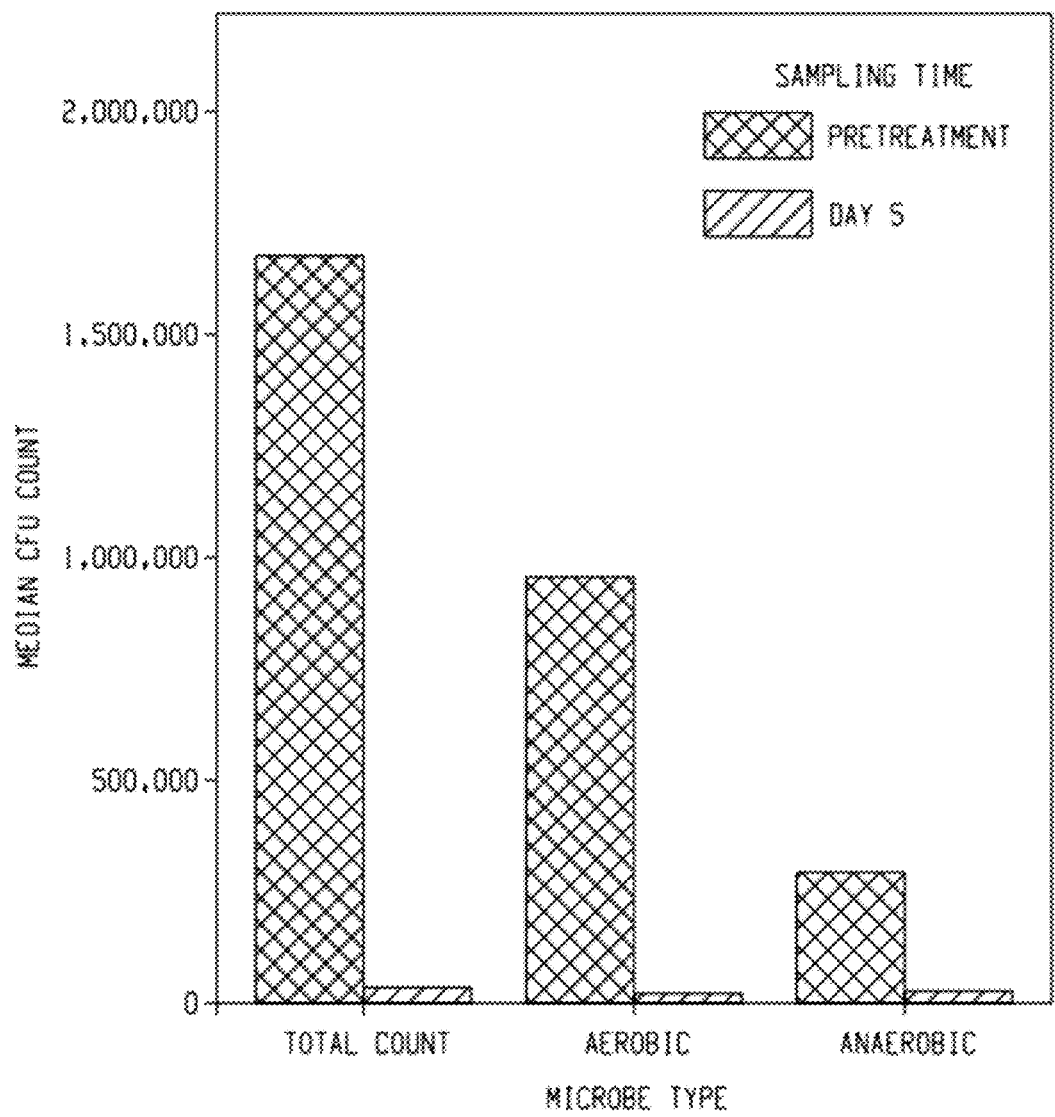
FIG. 31 is a graph showing the effect of an example barrier-forming composition on microbial burden of the oral cavity after 5-day usage in 31 healthy subjects, as described in Examples 170-198.
Figure 32:
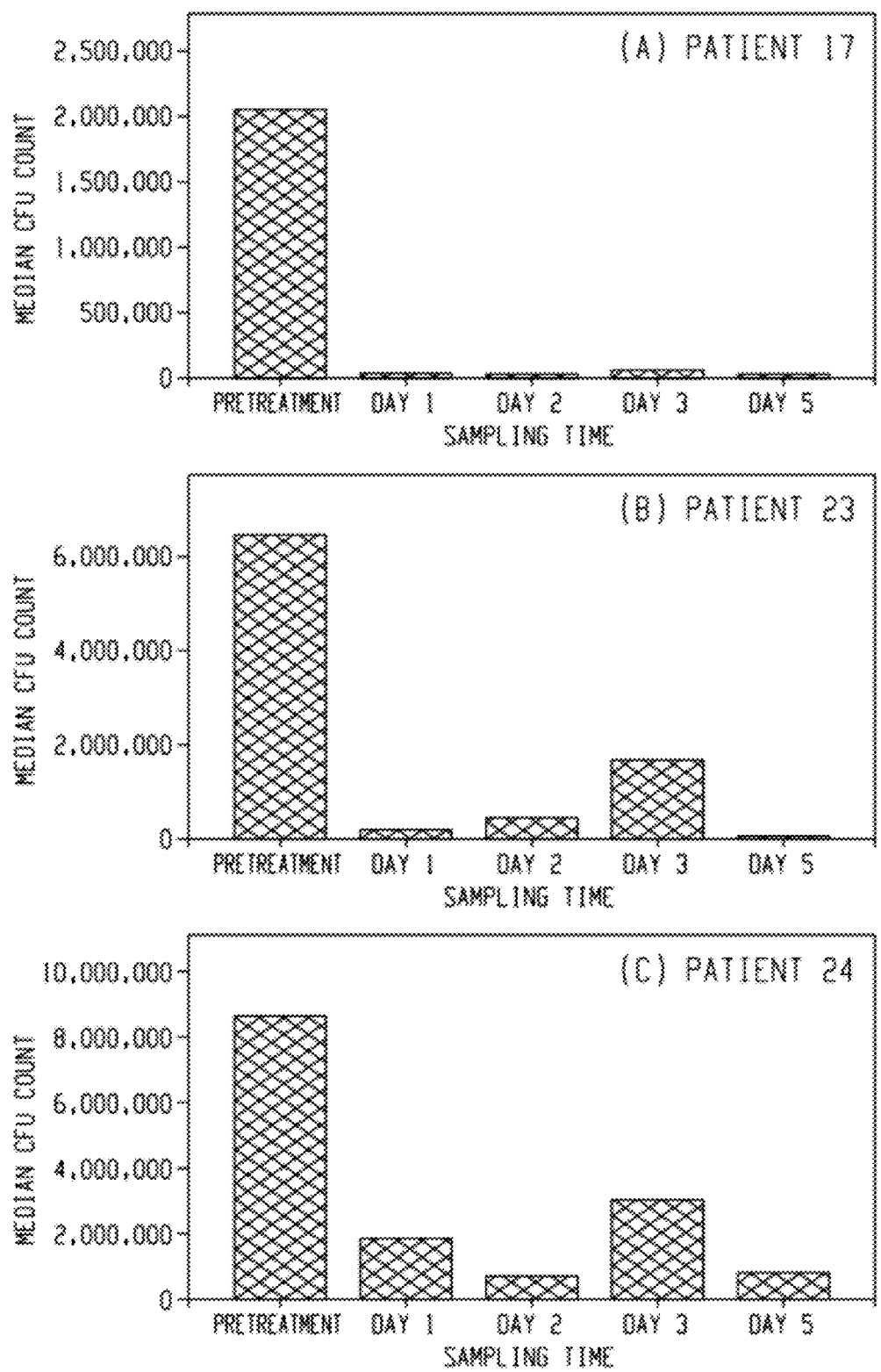
FIG. 32 is a graph showing the microbial load in oral samples obtained from three representative study participants, as described in Examples 170-198.

In a clinical study, twenty-nine healthy individuals were enrolled after informed consent. Baseline information was recorded (age in years, gender, ethnicity, and date of enrolment). Oral examination of the mouth was undertaken, and the inside of the mouth (cheek) was swabbed with a sterile culture swab. Baseline oral swab samples were cultured to determine bacterial load prior to study. In Examples 170-198, each of the twenty-nine participants were given a spray bottle containing the barrier-forming composition of Example 7 and instructed to spray the inside of their mouth six times (total volume sprayed is 0.75 ml), then swish for 30 seconds and swallow. Two groups of participants used the example barrier-forming composition every two hours, three times a day, for five days (a typical work week). Swabs were collected on days 1, 2, 3, and 5 and cultured on media specific for aerobic and anaerobic bacteria. Data were presented as number of microbes: total, aerobic and anaerobic. FIG. 31 shows a graph of total microbial load and breaks down the total into aerobic and anaerobic counts from just prior to treatment and on day 5 of treatment. FIG. 32 shows graphs of microbial load over the 5 day period in oral samples obtained from three representative study participants.

Overall, the in vivo testing showed that the barrier-forming composition exhibits antimicrobial activity against oral microbes, as measured by reduction in the levels of these organisms, over both short- and long-term duration.

The data showed that treatment with the barrier-forming composition over a 5-day period resulted in reduction in the oral microbial load, for total microbes, aerobic and anaerobic organisms.

Example 199-205

Identification of Additional Humectants for Forming a Barrier to Prevent Microbial Penetration In Example 199 an in vitro filter insert-based model (see FIG. 33) was used to test different humectants at different concentrations.

Six compositions were prepared according to Table XII based on the mixing procedures used for Examples 3-8

TABLE XII

| | Ex. 199 | Ex. 200 | Ex. 201 | Ex. 202 | Ex. 203 | Ex. 204 | Ex. 205 |
|---|---|---|---|---|---|---|---|
| Xanthan Gum | 0.4 | 0.4 | 0.4 | 0.4 | 0.4 | 0.4 | |
| Glycerin | 4.5 | 4.5 | 4.5 | | | | 4.5 |
| Sorbitol | | 4.5 | 4.5 | 4.5 | | 4.5 | |
| Xylitol | | | 4.5 | 4.5 | 4.5 | | 4.5 |

Next, 100 µL of Examples 199-205 were placed into filter inserts (pore size 0.8 µm diameter, that allows both bacteria and fungi to pass through) and allowed to a form a layer. Next, organisms were overlaid on the layer formed by the test solutions. The filter inserts containing the layer of test solutions and microorganisms were then placed on the surface of agar media plates and incubated for 24 hours at 37° C. After the incubation period, the agar media plates were evaluated for growth on filter insert and in the agar media. Growth on filter insert but no growth in agar media indicated that the test solution formed a barrier, which prevented the microbes from passing through. In contrast, microbial growth in the filter insert as well as the agar media indicated that no such barrier was formed.

The results showed that each of the xanthan gum-based solutions containing the tested humectants (singly or in combination) formed intact barriers on the filter insert that prevented the passage of microorganisms into underlying agar medium.

Example 206-213

Determination of the Solubility Limits of Xanthan Gum

To determine the solubility of xanthan gum, it was mixed at different concentrations in water and the solubility observed by monitoring the presence or absence of clumps and free flow of the mixture. Table XIII reports the results and concentrations.

TABLE XIII

| Example | Xanthan Gum Concentration | Solubility |
|---|---|---|
| 206 | 0.40% | free flowing viscous solution |
| 207 | 0.45% | some clumps, viscous solution |
| 208 | 0.5% | more clumps, viscous solution |
| 209 | 0.6% | clumps, more viscous than above |
| 210 | 0.7% | clumps, more viscous than above |
| 211 | 0.8% | Extensive clumps, highly viscous solution, no free flow |
| 212 | 0.9% | Extensive clumps, highly viscous solution, no free flow |
| 213 | 1.00% | Extensive clumps, highly viscous jelly, no free flow |

We found that when mixed at 0.4%, xanthan gum formed a free-flowing solution (Table XIII). In contrast, mixtures containing 0.45% or 0.5% xanthan gum formed a viscous fluid but contained small clumps. The extent of clumps increased with increasing concentration of xanthan gum (0.6% and 0.7%). At concentrations ≥0.8%, xanthan gum mixture contained extensive clumps, with a jelly-like consistency and no free flow.

Example 214

Comparison of Cationic CPC in Barrier-forming composition with Neutral Antimicrobial Agent in Barrier-forming composition In Example 214, the formulation of Example 7 was made, except the neutral agent Citral was used instead of CPC. The antimicrobial activity of formulations containing CPC (0.1%) or Citral (0.5%) against *Streptococcus* was ascertained. The assay described above in Examples 48-61 was used to perform these studies.

The results showed that the formulation containing citral exhibited antimicrobial activity (MIC=12.5%). However, activity of formulation containing citral was significantly less potent than that containing CPC (MIC=0.098%).

Example 215

Physico-Chemical Testing of Hydrophobicity and Comparison

In Example 215 thin layer chromatography analysis was used to compare the hydrophobicity of Example 7 with a hydrophobic composition. The hydrophobic composition was comprised of the components in Table XIV.

TABLE XIV

|  | Wt % |
|---|---|
| Glycerin | 7 |
| Sorbitol | 5 |
| Poloxamer 338 | 1 |
| PEG 60 Hydrogenated castor oil | 1 |
| VP/VA copolymer | 0.75 |
| Sodium benzoate | 0.5 |
| Cellulose Gum | 0.2 |
| CPC | 0.05 |
| Methyl Paraben | 0.05 |
| Propyl paraben | 0.05 |
| Sodium Saccharin | 0.05 |
| Xanthan Gum | 0.01 |
| Disodium Phosphate | 0.006 |
| Flavoring and coloring agents | 0.121 |

*the remainder of the composition was purified water

10 μL of Example 7 and the hydrophobic composition were deposited on pre-made TLC plates (at a distance of 2 cm from the bottom edge). The spots were air-dried for 5 minutes, and the plates were placed in a TLC chromatography jar containing water as a solvent. The TLC system was allowed to run until the solvent front reached the top edge of the plate. Plates were removed and the solvent and sample fronts were marked. The Relative Front (Rf) values were calculated for the two samples using the formula II:

$$Rf = \text{Distance travelled by spot/Distance travelled by solvent front} \quad \text{II.}$$

The results showed that the Rf value for the hydrophobic composition and Example 7 were 0.33 and 0, respectively, indicating that the hydrophobic composition was highly miscible in water. In contrast, Example 7 did not exhibit any mobility in the aqueous solvent, demonstrating that this formulation is hydrophobic or not hydrophilic.

It is claimed:

1. A barrier-forming composition comprising:
    a carbohydrate gum;
    a humectant; and
    an antimicrobial agent;
   wherein the composition meets the following requirements:
    about $0.01\% \leq C \leq$ about $0.4\%$;
    $4.5\% \leq H \leq$ about $65\%$; and
    $0.050\% < A$
    wherein all percentages are by weight of the total composition;
   wherein C is the carbohydrate gum; H is the humectant; and A is the antimicrobial agent;
    wherein the composition is a solution;
    wherein the composition, when applied to a mammal mucosa, has antimicrobial cidal or static activity against airborne germs for a duration of about two hours to about six hours based on in vivo testing.

2. The barrier-forming composition of claim 1, wherein the barrier-forming composition forms a film of about 0.001 mm to about 0.2 mm in average thickness upon application to a human mucosa.

3. The barrier-forming composition of claim 1, wherein the antimicrobial agent is selected from the group consisting of: biguanides, bisbiguanides, polyhexamethylene biguanides, or pharmaceutically acceptable salts thereof.

4. The barrier-forming composition of claim 1, wherein the antimicrobial agent is a quaternary ammonium cationic species or a pharmaceutically acceptable salt thereof.

5. The barrier-forming composition of claim 1, wherein the composition meets the following requirement: about $0.06\% \leq A \leq$ about $0.1\%$.

6. The barrier-forming composition of claim 1, wherein the composition has a Weybridge viscosity of about 16 to about 20 cps.

7. The barrier-forming composition of claim 1, wherein the carbohydrate gum has an overall negative charge.

8. The barrier-forming composition of claim 1, wherein the barrier-forming composition has a pH of 4 to 8.

9. The barrier-forming composition of claim 1, wherein the carbohydrate gum is a polysaccharide.

10. The barrier-forming composition of claim 1, wherein the carbohydrate gum is selected from the group consisting of: xanthan gum, guar gum, gum Arabic, tragacanth, gum karaya, locust bean gum, carob gum, and pectin.

11. The barrier-forming composition of claim 1, wherein the humectant is a polyol.

12. The barrier-forming composition of claim 1, wherein the humectant is selected from the group consisting of: glycerin, sorbitol, xylitol, propylene glycol, polyethylene glycol, and mixtures thereof.

13. The barrier-forming composition of claim 1, wherein the composition has an Rf value of 0 to about 0.25 in water.

14. The barrier-forming composition of claim 1, wherein the composition is not hydrophilic.

15. The barrier-forming composition of claim 1, wherein the barrier composition when applied to a mammal mucosa blocks microorganisms having a number average diameter of 30 nm or greater.

16. The barrier-forming composition of claim 1, wherein the composition is exclusive of teeth whitening and desensitizing agents.

17. The barrier-forming composition of claim 1, wherein the composition is exclusive of cellooligosaccharides, azelastine, silicon based oils, and potassium nitrate.

18. The barrier-forming composition of claim 1, wherein the composition, when applied to a mucosa of a mammal is active to prevent microorganisms from contacting the mucosa underneath the barrier composition for a duration of at least six hours.

19. The barrier-forming composition of claim 1, wherein the composition consists essentially of the carbohydrate gum, the humectant; and the antimicrobial agent.

20. The barrier-forming composition of claim 1, wherein A is about 0.1 or less.

21. A barrier-forming composition comprising:
    a carbohydrate gum;
    a humectant; and
    an antimicrobial agent;
   wherein the composition meets the following requirements:
    about $0.01\% \leq C \leq$ about $0.4\%$; and
    $4.5\% \leq H \leq$ about $65\%$;
    wherein all percentages are by weight of the total composition;
   the barrier-forming composition having an Rf value in water of 0 to about 0.25;

wherein the composition is a solution;
wherein the composition, when applied to a mammal mucosa, has antimicrobial cidal or static activity against airborne germs for a duration of about two hours to about six hours based on in vivo testing.

22. A method for making a mucosal barrier-forming composition comprising:
mixing and heating:
a carbohydrate gum;
a humectant; and
an antimicrobial agent;
forming a solution;
wherein the composition meets the following requirements:
about $0.01\% \leq C \leq $ about $0.4\%$;
$4.5\% \leq H \leq $ about $65\%$; and
$0.050\% < A$;
wherein all percentages are by weight of the total composition;
wherein the composition, when applied to a mammal mucosa, has antimicrobial cidal or static activity against airborne germs for a duration of about two hours to about six hours based on in vivo testing.

23. The barrier-forming composition of claim 1, wherein the composition has the property of forming a barrier upon application to a mucosa that traps and kills microorganisms.

24. The barrier-forming composition of claim 1, wherein the antimicrobial has cidal or static activity against a bacterial microorganism, a viral microorganism, and a fungal microorganism.

25. The barrier-forming composition of claim 1, wherein the carbohydrate gum is present at most in an amount of 0.4%.

* * * * *